United States Patent
Roberts et al.

(10) Patent No.: US 9,757,455 B2
(45) Date of Patent: *Sep. 12, 2017

(54) ORAL THERAPEUTIC COMPOUND DELIVERY SYSTEM

(75) Inventors: Michael Stephen Roberts, West Lake (AU); George Alexander Davidson, Larnook (AU); Ruoying Jiang, Sherwood (AU); Geraldine Ann Elliott, Mount Ommaney (AU); Keivan Bezanehtak, Castle Hill (AU); Stephen Douglas Chandler, Mayfield (AU); Greg Davey, Sinnamon Park (AU); Mantu Sarkar, Secunderabad (IN)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1324 days.

This patent is subject to a terminal disclaimer.

(21) Appl. No.: 12/085,645

(22) PCT Filed: Nov. 28, 2006

(86) PCT No.: PCT/AU2006/001798
§ 371 (c)(1),
(2), (4) Date: Jul. 14, 2009

(87) PCT Pub. No.: WO2007/059591
PCT Pub. Date: May 31, 2007

(65) Prior Publication Data
US 2009/0311327 A1    Dec. 17, 2009

(30) Foreign Application Priority Data

Nov. 28, 2005  (AU) ................................ 2005906628
Apr. 13, 2006  (AU) ................................ 2006901964
Apr. 13, 2006  (AU) ................................ 2006901973

(51) Int. Cl.
| A61K 31/192 | (2006.01) |
| A61K 45/06  | (2006.01) |
| A61K 9/20   | (2006.01) |
| A61K 31/167 | (2006.01) |
| A61K 31/437 | (2006.01) |

(52) U.S. Cl.
CPC ............ *A61K 45/06* (2013.01); *A61K 9/2009* (2013.01); *A61K 9/2013* (2013.01); *A61K 9/2054* (2013.01); *A61K 9/2059* (2013.01); *A61K 31/167* (2013.01); *A61K 31/437* (2013.01)

(58) Field of Classification Search
None
See application file for complete search history.

(56) References Cited

U.S. PATENT DOCUMENTS

| 3,390,049 A | 6/1968 | Rednick |
| 3,851,032 A | 11/1974 | Andrews et al. |
| 4,309,408 A | 1/1982 | Pathak et al. |
| 4,687,662 A | 8/1987 | Schobel |
| 4,704,269 A | 11/1987 | Korab |
| 4,704,405 A | 11/1987 | O'Neill et al. |
| 4,824,664 A | 4/1989 | Tarral et al. |
| 4,834,966 A | 5/1989 | Gazzaniga et al. |
| 4,942,039 A | 7/1990 | Duvall et al. |
| 5,019,399 A | 5/1991 | Appelgren et al. |
| 5,064,656 A | 11/1991 | Gergely et al. |
| 5,075,291 A | 12/1991 | DuRoss |
| 5,102,665 A | 4/1992 | Schaeffer |
| 5,118,528 A | 6/1992 | Fessi et al. |
| 5,145,684 A | 9/1992 | Liversidge et al. |
| 5,158,779 A | 10/1992 | Gergely et al. |
| 5,178,878 A | 1/1993 | Wehling et al. |
| 5,225,197 A | 7/1993 | Bolt et al. |
| 5,260,304 A | 11/1993 | Gergely et al. |
| 5,262,171 A | 11/1993 | Login et al. |
| 5,273,759 A | 12/1993 | Simmons |
| 5,312,626 A | 5/1994 | Gergely et al. |
| 5,348,475 A | 9/1994 | Waknine et al. |
| 5,348,745 A | 9/1994 | Daher |
| 5,419,898 A | 5/1995 | Ikejiri et al. |
| 5,424,075 A | 6/1995 | Daher et al. |
| 5,425,950 A | 6/1995 | Dandiker et al. |
| 5,527,540 A | 6/1996 | Gergely et al. |
| 5,587,179 A | 12/1996 | Gergely et al. |

(Continued)

FOREIGN PATENT DOCUMENTS

| CA | 2 326 809 | 3/1999 |
| DE | 19814392 | 3/1998 |

(Continued)

OTHER PUBLICATIONS http://www.ncbi.nlm.nih.gov/pubmedhealth/PMH0000003/ viewed on Mar. 7, 2012.*

(Continued)

*Primary Examiner* — Jessica Worsham

(74) *Attorney, Agent, or Firm* — Victor Tsu

(57) ABSTRACT

The present invention provides an oral delivery system for a therapeutic compound that is an acid, a salt of an acid or an unionized compound or a proactive form thereof with pharmacological, physiological or biochemical activity. The present invention particularly provides a swallow formulation comprising a therapeutic compound that is an acid, a salt of an acid or an unionized compound or a proactive form thereof which facilitates the rapid delivery of the therapeutic compound to the circulatory system.

15 Claims, 33 Drawing Sheets

(56) References Cited

U.S. PATENT DOCUMENTS

| | | |
|---|---|---|
| 5,593,693 A | 1/1997 | Gergely et al. |
| 5,639,475 A | 6/1997 | Bettman et al. |
| 5,670,170 A | 9/1997 | Grimmett et al. |
| 5,681,583 A | 10/1997 | Conte et al. |
| 5,709,886 A | 1/1998 | Bettman et al. |
| 5,733,578 A | 3/1998 | Hunter et al. |
| 5,750,145 A | 5/1998 | Patell |
| 5,759,575 A | 6/1998 | Gergely et al. |
| 5,762,951 A | 6/1998 | Maasz et al. |
| 5,792,473 A | 8/1998 | Gergely et al. |
| 5,807,577 A | 9/1998 | Ouali |
| 5,807,578 A | 9/1998 | Acosta-Cuello et al. |
| 5,814,337 A | 9/1998 | Merrifield et al. |
| 5,840,737 A | 11/1998 | Phillips |
| 5,854,226 A | 12/1998 | Penkler et al. |
| 5,858,410 A | 1/1999 | Muller et al. |
| 5,863,559 A | 1/1999 | Phillips et al. |
| 5,869,095 A | 2/1999 | Gergely et al. |
| 5,914,129 A | 6/1999 | Mauskop |
| 5,922,355 A | 7/1999 | Parikh et al. |
| 5,962,022 A | 10/1999 | Bolt et al. |
| 6,020,001 A | 2/2000 | Phillips et al. |
| 6,051,254 A | 4/2000 | Merrifield et al. |
| 6,077,536 A | 6/2000 | Merrifield et al. |
| 6,149,938 A | 11/2000 | Bonadeo |
| 6,156,506 A | 12/2000 | Yamamoto et al. |
| 6,160,020 A | 12/2000 | Ohannesian et al. |
| 6,165,506 A | 12/2000 | Jain et al. |
| 6,171,617 B1 | 1/2001 | Gruber |
| 6,197,336 B1 | 3/2001 | Grassano et al. |
| 6,210,711 B1 | 4/2001 | Aiache et al. |
| 6,214,386 B1 | 4/2001 | Santus et al. |
| 6,217,907 B1 | 4/2001 | Hunter et al. |
| 6,242,002 B1 | 6/2001 | Tritthart et al. |
| 6,245,353 B1* | 6/2001 | Tritthart et al. ............... 424/466 |
| 6,258,814 B1 | 7/2001 | Martin |
| 6,274,172 B1 | 8/2001 | Mention |
| 6,277,409 B1 | 8/2001 | Luber |
| 6,284,272 B1 | 9/2001 | Chiesi et al. |
| 6,309,668 B1 | 10/2001 | Bastin et al. |
| 6,316,025 B1 | 11/2001 | Grattan |
| 6,348,485 B1 | 2/2002 | Ohkawa et al. |
| 6,350,470 B1 | 2/2002 | Pather et al. |
| 6,368,627 B1 | 4/2002 | Phillips et al. |
| 6,383,471 B1* | 5/2002 | Chen et al. ..................... 424/45 |
| 6,391,337 B2 | 5/2002 | Hunter et al. |
| 6,432,450 B1 | 8/2002 | Gergely et al. |
| 6,479,551 B1 | 11/2002 | Plachetka et al. |
| 6,488,961 B1 | 12/2002 | Robinson et al. |
| 6,489,346 B1 | 12/2002 | Phillips |
| 6,509,036 B2 | 1/2003 | Pather et al. |
| 6,514,531 B1 | 2/2003 | Alaux et al. |
| 6,589,556 B2 | 7/2003 | Cherukuri |
| 6,620,433 B2 | 9/2003 | Martin et al. |
| 6,638,535 B2 | 10/2003 | Lemmens et al. |
| 6,641,838 B2 | 11/2003 | Pather et al. |
| 6,645,988 B2 | 11/2003 | Phillips |
| 6,649,186 B1 | 11/2003 | Robinson et al. |
| 6,667,056 B2 | 12/2003 | Chiesi et al. |
| 6,699,885 B2 | 3/2004 | Phillips |
| 6,750,237 B1 | 6/2004 | Dearn et al. |
| 6,780,882 B2 | 8/2004 | Phillips |
| 8,048,449 B2 | 11/2011 | Kashid et al. |
| 2001/0014340 A1 | 8/2001 | Ohta et al. |
| 2002/0031547 A1 | 3/2002 | Takagi et al. |
| 2002/0034540 A1 | 3/2002 | Price |
| 2002/0071864 A1 | 6/2002 | Kim et al. |
| 2002/0076439 A1 | 6/2002 | Pather et al. |
| 2002/0110578 A1 | 8/2002 | Pather et al. |
| 2003/0003146 A1 | 1/2003 | Takagi et al. |
| 2003/0026834 A1* | 2/2003 | Jamali ............... A61K 9/0007 424/465 |
| 2003/0035833 A1 | 2/2003 | He |
| 2003/0069213 A1 | 4/2003 | Ii et al. |
| 2003/0091626 A1 | 5/2003 | Katsuta |
| 2003/0096013 A1 | 5/2003 | Werling et al. |
| 2003/0133976 A1 | 7/2003 | Pather et al. |
| 2003/0170301 A1 | 9/2003 | Wehling |
| 2003/0175355 A1 | 9/2003 | Tobyn et al. |
| 2003/0185886 A1 | 10/2003 | Lee et al. |
| 2003/0203007 A1 | 10/2003 | Ukai et al. |
| 2003/0215500 A1 | 11/2003 | Ohta et al. |
| 2003/0236183 A1 | 12/2003 | De Bruijn et al. |
| 2004/0014680 A1 | 1/2004 | Nakagami et al. |
| 2004/0071772 A1 | 4/2004 | Narita et al. |
| 2004/0170681 A1 | 9/2004 | Grattan |
| 2004/0180089 A1 | 9/2004 | Plachetka et al. |
| 2004/0204475 A1 | 10/2004 | Humphrey |
| 2004/0247677 A1 | 12/2004 | Oury et al. |
| 2005/0032867 A1 | 2/2005 | Baker et al. |
| 2005/0042281 A1* | 2/2005 | Singh et al. .................. 424/464 |
| 2005/0136120 A1 | 6/2005 | Kugelmann et al. |
| 2005/0147671 A1 | 7/2005 | Reiner et al. |
| 2005/0215643 A1 | 9/2005 | Reiner et al. |
| 2005/0276847 A1 | 12/2005 | Roberts et al. |
| 2007/0134317 A1 | 6/2007 | Gruber et al. |
| 2007/0141144 A1 | 6/2007 | Roberts et al. |
| 2007/0184101 A1 | 8/2007 | Hrakovsky et al. |
| 2007/0184108 A1 | 8/2007 | Hrakovsky et al. |
| 2008/0287456 A1 | 11/2008 | Roberts et al. |
| 2009/0124657 A1 | 5/2009 | Kappala et al. |
| 2010/0120848 A1 | 5/2010 | Hrakovsky et al. |

FOREIGN PATENT DOCUMENTS

| | | |
|---|---|---|
| EP | 1818057 A1 | 8/2007 |
| EP | 2158911 A1 | 3/2010 |
| GB | 1 410 909 | 10/1971 |
| GB | 2 103 087 | 7/1982 |
| WO | 9744023 | 5/1997 |
| WO | 98/38983 | 2/1998 |
| WO | WO-98/35666 A1 | 8/1998 |
| WO | WO-00/13672 A1 | 3/2000 |
| WO | 00/57857 | 10/2000 |
| WO | 02/100319 | 12/2002 |
| WO | 02/100391 | 12/2002 |
| WO | WO/02/100391 | 12/2002 |
| WO | WO 03/026610 | 4/2003 |
| WO | WO-03/035036 A1 | 5/2003 |
| WO | 03/047552 | 6/2003 |
| WO | 03/074029 | 9/2003 |
| WO | 03/082247 A2 | 10/2003 |
| WO | 2004/004705 | 1/2004 |
| WO | 2004/012708 A1 | 2/2004 |
| WO | 2004/017976 | 3/2004 |
| WO | WO 2005/041938 | 5/2005 |
| WO | WO 2005/115344 | 12/2005 |
| WO | WO-2005/115345 | 12/2005 |
| WO | WO-2007/059591 A1 | 5/2007 |
| WO | WO-2007/077135 A1 | 7/2007 |
| WO | WO-2007/092031 A1 | 8/2007 |
| WO | WO-2008/014175 A2 | 1/2008 |
| WO | WO-2008/124081 A2 | 10/2008 |
| WO | WO-2009153305 A2 | 12/2009 |

OTHER PUBLICATIONS

Arthur H. Goldberg et al., *Increasing Dissolution Rates and Gastrointestinal Absorption of Drugs Via Solid Solutions and Eutectic Mixtures I*, 54 J. Pharm. Sci., 1145-1148 (1965).

Babalola et al., "Correlation between in vitro and in vivo parameters of commercial paracetamol tablets," (2001), Afr. J. Med Sci, 30, pp. 275-280.

Borin et al., "Single dose bioavailability, of acetaminophen following oral administration," (1989), International Journal of Pharmaceutics, 54, pp. 199-209.

Dominguez et al., "Bioequivalence study of paracetamol tablets: In vitro-in vivo correlation," (2000), Drug Development and Industrial Pharmacy, 26(8), pp. 821-828.

H.M. El-Banna et al., *The Application of Solid Dispersion Technique in the Preparation of Therapeutic Tablets*, 32(8-9) Die Phamazie, 511-515 (1977).

(56) References Cited

OTHER PUBLICATIONS

Hedges et al., "A comparison of the absorption of effervescent preparations of paracetamol and penicillin V (Phenoxymethylpenicillin) with solid dose forms of these drugs," (1974), J. Clin. Pharmacol., 14, pp. 363-368.
Hekimoglu et al., "Comparative bioavailability of three batches of four commercial acetaminophen tablets," (1991), European Journal of Drug Metabolism and Pharmacokinetics, pp. 228-232.
Hekimoglu et al., "Comparative bioavailability of three commercial acetaminophen tablets," (1987), International J. Clin. Pharmacol., 25(2), pp. 93-96.
Ishikawa et al., "Pharmacokinetics of acetaminophen from rapidly disintegrating compressed tablet prepared using microcrystalline cellulose (PH-M-06) and spherical sugar granules," Chem. Pharm. Bull. (2001), 49(2), pp. 230-232.
Ivanov et al., Direct cytotoxicity of non-steroidal anti-inflammatory drugs in acidic media: model study on human erythrocytes with DIDS-inhibited anion exchanger, 2002, Pharmazie, vol. 57 (12), p. 848, abstract only.
Kolloffel et al., Rectal administration of paracetamol a comparison of a solution and suppositories in adult volunteers, 1996, Pharmacy World and Science, vol. 18, No. 1, pp. 26-29.
L. Kalantzi, et al. "*Biowaiver monographs for immediate release solid oral dosage forms: Acetaminophen (paracetamol)*" Journal of Pharmaceutical Sciences vol. 95, Issue 1, pp. 4-14.
Moolenaar et al., Biopharmaceutics of rectal adminstration of drugs in man, 1979, Pharmaceutish Weekblad Scientific Edition, vol. 1, pp. 689-694.
Office Action from related U.S. Appl. No. 11/597,341, mailed May 12, 2010.
Particle characterization in Excipients, drug products, and drug substances, accessed Oct. 7, 2009. http:www.geochem.sgs.com/lsnewsqc/lsnewwsqu_july_issue/particle_characterisation_in_excipients_drug_products_and drug_substances_Iss_newsletter.htm.
Retaco et al., "Bioavailibility study of paracetamol tablets in saliva and urine," (1996), European Journal of Drug Metabolism and Pharmacokinetibs, 4, pp. 295-300.
Rygnestad et al., "Absorption of effervescent paracetamol tablets relative to ordinary paracetamol tablets in healthy volunteers," (2000), Eur J. Clin Pharmacol, 56, pp. 141-143.
Sevilla-Tirado et al., "Bioavailability of two new formulations of paracetamol compared with three marketed formulations, in healthy volunteers," (2003), Methods Find Exp Clin Pharmacol, 25(7), pp. 531-535.
Soininen et al., "Dissolution rate of different kinds of granulated micronized paracetamol with adjuvant incorporated either inter-or intragranularly,"-(1981), Acta Pharm. Fenn, 90, pp. 153-162.
Sotiropoulus et al., "Comparative bioavailability of three commercial acetaminophen tablets," (1981), Journal of Pharmaceutical Sciences, 70(4), pp. 422-425.
*The Dissolution of Paracetamol Tablets and the in Vitro Transfer of Paracetamol with and Without Sorbitol*, 20 British Pharmaceutical Conference, 228S-231S.
US Pharmacopeia, Particle Size Distribution Estimation by Analytical Sieving, accessed Oct. 7, 2009. http://www.pharmacopeia.cn/v29240/usp29nf24sO_c786.html.
Avdeef, "Solubility of sparingly-soluble ionizable drugs", Advanced Drug Delivery Reviews (2007), vol. 59, pp. 568-590.
Balasubramaniam et al., "Effect of Superdisintegrants on Dissolution of Cationic Drugs", Dissolution Technologies (2008), pp. 18-25.
Bergstrom et al., "Accuracy of calculated pH-dependent aqueous drug solubility", European Journal of Pharmaceutical Sciences (2004), vol. 22, pp. 387-398.
Carnaby-Mann et al., "Pill Swallowing by Adults With Dysphagia", Arch Otolaryngol Head Neck Surg (2005), vol. 131, pp. 970-975.
Douroumis, "Practical approaches of taste masking technologies in oral solid forms", Expert Opin. Drug Deliv. (2007), vol. 4(4), pp. 417-426.

Florence et al., Physicochemical Principles of Pharmacy, Third Edition, pp. 163-167.
Overgaard et al., "Patients' evaluation of shape, size and colour of solid dosage forms", Pharm World Sci (2001), vol. 23(5), pp. 185-188.
Sohi et al., "Taste Masking Technologies in Oral Pharmaceuticals: Recent Developments and Approaches", Drug Development and Industrial Pharmacy (2004), vol. 30(5), pp. 429-448.
"Disintegration", Physical Tests, (701) p. 2411.
Rubinstein et al., The effect of Excipient Solubility on the in-vitro and in-vivo properties of bendrofluazide tablets 5mg, 1977, vol. 3, No. 5, pp. 439-450, Abstract Only.
Office Action dated Aug. 27, 2010 in U.S. Appl. No. 11/604,972.
Office Action dated May 25, 2010 in U.S. Appl. No. 11/604,972.
Amendment dated Aug. 12, 2010 in U.S. Appl. No. 11/597,341.
Office Action dated May 12, 2010 in U.S. Appl. No. 11/597,341.
Anteer et al, J.Pharm.Sci, 72:955-958 (1983).
Amidon et al. Pharm. Res (1995) 12(3) 413-20.
Balan et al, J.Pharm. Sci 90(8) (2001) 1176-1185.
Chen et al, Chem. Pharm. Bull (Tokyo) 46(3): 478-81 (1998).
Clements et al., Clin.Pharmacol. Ther. 24:420-431 (1978).
El Banna et al, Int. J. Pharm. 208(1-2): 87-99 (1997).
Femi-Oweyo et al, Int. J. Pharm. 112(1)-17-23 (1994).
Garekani et al, Int. J. Pharm. 208(1-2):87-99 (1997).
Garekani et al, Int. J. Pharm. 208: 101-110 (2000).
Garekani et al. Drug Dev. Ind. Pharm. 2a(2): 173-179 (2003).
Goldberg et al, J.Pharm.Biophrm 49(3):225-229 (2000).
Grattan et al, Eur J.Pharm. Biophrm 49(3):225-229 (2000).
Gunn, Cooper & Gunn's Dispensing for Pharmaceutical Students 11th Edition: p. 102 (1965).
Heading et al, Brit.J.Pharmacol. 47:415-521 (1973).
Jaroninski et al, N. Eng.J.Med. 325:1315-1316 (1991).
Kelly et al, Phamiaceutical Research, 20(10) 1668-1673, Oct. 2003 entitled Comparison of the Rates of Disintegration, Gastric Emptying and Drug Absorption Following Administration of a New and Conventional Paracetamol Formulation Using Gamma Scintigraphy.
Lieberman et al, Pharmaceutical Dosage Forms: Tablets vol. 1 (1989) pp. 5-12, 69.
Lloyd et al (Eur.J.Pharm and Biopharm 48(1):59-65 (199).
Neuvonon et al, Clin. Pharmacokinet. 27(2) 120-8 (1994).
Nielson et al, European Journal of Clinical Pharmacology, 42(3): 261-264 (1992).
Prescott, Medical Clinics of North America, 58:907-916 (1974).
Prescott, American Journal of Therapeutics 7(2): 143-147 (2000).
Rostami-Hodjegan et al, Drug Dev. & Ind. Pharm. 28:523-531 (2002).
Rostami-Hodjegan et al, Drug Dev. & Ind Pharm. 28:533-543 (2002).
Rumack et al, Pediatrics 62(Suppl):898-903 (1978).
Rumble et al, Clin. Pharmacokinet. 20(2): 167-173 (1991).
Ruinstein et al, J.Pharm.Pharmacol., 26(6):363-366 (1977).
Sekikawa et al, Chem. Pharm. Bull. 27:31-37 (1979).
Sekikawa et al, Chem. Phann. Bull 27:(5): 1106-1111 (1979).
Sekikawa et al, chem. Pharm. Bull. 27:1223-1230 (1979).
Shaw et al, Drug Dev. & Ind. Pharm. 28:1147-1153 (2002).
Shaw et al, British Pharmaceutical Conference 2001, Abstract Book: 196.
Shi et al, Chin. J. Hosp. Pharm. 14:291-293 (1994).
M. Iwuagwu, A. Onyekwell, Tropical J. Pharm. Res. 1(1):29-37 (2002).
Walters, J. Pharm. Pharmacol. 20:228s-231s (1968).
Garekani et al, Int. J. Pharm. 208: 87-89 (2000).
Garekani et. Al. Int. J. Pharm. 208: 101-110 (2000).
Non-Final Office Action dated Jun. 5, 2008 issued in U.S. Appl. No. 11/604,972.
Final Office Action dated Dec. 30, 2008 issued in U.S. Appl. No. 11/604,972.
Non-Final Office Action dated Oct. 13, 2009 issued in U.S. Appl. No. 11/604,972.
Non-Final Office Action dated Mar. 30, 2011 issued in U.S. Appl. No. 11/604,972.

(56) References Cited

OTHER PUBLICATIONS

Final Office Action dated Oct. 13, 2011 issued in U.S. Appl. No. 11/604,972.
Final Office Action dated Oct. 25, 2010 issued in U.S. Appl. No. 11/597,341.
Office Action dated Mar. 21, 2012 issued in U.S. Appl. No. 11/597,341.
European Official Communication dated Apr. 25, 2012 issued in corresponding European Patent Application No. 05 742 209.9.
Canadian Search Report dated Nov. 14, 2012 in Application No. CA 2629904.
European Search Opinion dated Sep. 21, 2012 in European Patent Application No. 06 81 7548.
Supplementary European Search Report dated Sep. 21, 2012 in European Patent Application No. 06 81 7548.
Shaw, L.R. et al., "The Effect of Selected Water-Soluble Excipients on the Dissolution of Paracetamol and Ibuprofen," Drug Development and Industrial Pharmacy, 31:515-525, 2005.
Office Action dated Feb. 27, 2013 in U.S. Appl. No. 11/597,341, filed Jun. 11, 2008.
Office Action dated Feb. 27, 2013 in U.S. Appl. No. 13/618,728, filed Sep. 14, 2012.
Segre, Eugene J., M.D. The New England Journal of Medicine. Effects of Antacids on Naproxen Absorption. vol. 291. No. 11 pp. 582-583. (1974).

\* cited by examiner

*Figure 1*   Dissolution of Ibuprofen Sodium and Ibuprofen mixtures in 900 mL 0.0033 N HCl at 30 rpm
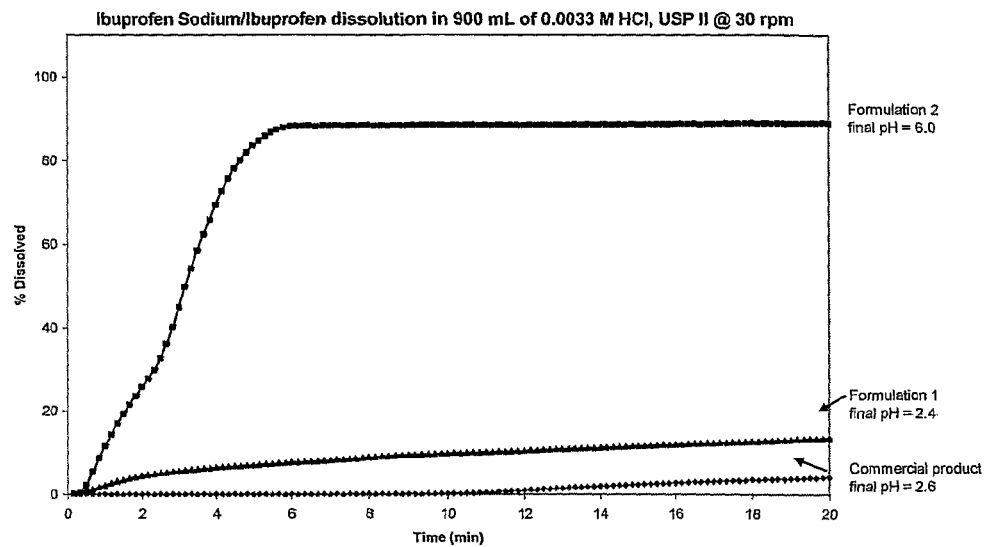
*Figure 2*   Dissolution of Ibuprofen in 900 mL 0.0033 N HCl at 30 rpm
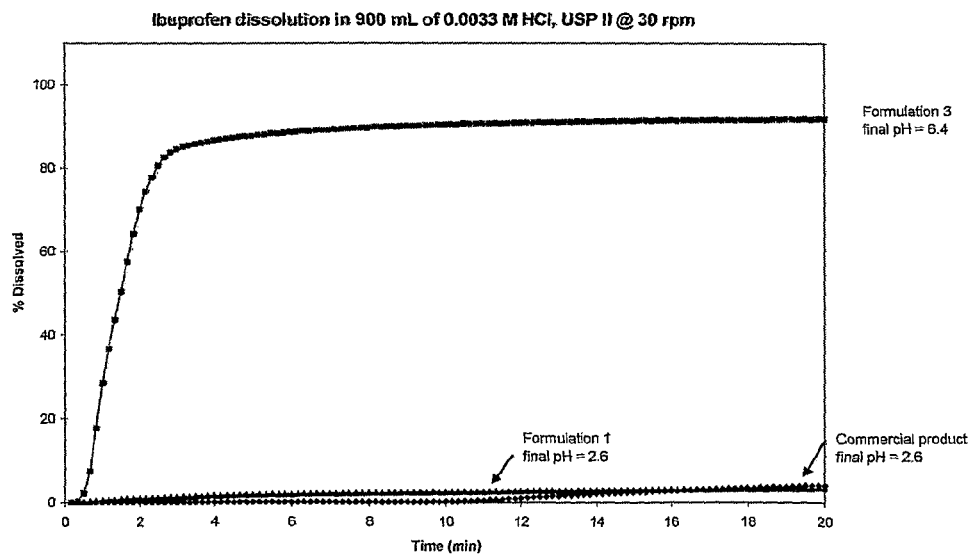

*Figure 3*     *Dissolution of Diclofenac Potassium in 900 mL 0.0033 N HCl at 30 rpm*
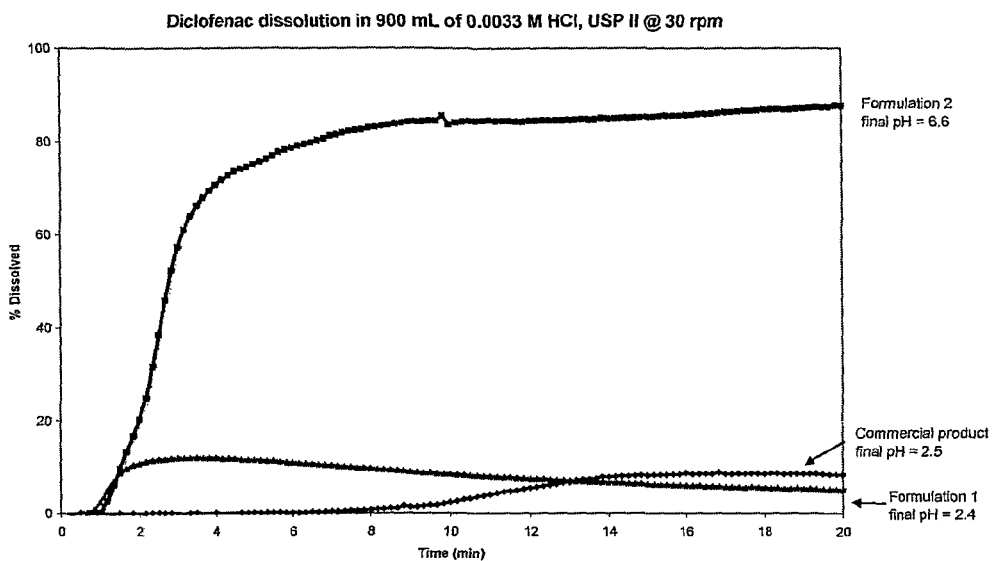
*Figure 4*     *Dissolution of Paracetamol in 900 mL 0.0033 N HCl at 30 rpm*
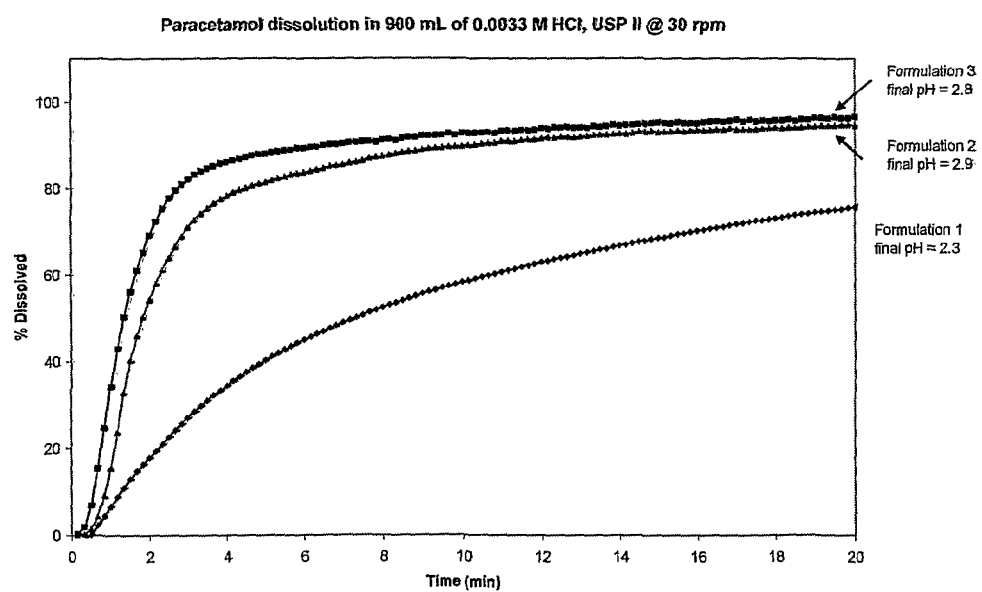

Figure 5    Dissolution of Naproxen in 900 mL 0.0033 N HCl at 30 rpm
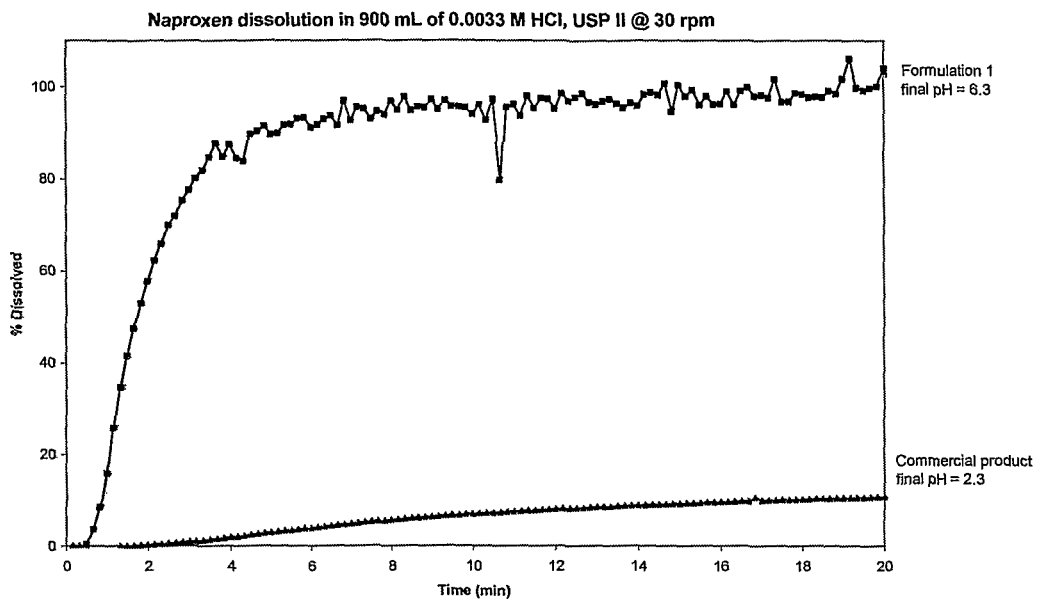
Figure 6    Dissolution of Naproxen Sodium in 900 mL 0.0033 N HCl at 30 rpm
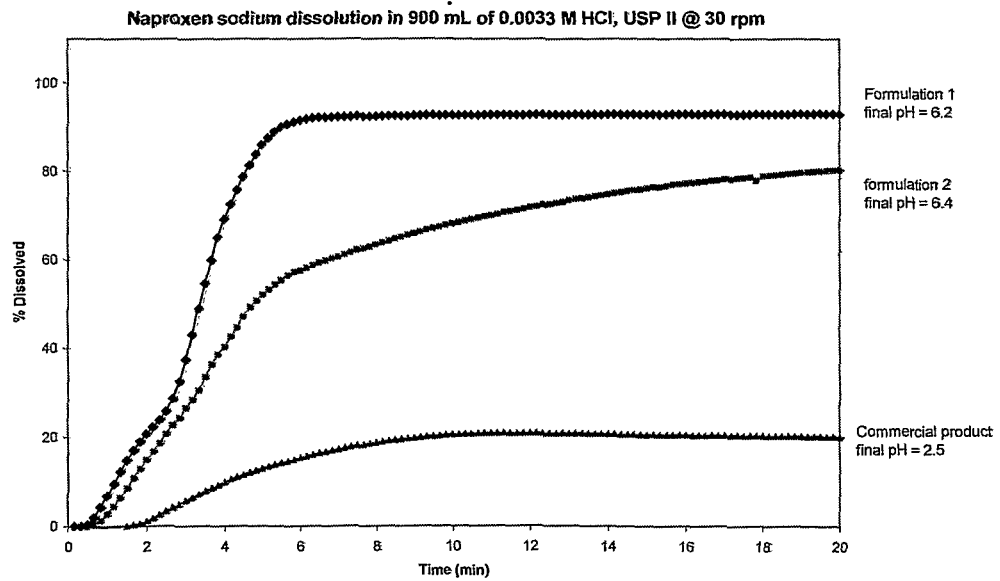

*Figure 7    Dissolution of Gemfibrozil in 900 mL 0.0033 N HCl at 30 rpm*
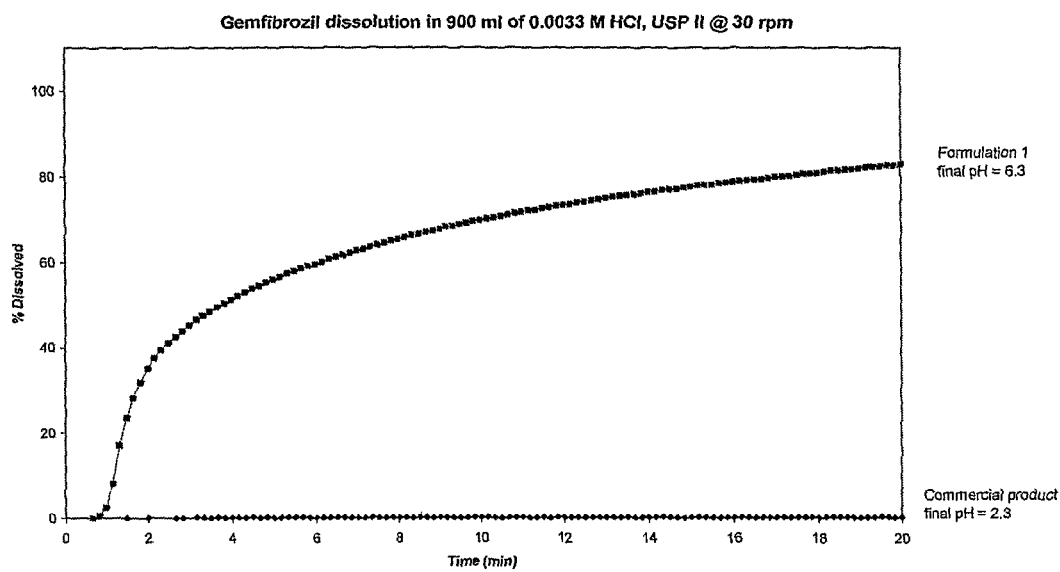
*Figure 8    Dissolution of Furosemide in 900 mL 0.0033 N HCl at 30 rpm*
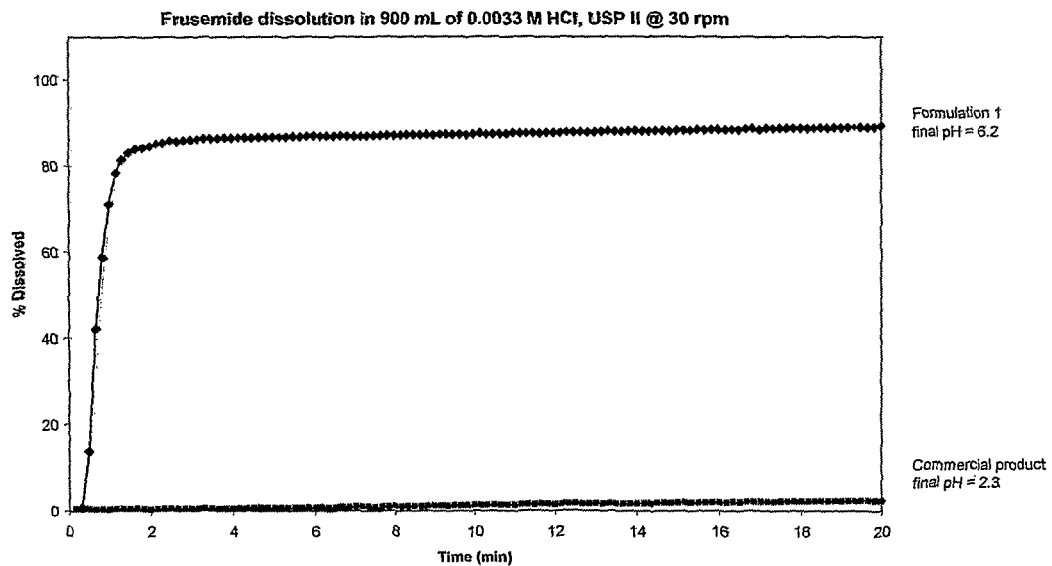

Figure 9  Dissolution profile for Temazepam in 900 mL 0.0033 M HCl at 30 rpm
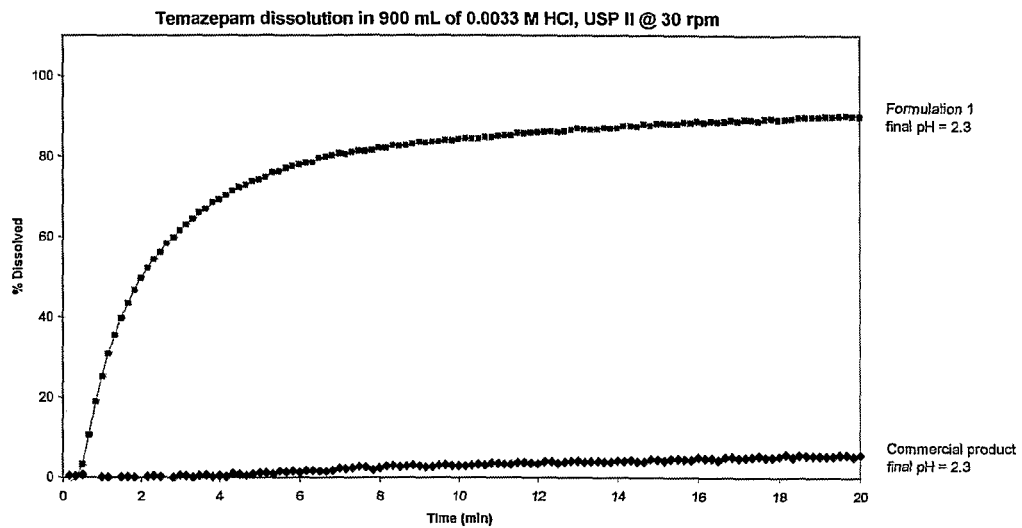
Figure 10  Dissolution profile for Montelukast Sodium in 900 mL 0.0033 M HCl at 30 rpm
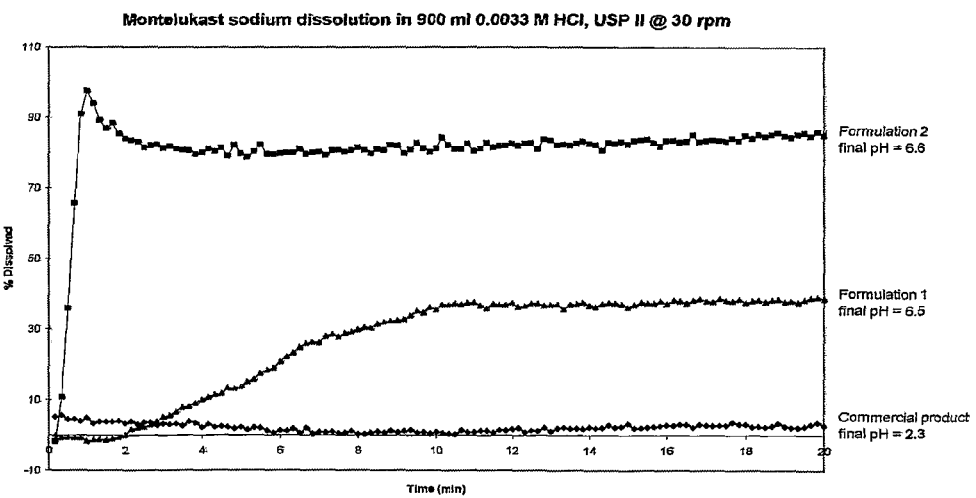

*Figure 11*    *Dissolution profiles for a mixture of Ibuprofen and Sodium Ibuprofen in 900 mL 0.0033 M* HCl *at 0 rpm*
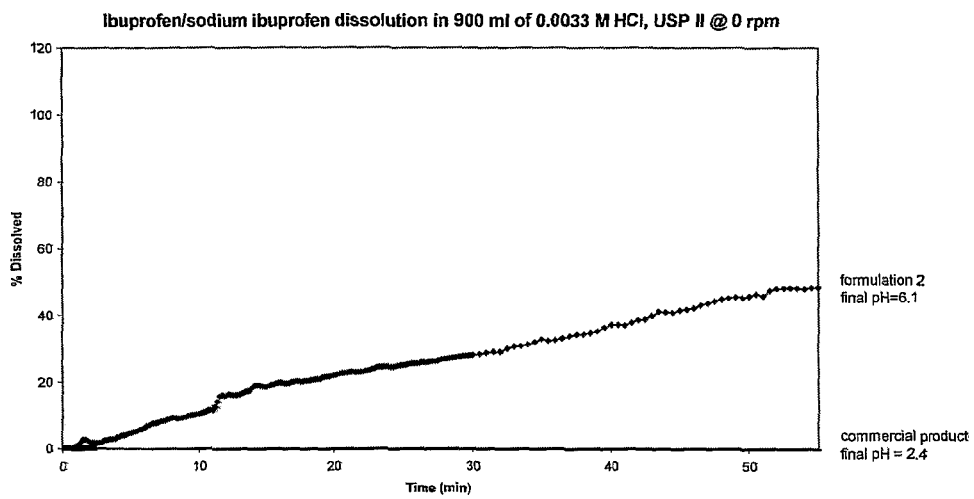
*Figure 12*    *Dissolution profiles for Ibuprofen in 900 mL 0.0033 M HCl at 0 rpm*
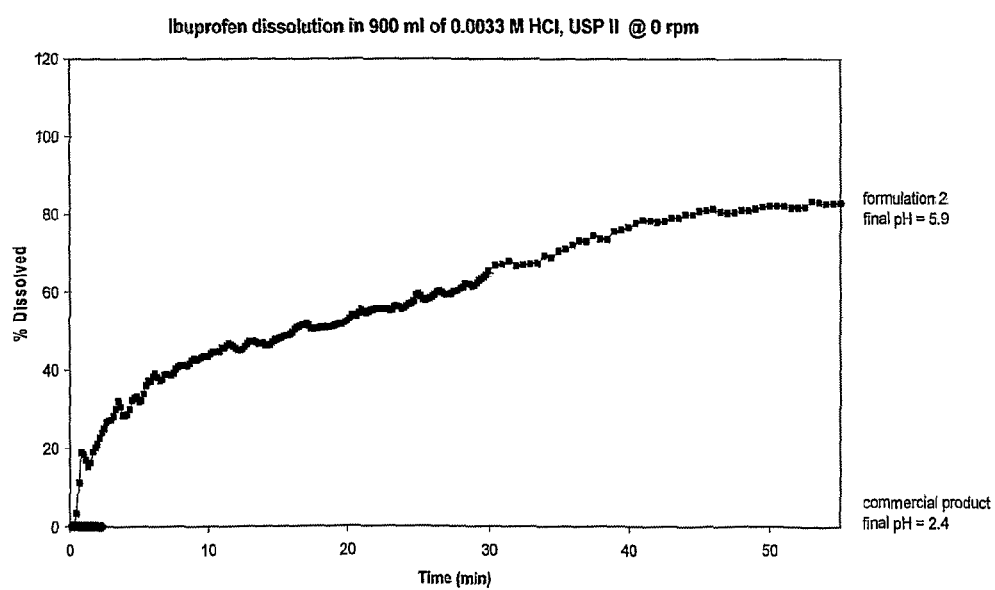

*Figure 13    Dissolution profiles for Diclofenac Potassium in 900 mL 0.0033 M HCl at 0 rpm*
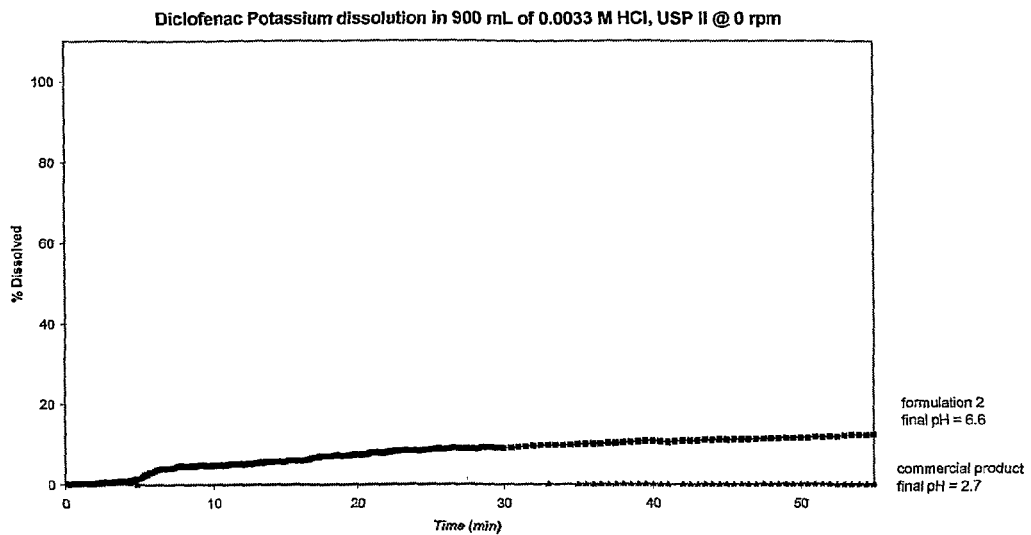
*Figure 14    Dissolution profiles for Paracetamol commercial products in 900 mL 0.0033 M HCl at 0 rpm*
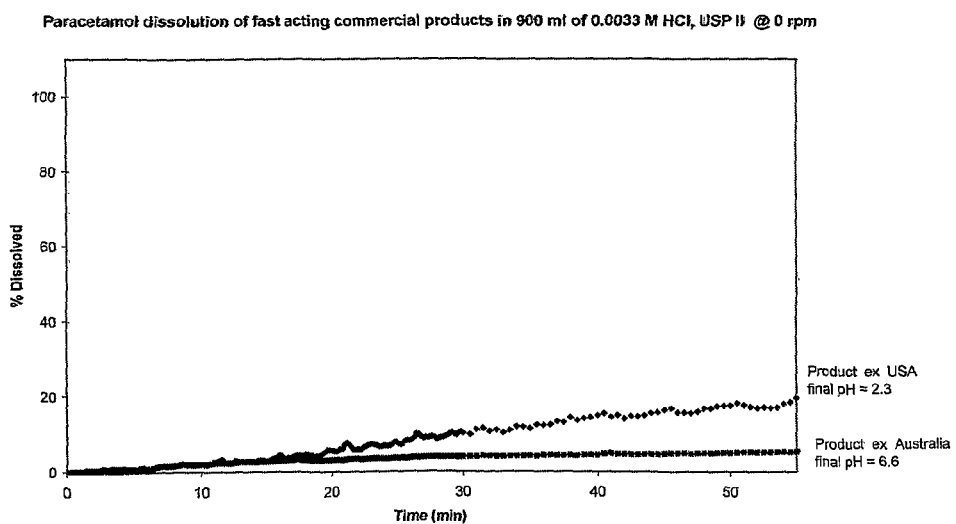

*Figure 15    Dissolution profiles for Paracetamol in 900 mL 0.0033 M HCl at 0 rpm*
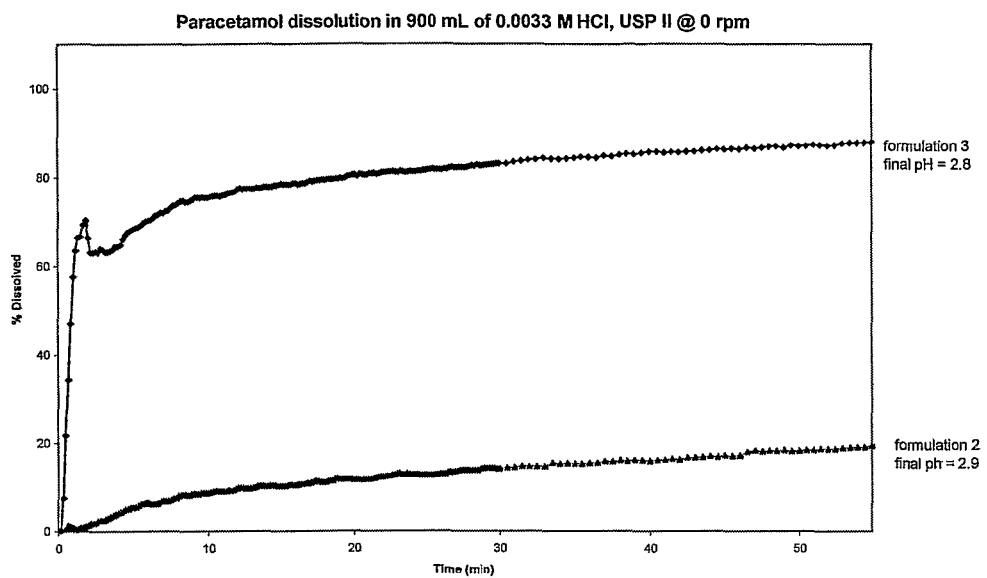
*Figure 16    Dissolution profiles for Naproxen in 900 mL 0.0033 M HCl at 0 rpm*
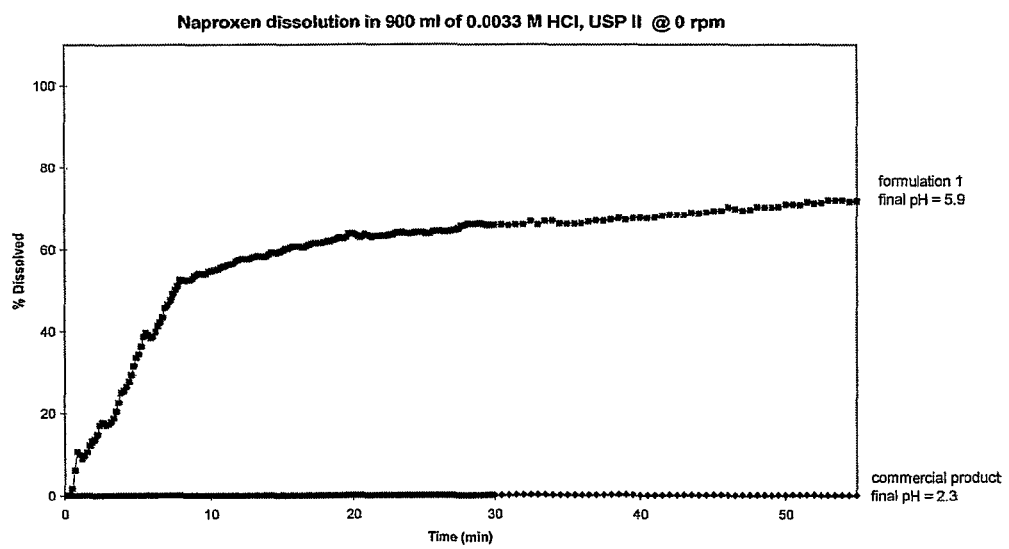

*Figure 17* *Dissolution profiles for Naproxen Sodium in 900 mL 0.0033 M HCl at 0 rpm*
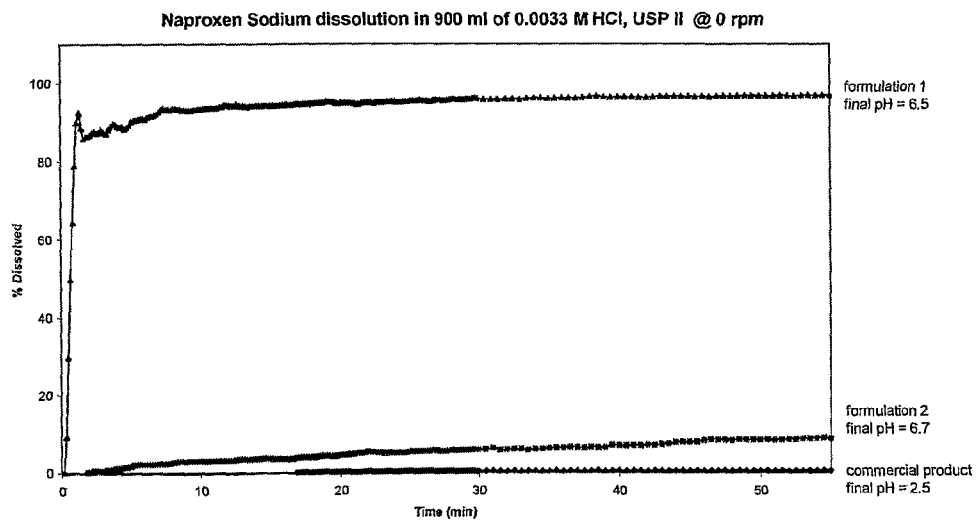
*Figure 18* *Dissolution profiles for Gemfibrozil in 900 mL 0.0033 M HCl at 0 rpm*
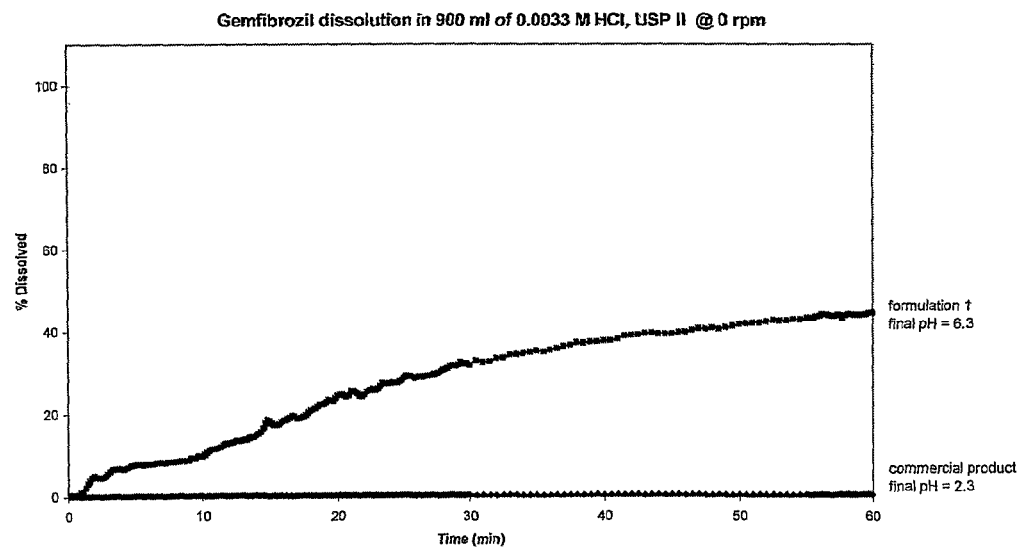

*Figure 19    Dissolution profiles for Furosemide in 900 mL 0.0033 M HCl at 0 rpm*
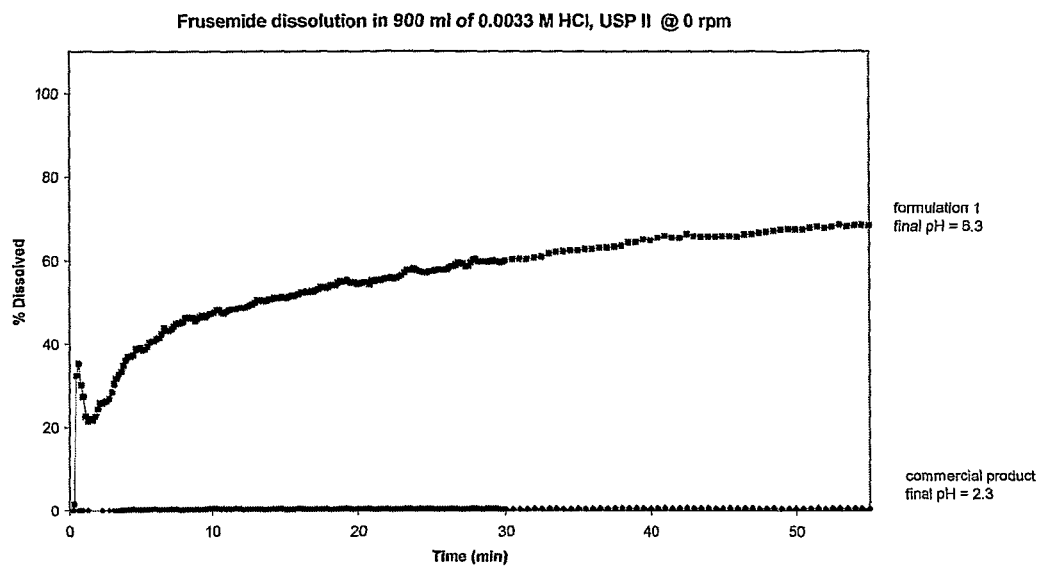
*Figure 20    Dissolution profiles for Temazepam in 900 mL 0.0033 M HCl at 0 rpm*
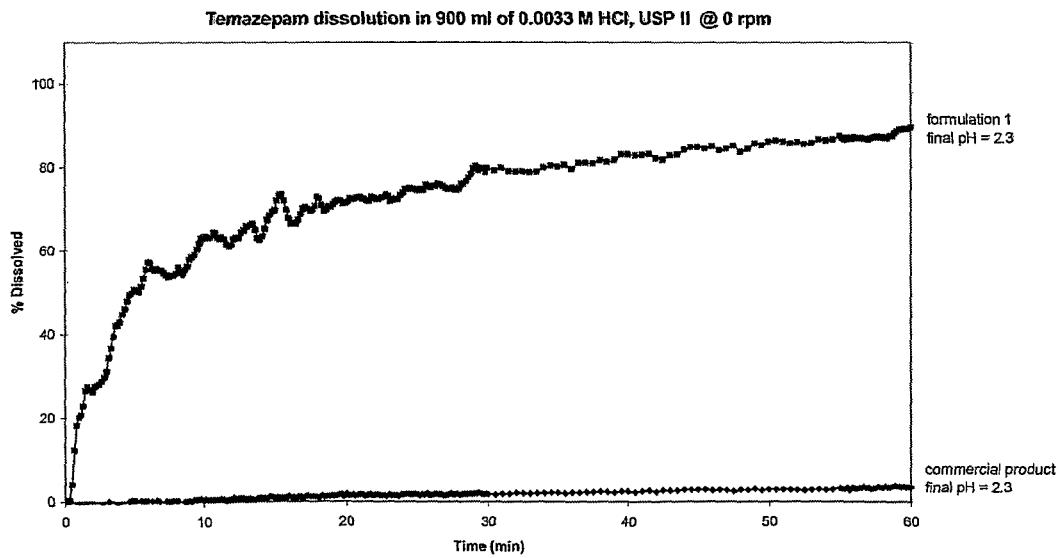

*Figure 21* Dissolution profiles for Montelukast Sodium in 900 mL 0.0033 M HCl at 0 rpm
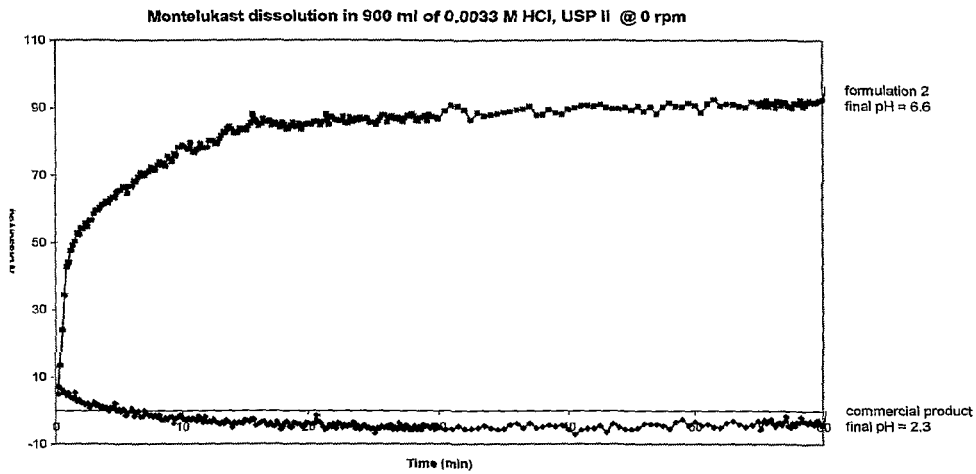
*Figure 22* Dissolution profiles for Prednisolone 5 mg in 900 mL 0.0033 M HCl at 30 rpm
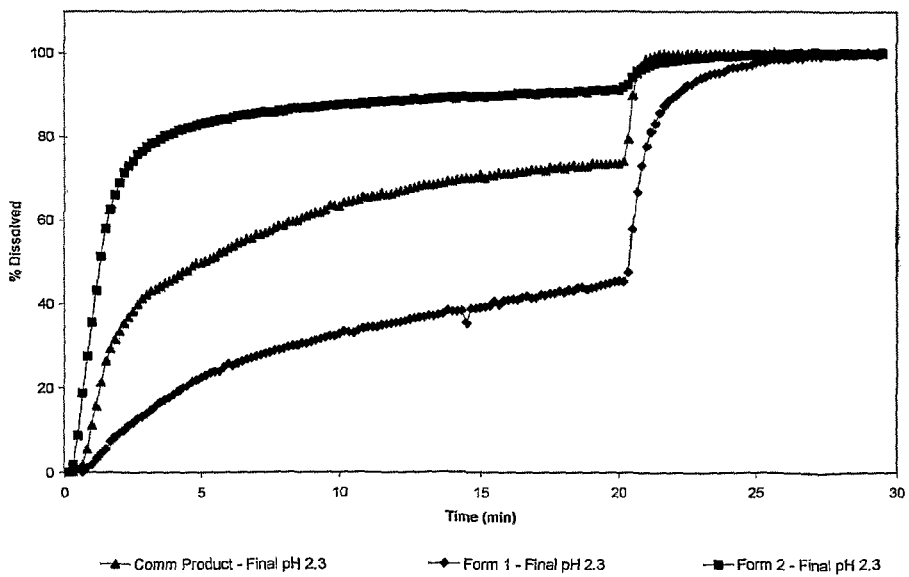

*Figure 23    Dissolution profiles for Prednisolone 25 mg in 900 mL 0.0033 M HCl at 30 rpm*
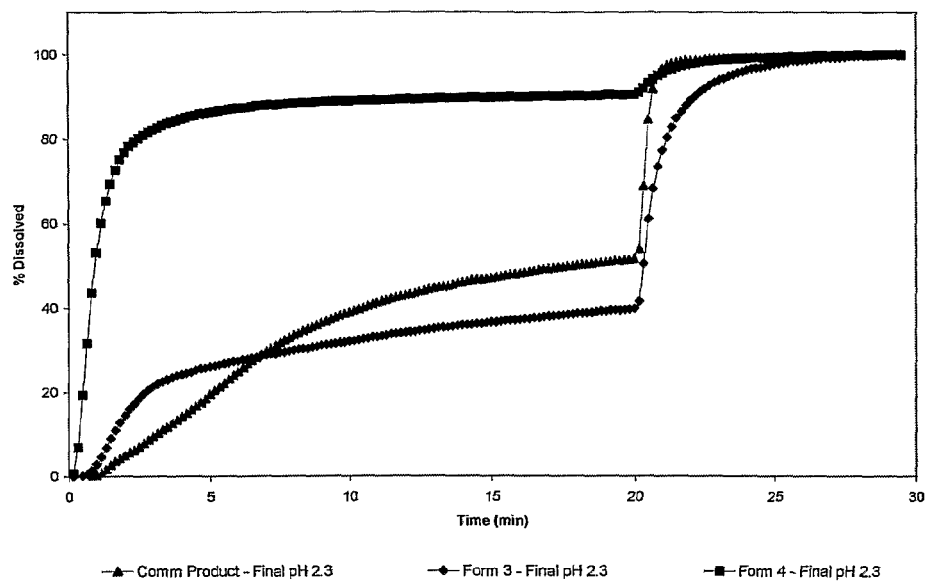
*Figure 24    Dissolution profiles for Prednisolone 5 mg in 900 mL 0.0033 M HCl at 0 rpm*
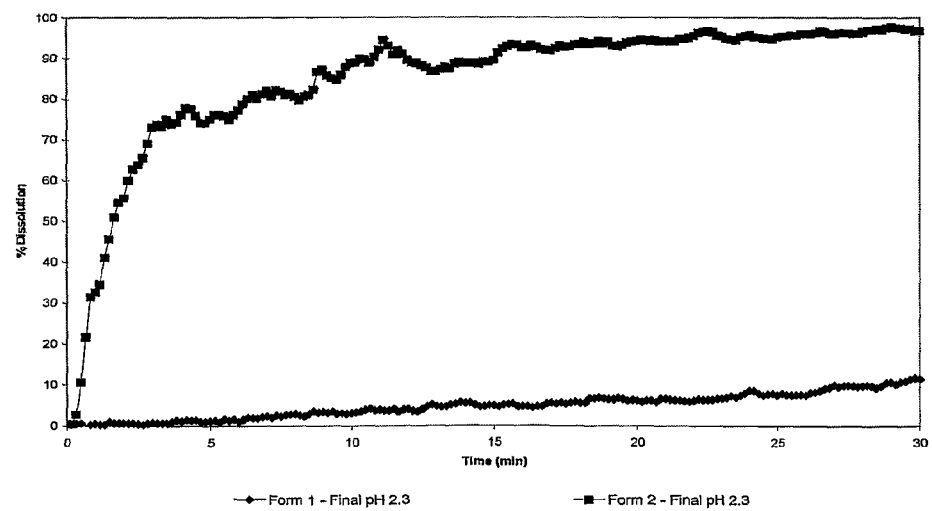

Figure 25   Dissolution profiles for Prednisolone 25 mg in 900 mL 0.0033 M HCl at 0 rpm
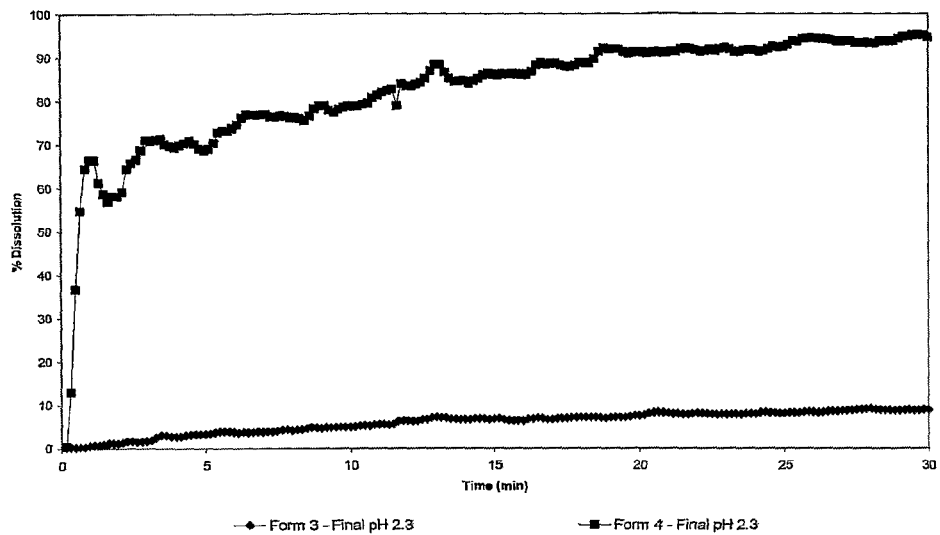
Figure 26   Dissolution profiles for Dexamethasone in 900 mL 0.0033 M HCl at 30 rpm
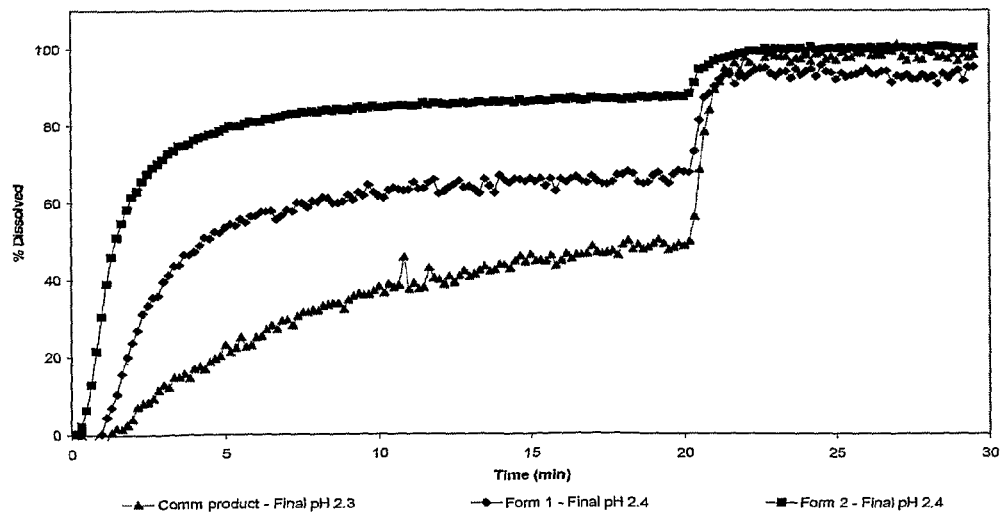

*Figure 27    Dissolution profiles for Dexamethasone in 900 mL 0.0033 M HCl at 0 rpm*
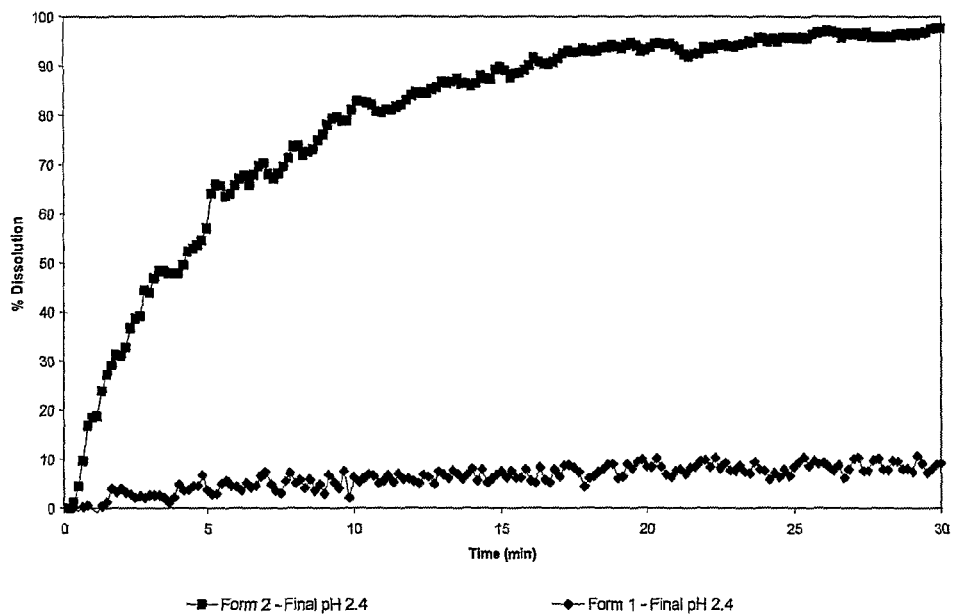
*Figure 28    Dissolution profiles for Fexofenadine Hydrochloride in 900 mL 0.0033 M HCl at 30 rpm*
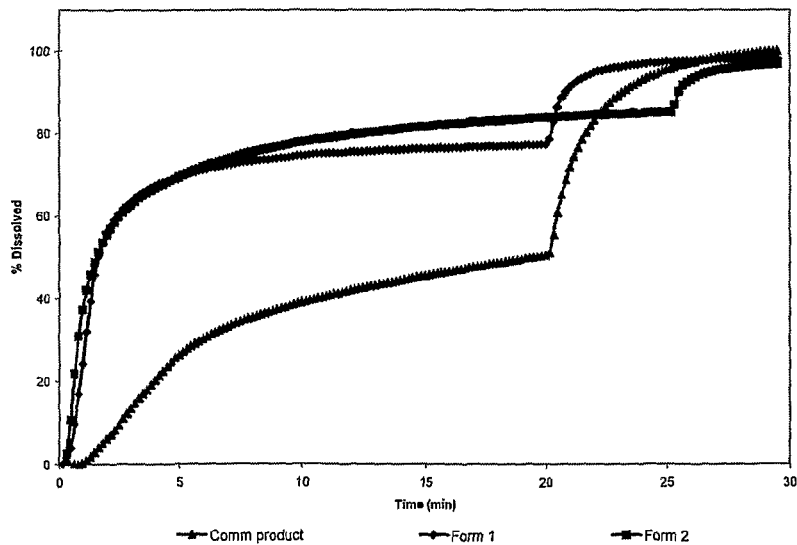

*Figure 29*  Dissolution profiles for Fexofenadine Hydrochloride in 900 mL 0.0033 M HCl at 0 rpm
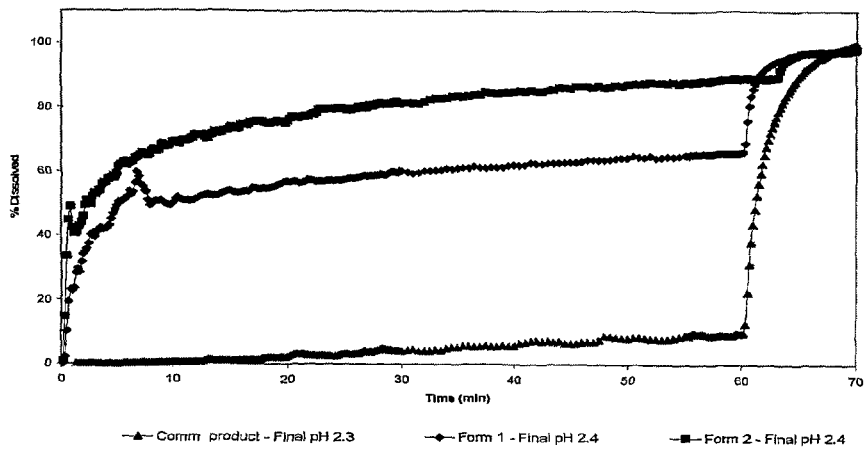
*Figure 30*  Dissolution profiles for Pseudoephedrine Hydrochloride in 900 mL 0.0033 M HCl at 30 rpm
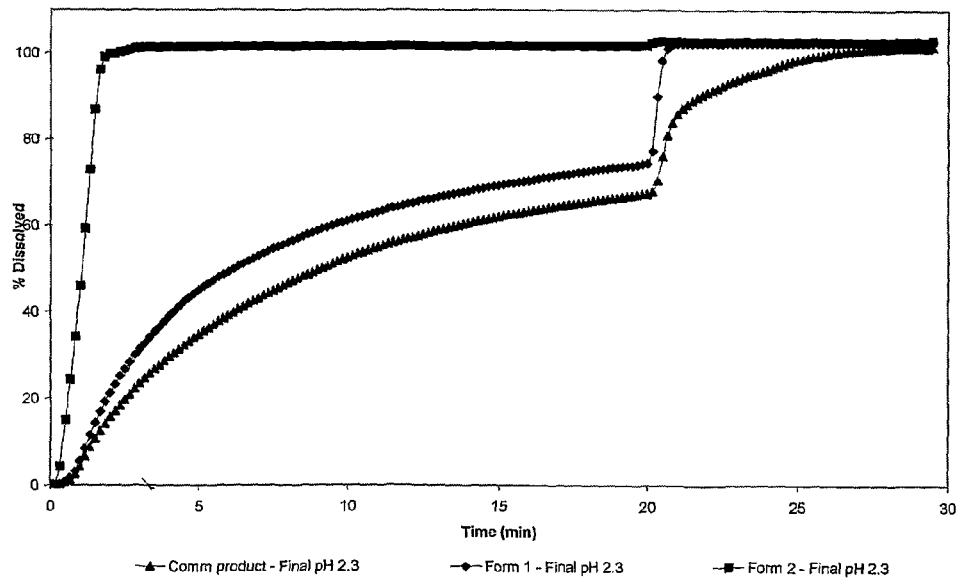

*Figure 31    Dissolution profiles for Pseudoephedrine Hydrochloride in 900 mL 0.0033 M HCl at 0 rpm*
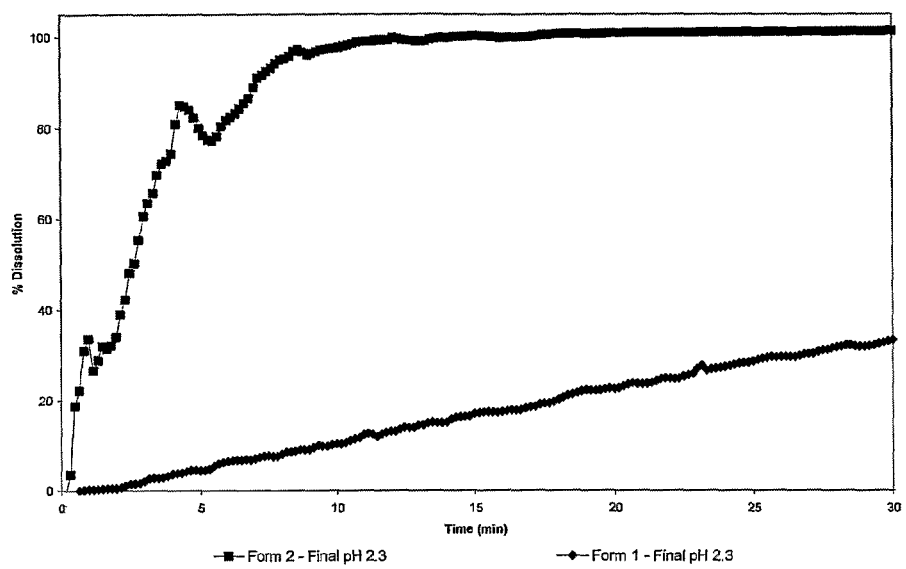
*Figure 32    Dissolution profiles for Eletriptan Hydrobromide in 900 mL 0.0033 M HCl at 30 rpm*
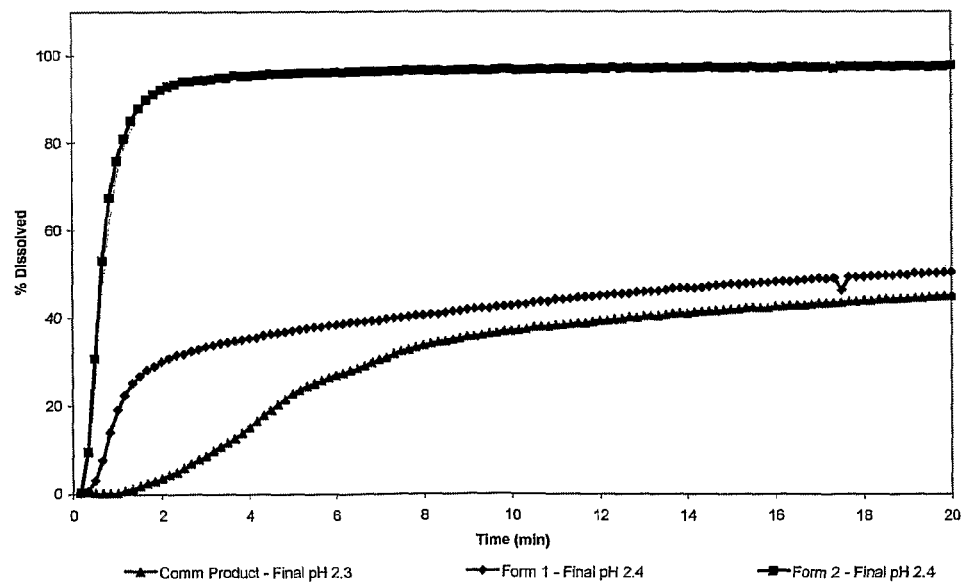

Figure 33   Dissolution profiles for Eletriptan Hydrobromide in 900 mL 0.0033 M HCl at 0 rpm
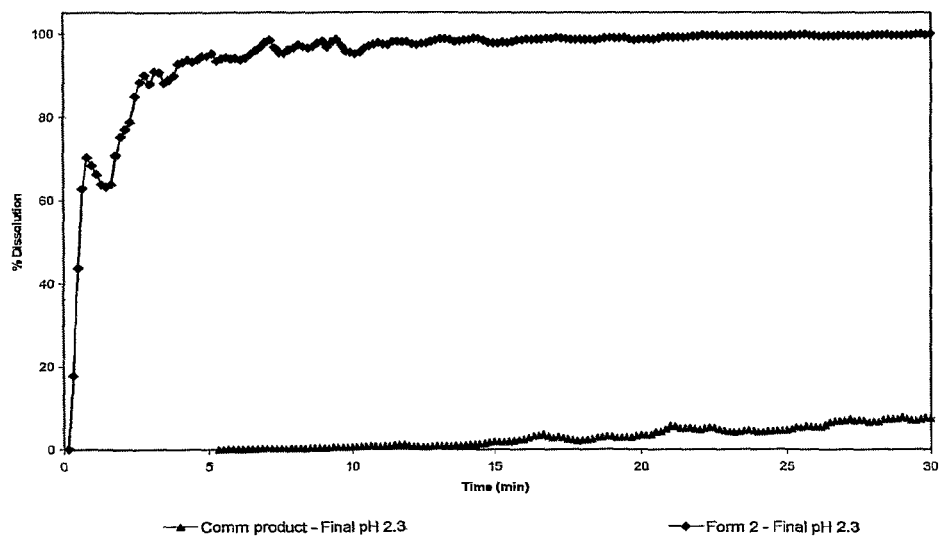
Figure 34   Dissolution profiles for Rizatriptan Benzoate in 900 mL 0.0033 M HCl at 30 rpm
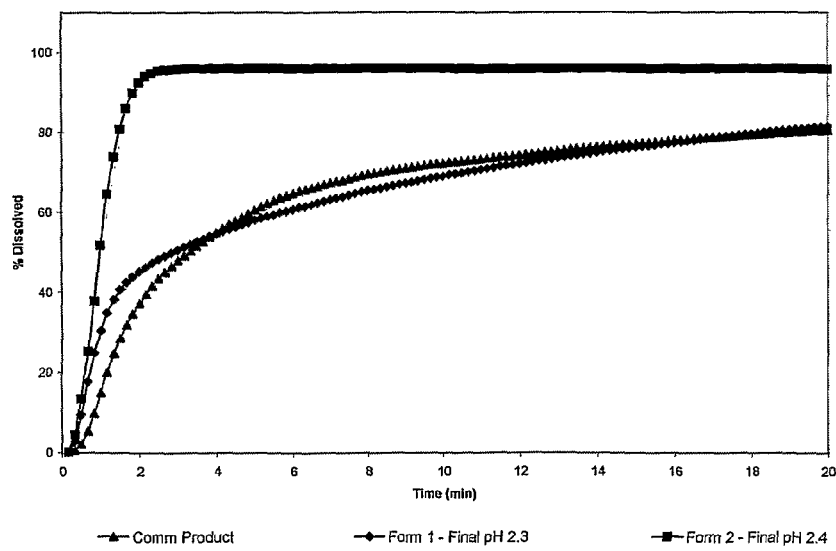

Figure 35   Dissolution profiles for Rizatriptan Benzoate in 900 mL 0.0033 M HCl at 0 rpm
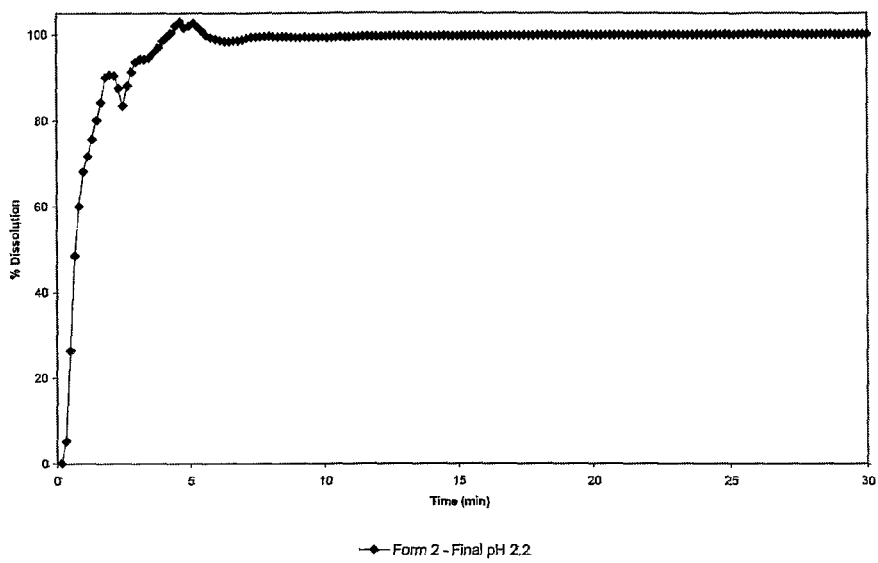
Figure 36   Dissolution profiles for Metoclopramide Hydrochloride in 900 mL 0.0033 M HCl at 30 rpm
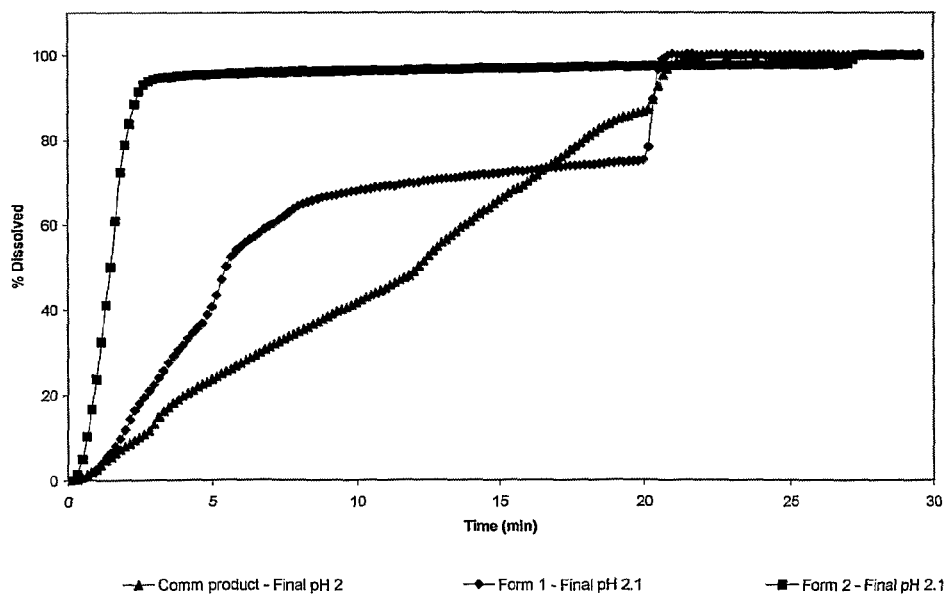

Figure 37  Dissolution profiles for Metoclopramide Hydrochloride in 900 mL 0.0033 M HCl at 0 rpm
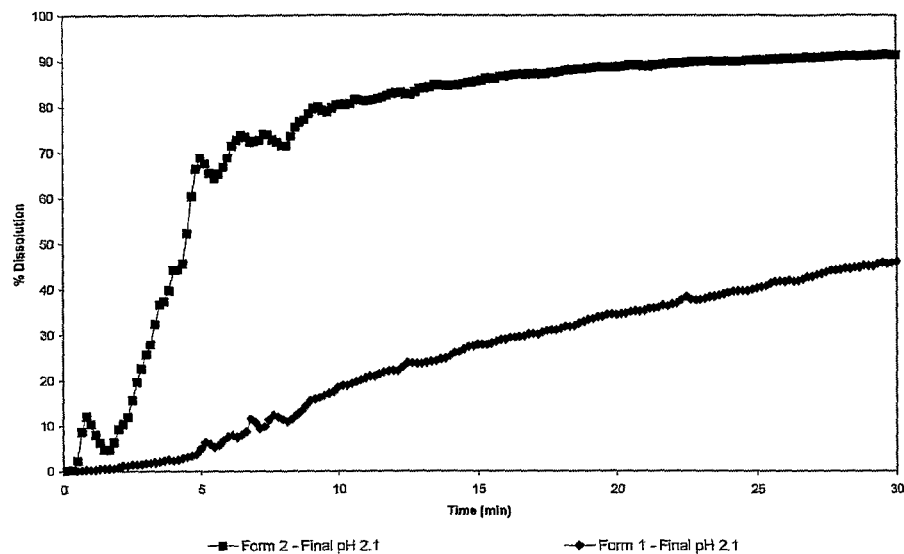
Figure 38  Dissolution profiles for Loperamide Hydrochloride in 900 mL 0.0033 M HCl at 30 rpm
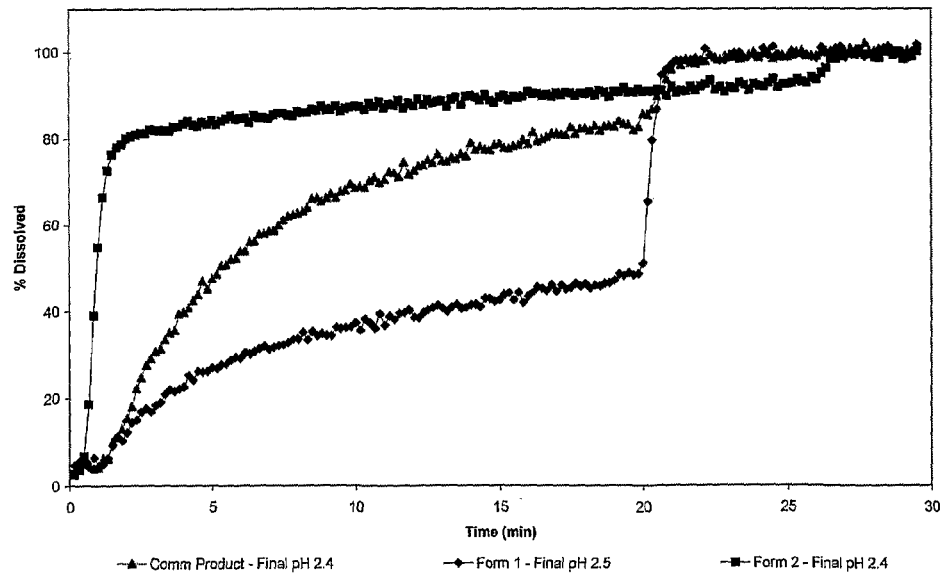

Figure 39  Dissolution profiles for Loperamide Hydrochloride in 900 mL 0.0033 M HCl at 0 rpm
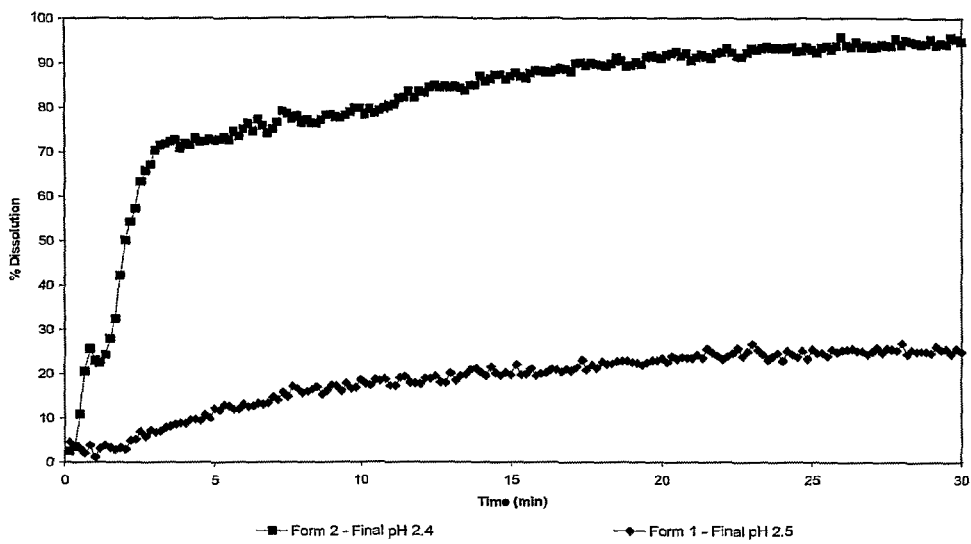
Figure 40  Dissolution profiles for Codeine Phosphate in 900 mL 0.0033 M HCl at 30 rpm
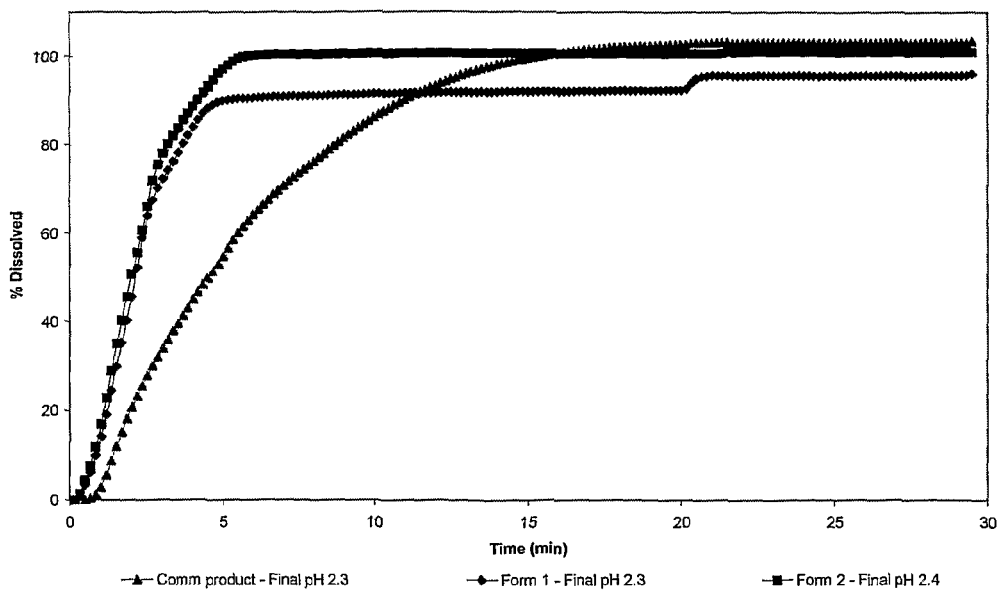

Figure 41  Dissolution profiles for Codeine Phosphate in 900 mL 0.0033 M HCl at 0 rpm
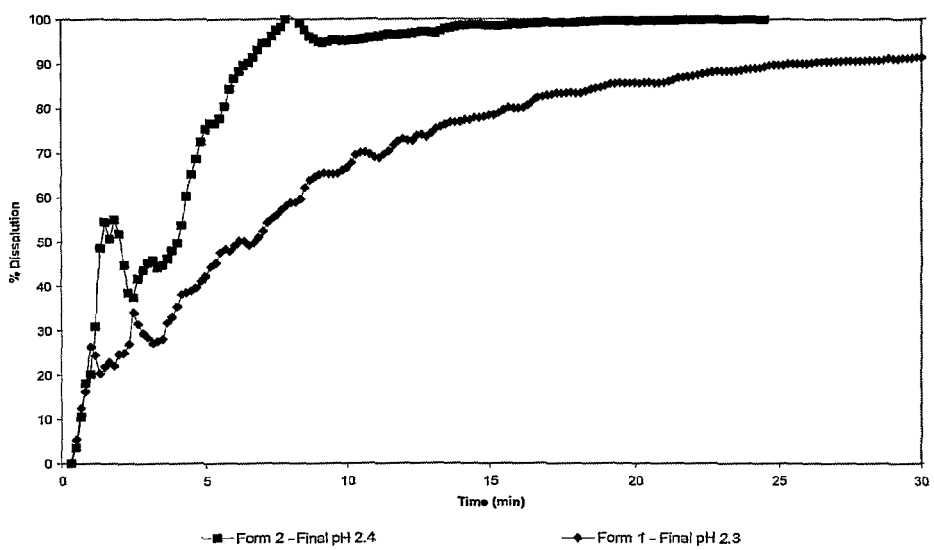
Figure 42  Dissolution profiles for Tramadol Hydrochloride in 900 mL 0.0033 M HCl at 30 rpm
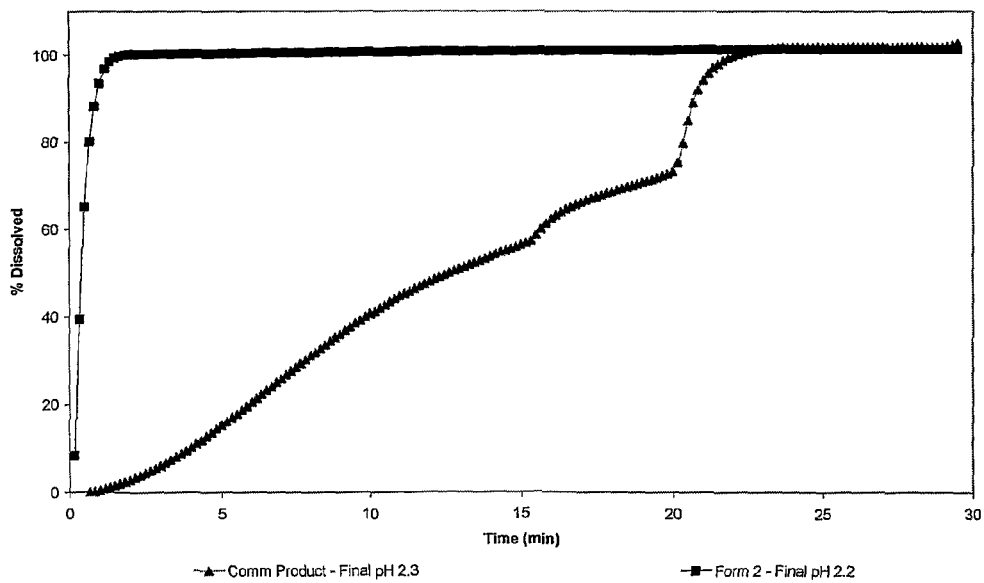

*Figure 43*     *Dissolution profiles for Tramadol Hydrochloride in 900 mL 0.0033 M HCl at 0 rpm*
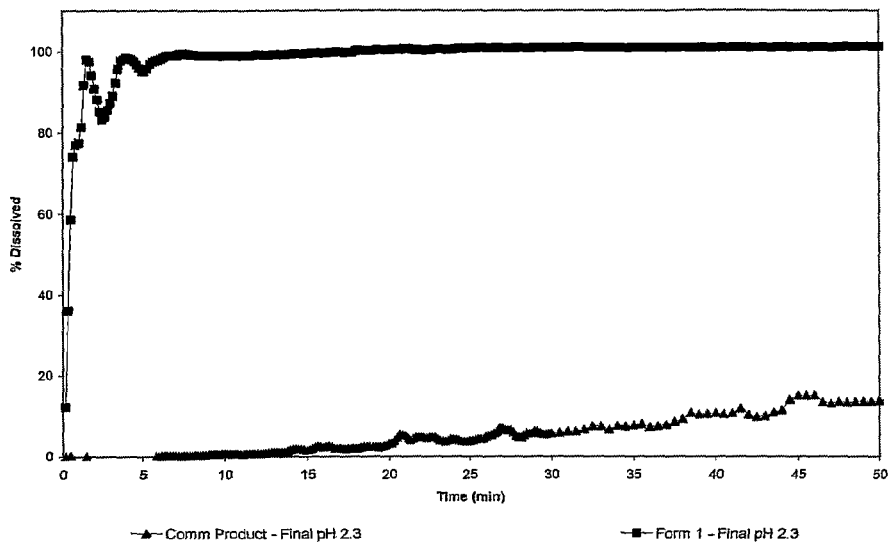
*Figure 44*     *Dissolution profiles for Diazepam in 900 mL 0.0033 M HCl at 30 rpm*
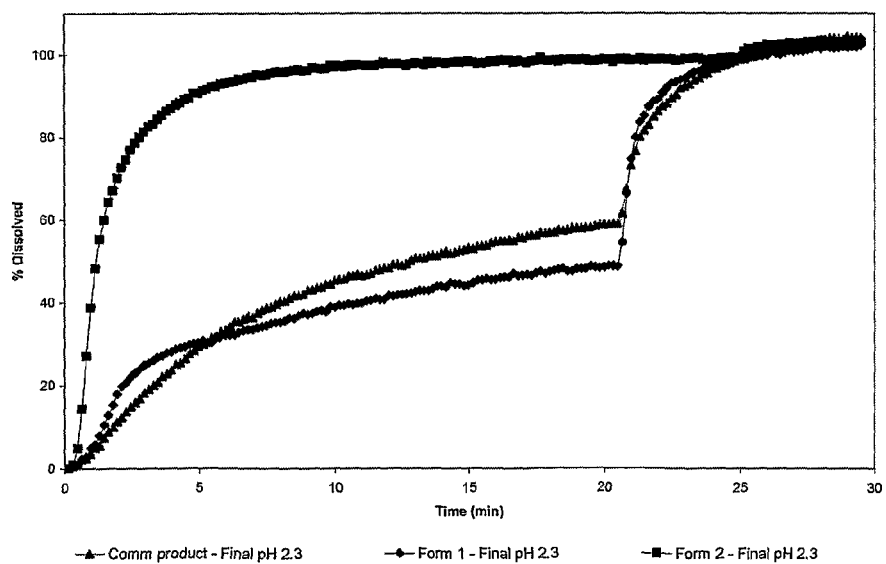

Figure 45  Dissolution profiles for Diazepam in 900 mL 0.0033 M HCl at 0 rpm
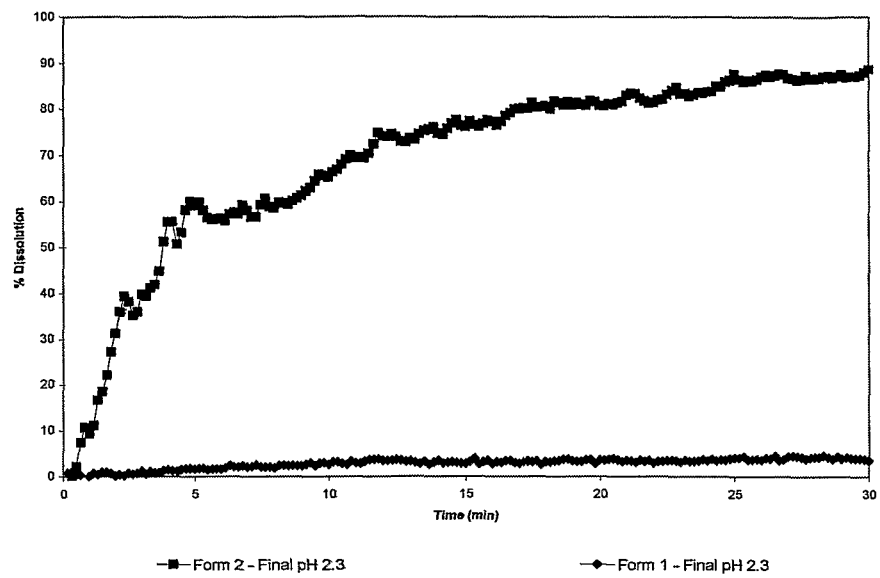
Figure 46  Dissolution profiles for Lorazepam in 900 mL 0.0033 M HCl at 30 rpm
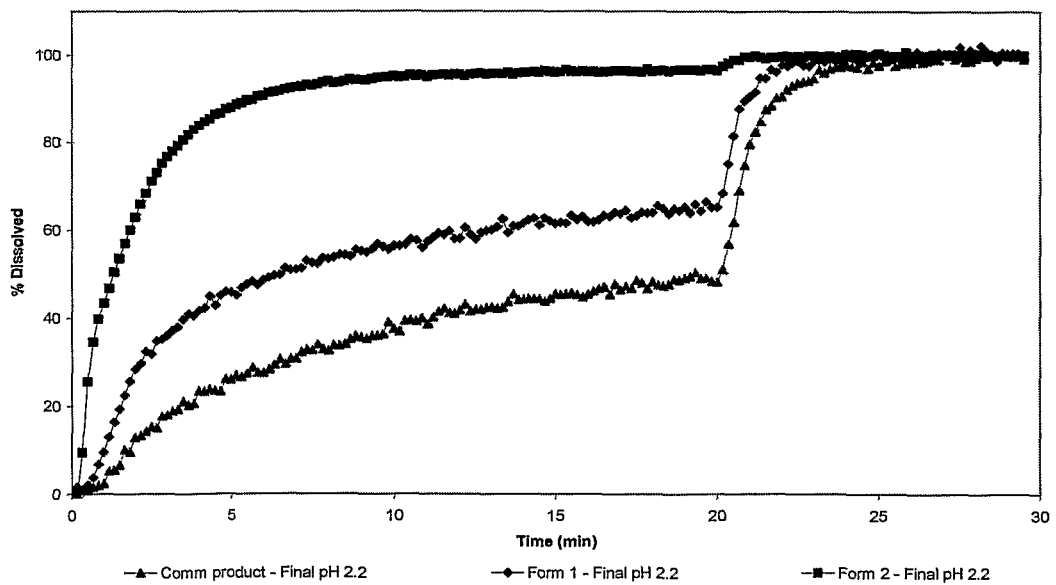

*Figure 47    Dissolution profiles for Lorazepam in 900 mL 0.0033 M HCl at 0 rpm*
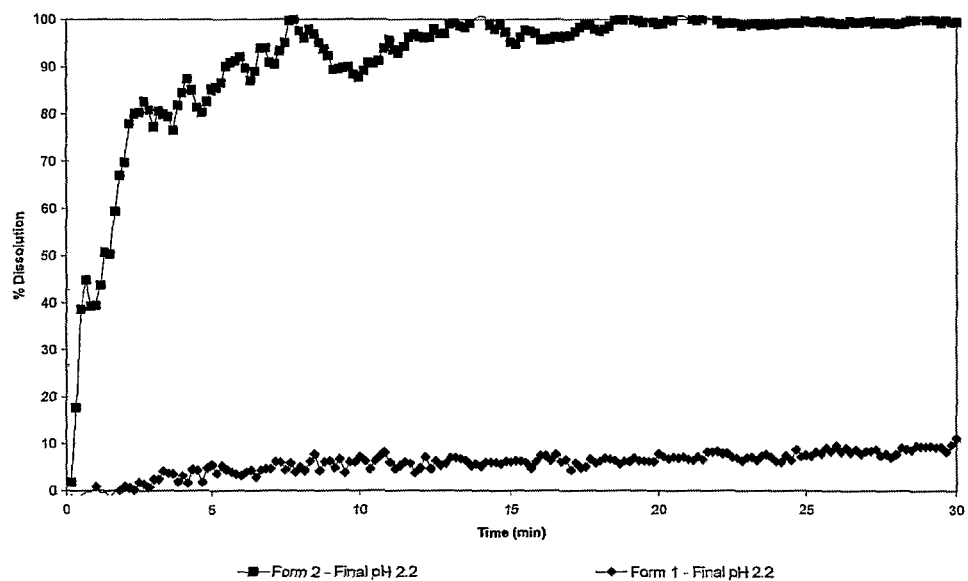
*Figure 48    Dissolution profiles for Alprazolam in 900 mL 0.0033 M HCl at 30 rpm*
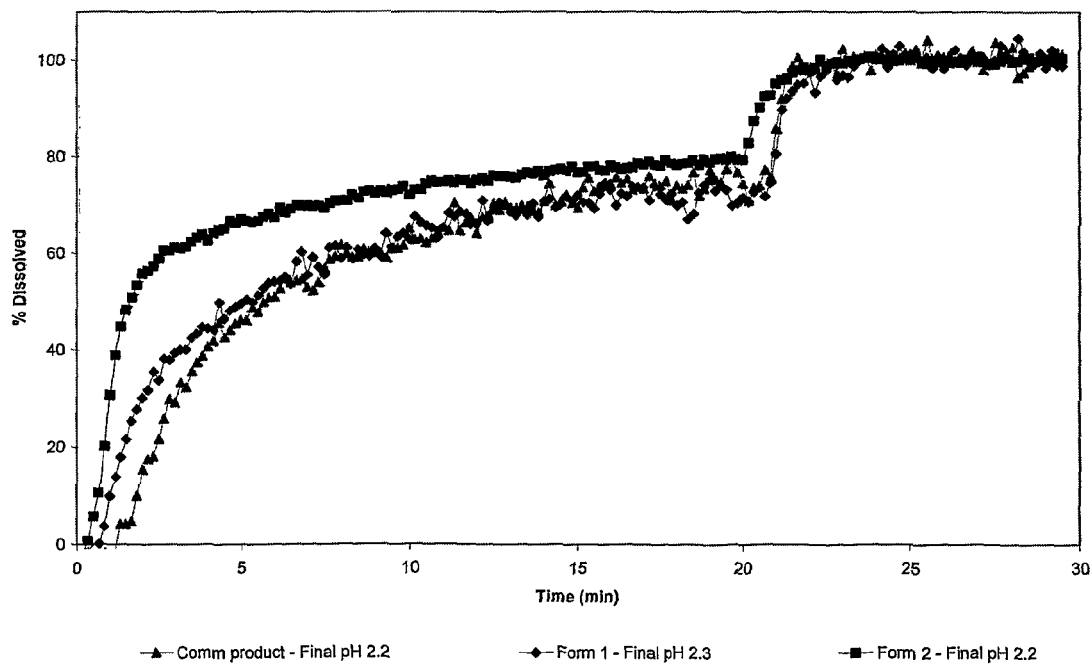

*Figure 49    Dissolution profiles for Alprazolam in 900 mL 0.0033 M HCl at 0 rpm*
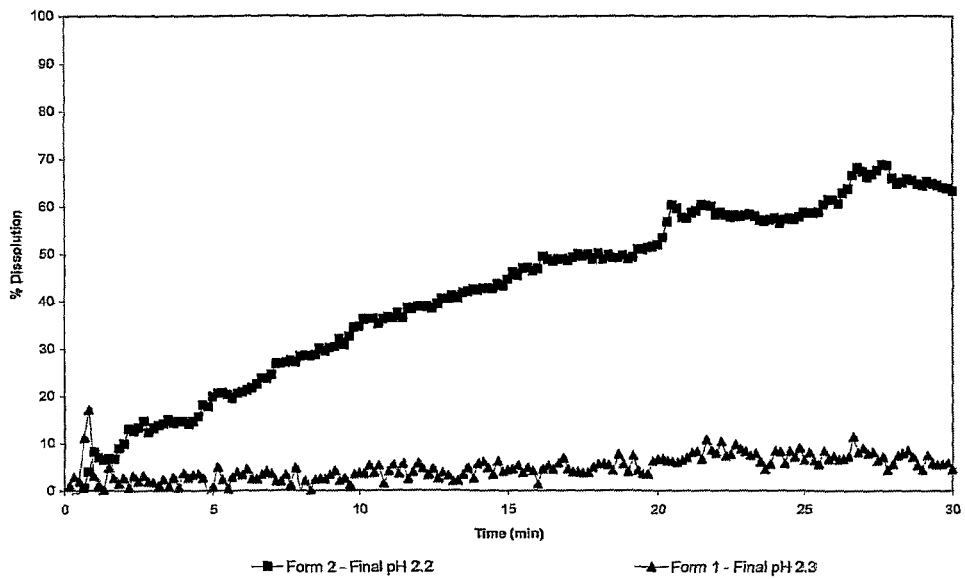
*Figure 50    Dissolution profiles for Sildenafil Citrate in 900 mL 0.0033 M HCl at 30 rpm*
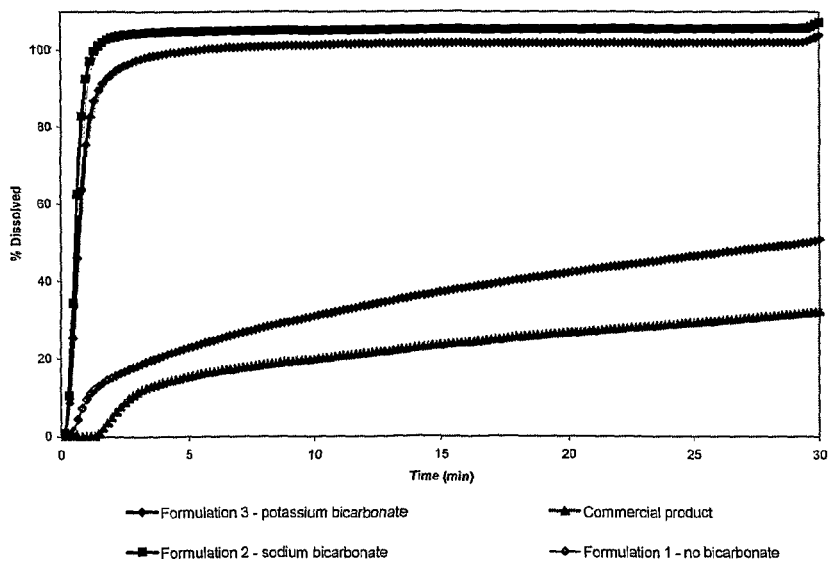

*Figure 51*   Dissolution profiles for Sildenafil Citrate in 900 mL 0.0033 M HCl at 0 rpm
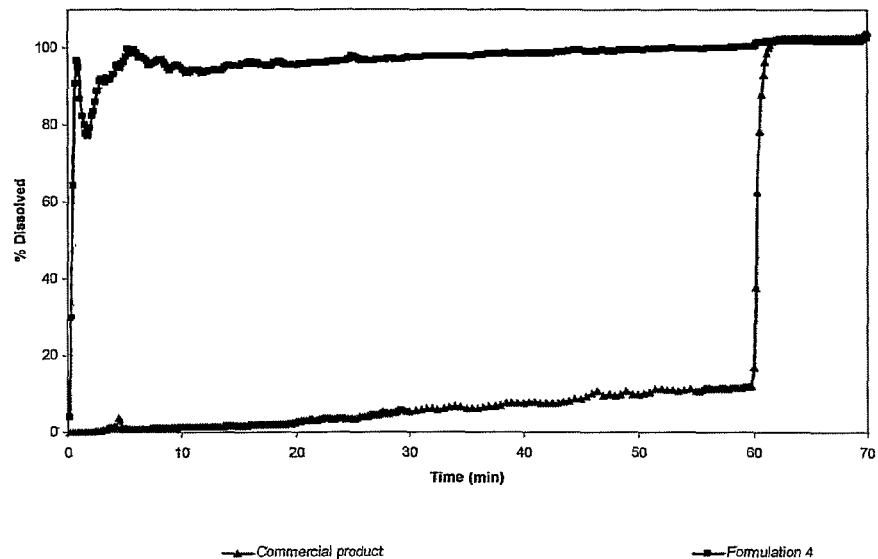
*Figure 52*   Dissolution profiles for Ondansetron Hydrochloride in 900 mL 0.0033 M HCl at 30 rpm
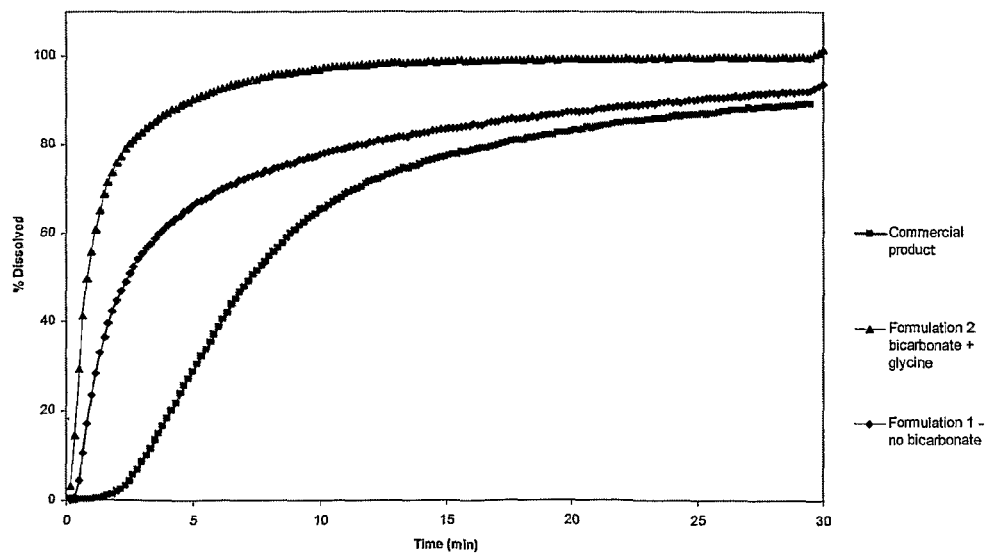

Figure 53  Dissolution profiles for Ondansetron Hydrochloride in 900 mL 0.0033 M HCl at 0 rpm
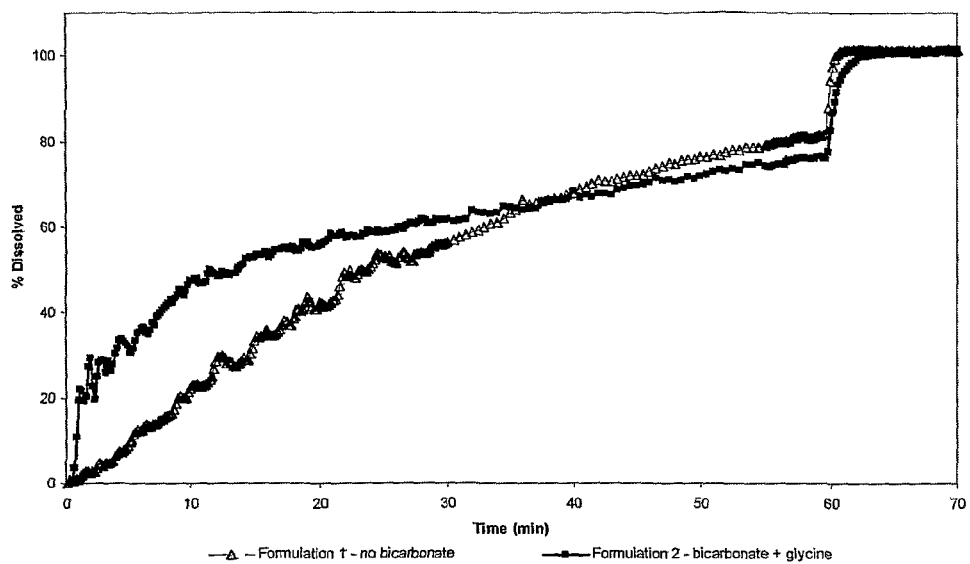
Figure 54  Dissolution profiles for Zolmitriptan in 900 mL 0.0033 M HCl at 30 rpm
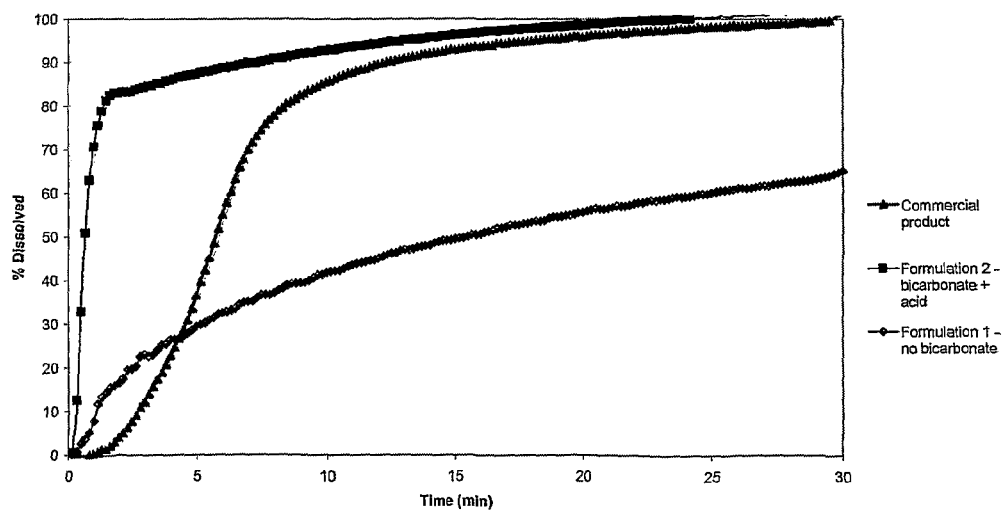

Figure 55    Dissolution profiles for Zolmitriptan in 900 mL 0.0033 M HCl at 0 rpm
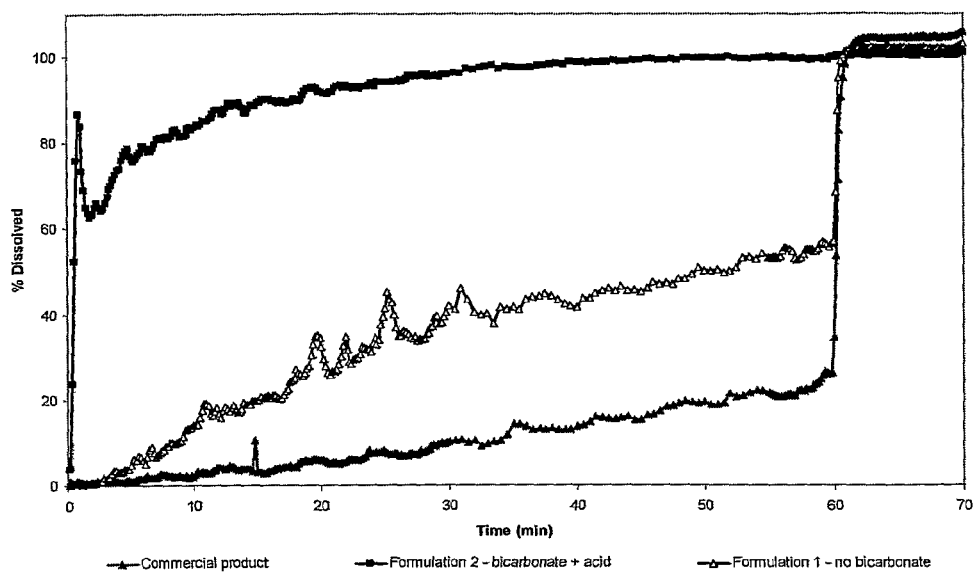
Figure 56    Dissolution profiles for Zolpidem Tartrate in 900 mL 0.0033 M HCl at 30 rpm
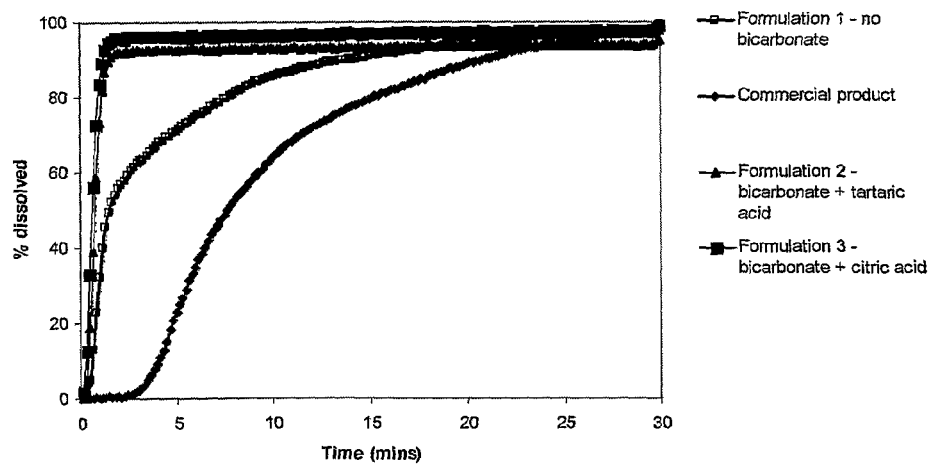

*Figure 57  Dissolution profiles for Zolpidem Tartrate in 900 mL 0.0033 M HCl at 0 rpm*
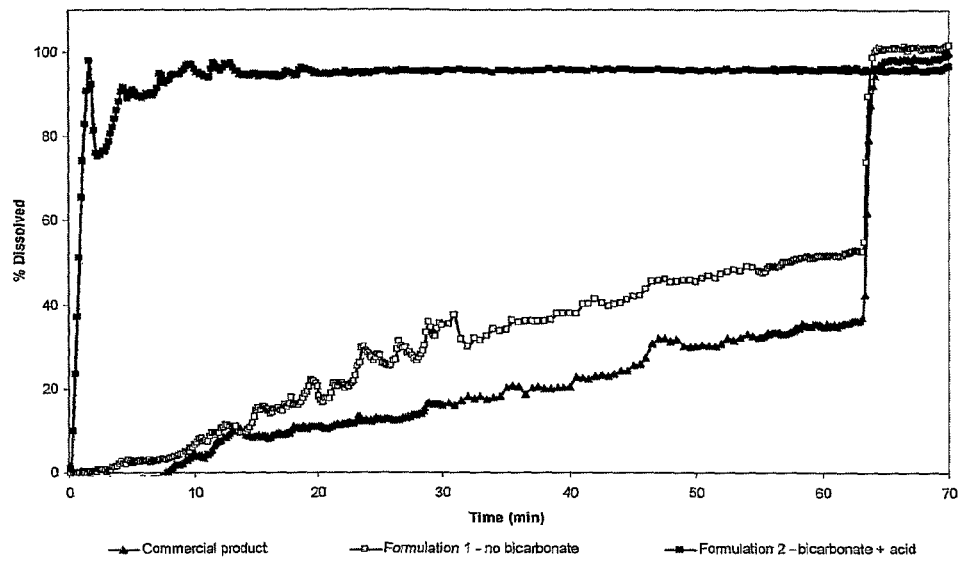
*Figure 58  Dissolution profiles for Cetirizine Dihydrochloride in 900 mL 0.0033 M HCl at 30 rpm*
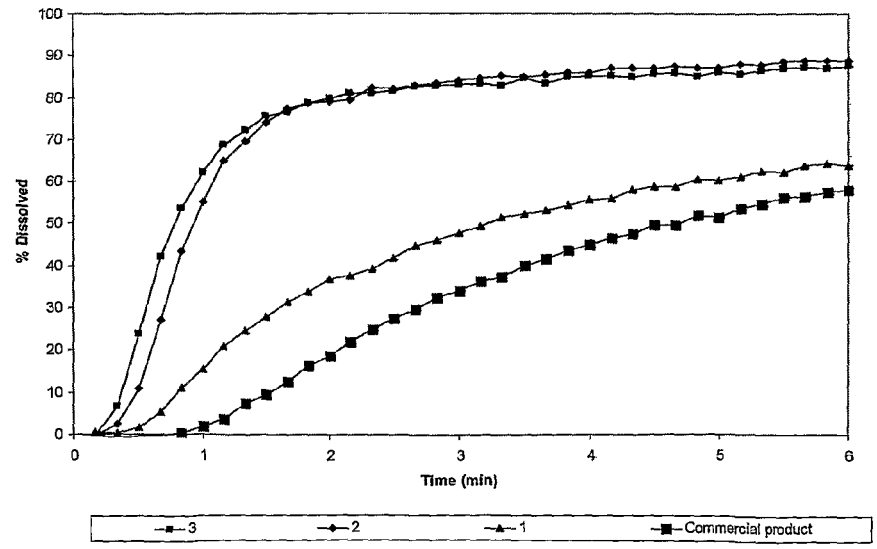

Figure 59  Dissolution profiles for Cetirizine Dihydrochloride in 900 mL 0.0033 M HCl at 0 rpm
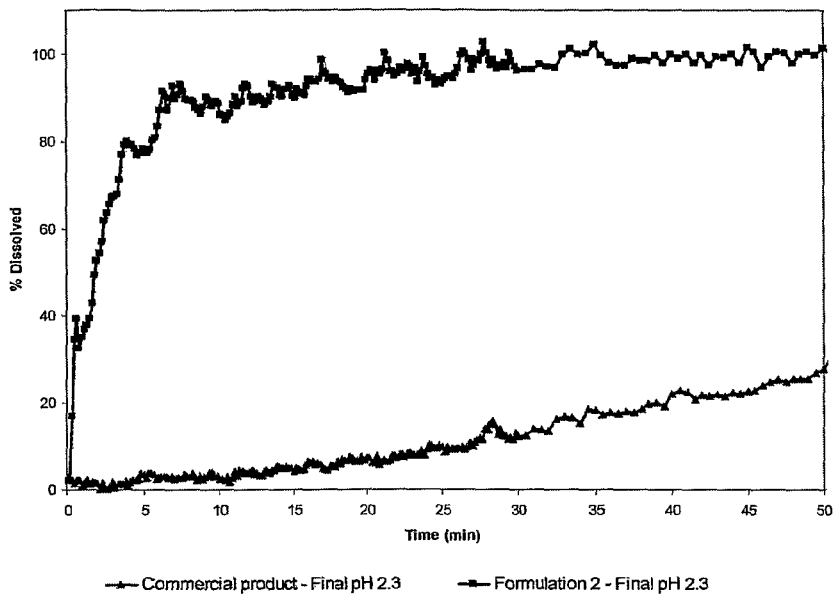
Figure 60  Dissolution profiles for Paracetamol in 900 mL 0.0033 M HCl at 30 rpm comparing two wet granulated formulations with two fast acting commercial products
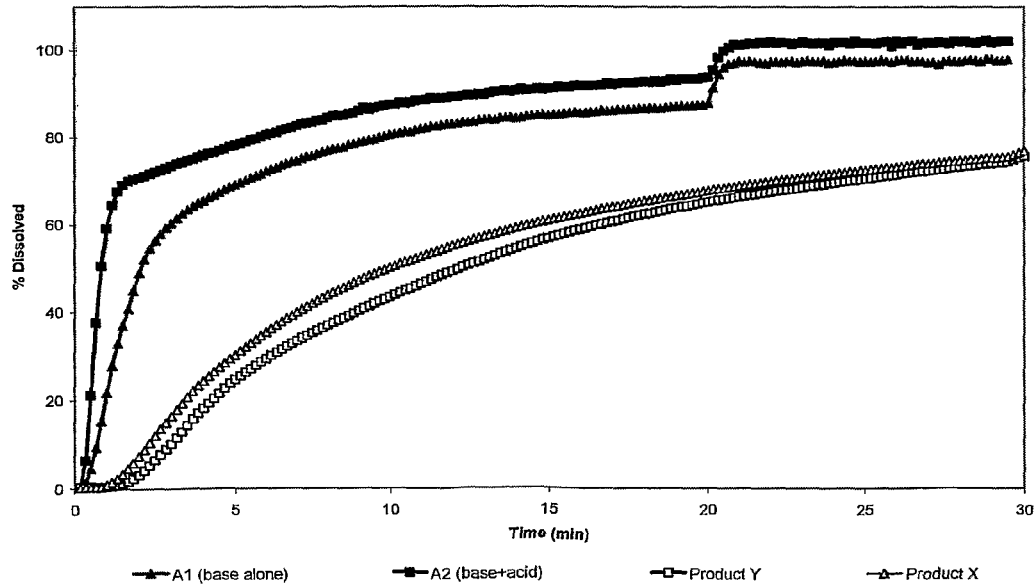

Figure 61  Dissolution profiles for Paracetamol in 900 mL 0.0033 M HCl at 0 rpm comparing two wet granulated formulations with two fast acting commercial products
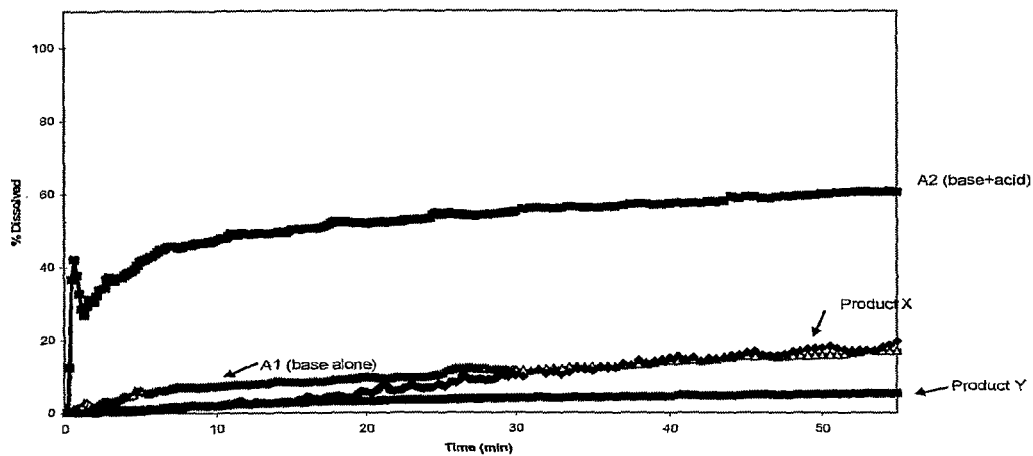
Figure 62  Dissolution profiles for Paracetamol and Tramadol Hydrochloride in 900 mL 0.0033 M HCl at 30 rpm
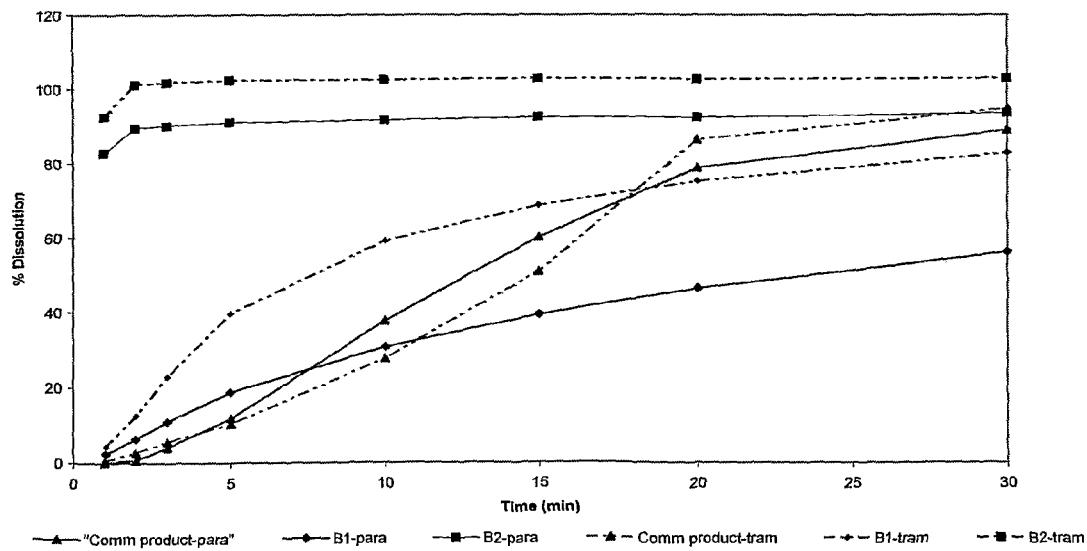

Figure 63   Dissolution profiles for Paracetamol and Tramadol Hydrochloride in 900 mL 0.0033 M HCl at 0 rpm
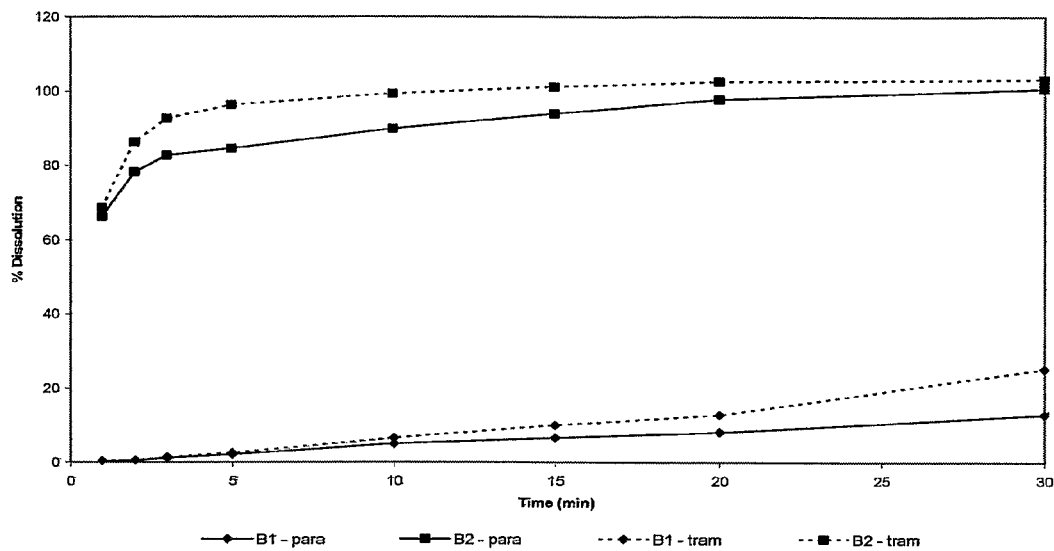
Figure 64   Dissolution of Ibuprofen formulations in 200 mL water at 30 rpm
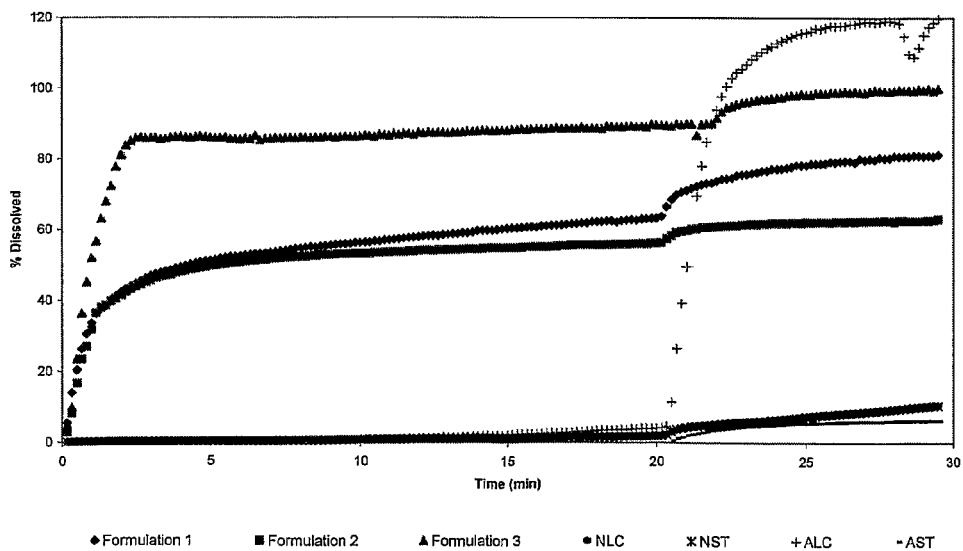

Figure 65   Dissolution of Paracetamol formulations in 200 mL full cream milk at 30 rpm and 37 °C
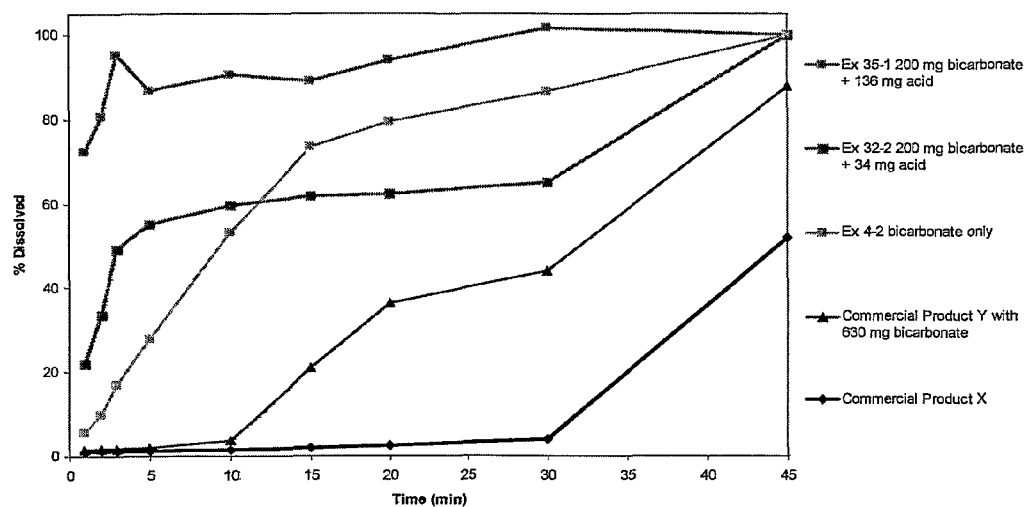
Figure 66   Dissolution of Zolpidem Tartrate formulations in 200 mL full cream milk, 0.0033 N HCl and 0.015 N HCl at 30 rpm and 37 °C
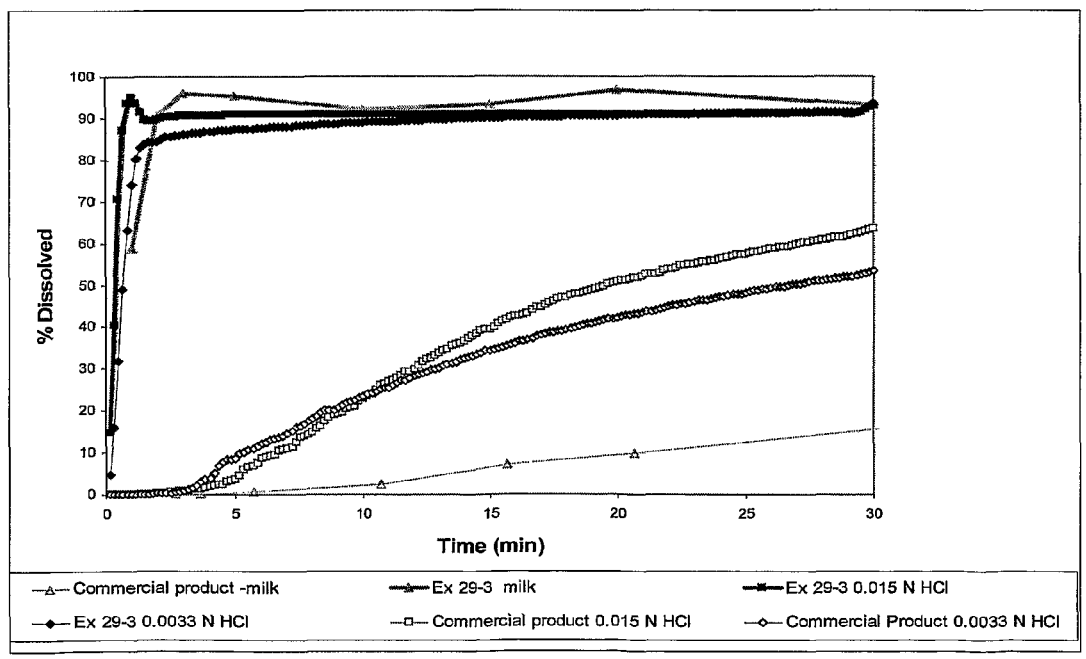

ORAL THERAPEUTIC COMPOUND DELIVERY SYSTEM

FIELD OF THE INVENTION

The present invention relates generally to therapeutic formulations. More particularly, this present invention provides an oral delivery system for a therapeutic compound that is an acid, base, amphoteric or unionized compound or a salt thereof with pharmacological, physiological or biochemical activity or a proactive form thereof. The present invention even more particularly provides rapid dissolution of a swallow formulation comprising a therapeutic compound that is an acid, base, amphoteric or unionized compound or a salt thereof which facilitates the rapid delivery of the therapeutic compound to the circulatory system.

BACKGROUND OF THE INVENTION

In this specification where a document, act or item of knowledge is referred to or discussed, this reference or discussion is not an admission that the document, act or item of knowledge or any combination thereof was at the priority date publicly available, known to the public, part of the common general knowledge or known to be relevant to an attempt to solve any problem with which this specification is concerned.

Improving the rate and extent of absorption of oral formulations of compounds has been the subject of substantial research. In general, once an immediate release solid swallow composition reaches the stomach, it undergoes disintegration and/or dissolution and passes into the small intestine where the active ingredient is absorbed across intestinal walls into the circulatory system via the portal vein and liver before reaching the site of action. For drugs where absorption is not rate limited, fast disintegration and fast dissolution of the active ingredient should promote fast absorption in vivo.

Solid dosage forms for oral administration can be categorized into three major groups. Those described as swallow formulations are intended to be swallowed whole. Those described as orally disintegrating or orally dissolving or chewable, are intended to be dispersed or dissolved in the mouth before swallowing. The third group is generally called dispersible or soluble formulations that are intended to be dissolved or dispersed in liquid before administration, such that the patient swallows the resultant solution or dispersion.

Of the group of swallow formulations, some are designed for sustained or delayed release through the use of coatings or other devices that control the site of release of the drug within the gastrointestinal tract. Examples include enteric coated tablets to avoid the local gastric toxicity which occurs with some acidic drugs such as the Non-Steroidal Anti-Inflammatory Drugs (NSAIDs), and controlled or multi-phase release of drugs to allow once daily dosage.

Other swallow formulations may be designed for immediate release providing fast dissolution of the active ingredient, with the aim of achieving fast absorption and fast onset of action.

This present invention relates to formulations manufactured as immediate release solid dosage forms intended to be swallowed intact, which will achieve fast dissolution with fast absorption of the active ingredient.

The use of sodium bicarbonate and other alkali metal carbonates has been described for a number of different purposes in pharmaceutical dosage forms containing a variety of different actives.

Soluble or Dispersible Effervescent Formulations

The use of sodium bicarbonate and other alkali metal carbonates, as the base component of an effervescent couple in dosage forms intended for dissolution or dispersion in water prior to administration, is widely recognised. Typically the resultant effervescent solutions or dispersions exhibit fast absorption of the drug contained therein.

Such formulations generally contain effervescent couples such as citric acid and sodium bicarbonate in large amounts. For example, U.S. Pat. No. 6,245,353 (Tritthart et al) describes a tablet containing cetirizine with an effervescent couple for disintegration in water prior to administration. A variety of effervescent formulations which are intended to be dispersed and/or dissolved prior to administration are disclosed for example in U.S. Pat. No. 4,704,269 (Korab et al), U.S. Pat. No. 4,309,408 (Pathak et al) and U.S. Pat. No. 4,942,039 (Duvall et al).

US Patent Application 20050147671 (Reiner at al) describes a fast absorbing formulation of diclofenac and one or more alkali metal carbonates or bicarbonates in small amounts. This disclosure predominantly relates to effervescent powder formulations added to water before administration.

U.S. Pat. No. 4,834,966 (Gazzaninga et al) describes granulates which are completely dissolved in water and administered as an aqueous solution which results in reduced time to reach peak plasma concentration. The granules containing arginine, ibuprofen and sodium bicarbonate reportedly provide enhanced dissolution of ibuprofen in water.

The purpose of the present invention is to incorporate the advantages of improved absorption and reproducibility of dispersible and/or soluble formulations into swallow formulations that are more convenient, and remain the preferred dosage form for many patients, particularly for regular use.

Disintegration

In swallow formulations, the use of bicarbonates has been described to act as a disintegrant through the production of gaseous carbon dioxide when the base reacts with acid.

U.S. Pat. No. 5,681,583 (Conte et al) uses agents such as sodium bicarbonate in one layer of a multi-layered controlled-release swallow tablet. The sodium bicarbonate effervesces in contact with acid solutions achieving fast disintegration and dissolution of the drug into water and the intestinal fluid.

U.S. Pat. No. 6,197,336 (Grassano et al) describes a swallow formulation containing a ternary mixture of ibuprofen with arginine and linear PVP which, when blended with other ingredients including 5-10% sodium bicarbonate (15-40 mg) with respect to ibuprofen, is readily compressible and achieves complete dissolution in pH 7.2 phosphate buffer in 10 minutes.

US Patent Application 20020034540 (Price et al) describes a compressed dosage form containing at least 35% by weight ibuprofen with sufficient alkali metal carbonate or bicarbonate in the range 5-15% of the tablet weight, such that the crushing strength of the tablet is 6.5-15 Kp and the disintegration time is less than 10 minutes. This discloses the use of alkali metal carbonates as a disintegrant in the range 25-75 mg per tablet.

These disclosures describe relatively low concentrations of alkali metal carbonates that will not increase the pH and hence will not increase the solubility of acidic drugs.

Taste Masking

A different application of bicarbonates is their use to improve the taste and palatability of orally dispersible or soluble dosage forms of some drugs.

This benefit of bicarbonates is noted by Reiner et al in US Patent Applications 20050147671 and 20050215643. They describe the use of relatively low levels of alkali metal bicarbonates, 20-80% by weight with respect to diclofenac (10-40 mg for a 50 mg dose), in various dosage forms including soluble or dispersible powders, two layered tablets and liquid drop solutions. The alkali metal bicarbonates improve the palatability of the powder formulations that are intended for mixing with water before ingestion. In vivo, such formulations achieve faster and more reproducible absorption with higher peak plasma concentrations than commercially available products.

The taste masking effect of sodium or potassium salts including bicarbonates has been described for non-effervescent soluble formulations of ibuprofen in U.S. Pat. No. 5,262,179 (Gregory et al).

Isotonicity

Some publications teach the inclusion of about 630 mg sodium bicarbonate in swallow tablets so as to provide isotonic conditions in the stomach which promote absorption of the drug.

U.S. Pat. No. 6,316,025 (Grattan) describes a swallow tablet of paracetamol, an unionized drug, containing 300 mg to 1000 mg of sodium bicarbonate per tablet with a paracetamol to sodium bicarbonate ratio of between 0.74 and 1. Grattan et al., *Eur. J. Pharm. Biopharm* 49(3): 225-229, 2000, subsequently reported that a formulation with 630 mg sodium bicarbonate provided improved pharmacokinetic outcomes. It was suggested that this was due to an osmotic effect of the level of sodium bicarbonate, which would be isotonic when two tablets are ingested with 100 mL of water and which would promote absorption. Kelly et al, *Pharmaceutical Research*, 2003, 20 (10) 1668-1673, attribute the faster absorption of paracetamol in vivo from a formulation containing 1260 mg sodium bicarbonate per dose, to faster disintegration and dissolution caused by the resultant effervescence, and the prokinetic effect of the resultant isotonic solution on gastric emptying.

Similarly, US Patent Application 20040204475 (Humphrey) teaches the use of sufficient sodium bicarbonate with eletriptan, a basic drug, to create an isotonic solution in the duodenum, with examples containing 630 mg per tablet.

Neutralising Gastric pH

U.S. Pat. No. 6,699,885 (Phillips) relates to formulations including omeprazole and bicarbonate or carbonate to protect the omeprazole from gastric acid degradation in amounts from about 250 mg to 4,000 mg, thus comprising the major proportion of the tablet by weight. This teaches the use of high levels of antacid to neutralise the gastric contents and so protect the drug from degradation. This eliminates the need for enteric coating which delays dissolution and absorption.

Dissolution Testing

Dissolution testing provides a convenient in vitro method to measure the dissolution of a formulation, which is one factor that can be used in predicting its in vivo dissolution. Fast in vitro dissolution under test conditions it typically indicative of fast in vivo dissolution. In turn, this typically favours the fastest possible absorption of the drug to the extent of the inherent absorption characteristics of that drug.

Further to this, the FDA Guidances for Industry based on the Biopharmaceutics Classification System (BCS) Guidance and in vitro dissolution testing assigns drugs to one of four classes depending on their solubility and intestinal permeability. For example, BCS Class 1 drugs with high solubility and high permeability, rapid in vitro dissolution correlates with fast in vivo dissolution and fast absorption. A point-to-point IVIVC is expected for poorly water soluble drugs where there is no intestinal permeability limitation (Class 2), but IVIVC is less likely for Class 3 and Class 4 drugs which are permeability limited.

Certain dissolution media can be used to assess the effect of different formulations in modifying gastric pH and the impact of this on drug dissolution.

Basic and Amphoteric Actives

It is widely accepted that raising the pH will reduce the solubility and hence inhibit the dissolution of basic compounds. Precipitation of the basic compound ondansetron in alkaline solutions containing sodium bicarbonate has been reported as a result of the effect of pH on the solubility of this basic drug (Jaronsinski P F and Hirschfield S, *N. Eng. J. Med.* 325:1315-1316, 1001).

Reduced solubility at high pH can prove advantageous for bitter tasting drugs. WO 2004/017976 (Tian et al) describes a fast dissolving and fast disintegrating, taste masked oral dosage form comprising the basic compound sildenafil. The specification describes the use of any pharmaceutically acceptable pH raising agent to inhibit dissolution of sildenafil, preventing dissolution of sildenafil in the mouth and thus masking the bitter taste of the drug. Agents that raise or increase the pH include sodium carbonate, sodium bicarbonate, calcium carbonate and magnesium carbonate.

US Patent Application 20050032867 (Baker et al) describes a fast disintegrating and dispersing sumatriptan formulation comprising about 5 to about 50% by weight base component. The base component of the formulation reacts with the acid component of the stomach, sumatriptan or acid component of the tablet to generate gas so as to facilitate the dissolution of the drug and hence its absorption. There is no teaching in relation to the effect of the base component on the solubility of the drug and its dissolution.

On the basis of these disclosures, it would be expected that the addition of bases such as carbonates to therapeutic compounds that are bases, salts of bases, amphoteric compounds or salts of amphoteric compounds, will reduce their solubility and hence dissolution as a result of the increased pH. Unexpectedly, we have found that for swallow formulations in the case of basic and amphoteric drugs, where increased pH is likely to lead to lower solubility and hence worse dissolution and absorption, the use of pH modulating agents can still achieve increased dissolution and potentially increased absorption. Furthermore, if a carbonate is used in a swallow formulation, with the level optimized for each drug, then enhanced dissolution can always be achieved, particularly for drugs with limited solubility.

Acids and Unionized Actives

A number of publications disclose the use of alkaline agents with acidic and unionized actives that differ from the present invention.

One example is reduced gastric toxicity of NSAIDs in swallow formulations which, unlike the present invention, contain cyclodextrins. U.S. Pat. No. 5,854,226 (Penkler et al) is directed to such formulations that minimize gastric irritation and achieve rapid absorption. These contain an inclusion complex of the NSAID with cyclodextrin and an alkali agent present in an amount capable of forming an alkaline diffusion layer around the composition in the gastrointestinal tract.

Another example is directed to the provision of small tablets (around 330 mg, including about 220 mg naproxen)

which are easy to manufacture and rapidly absorbed. International patent application WO 2005/041938 (Gruber et al) relates to non-effervescent formulations, comprising 30 to 90 wt % sodium naproxen and 1 to 70 wt % auxiliary agent, comprising at least one basic auxiliary agent. Dissolution testing disclosed in the examples shows no greater than 50 wt % dissolution within 300 sec using 1000 mL of 0.1 N hydrochloric acid and paddle speed of 50 rpm (using the European Pharmacopeia method).

A further example described in U.S. Pat. No. 6,165,506 (Jain et al) is a fast dissolving naproxen formulation comprising nanoparticulate naproxen (less than 600 nm particle size) having adsorbed to it surface a surface modifying agent such as polyvinylpyrrolidone.

Both WO 2005/041938 and U.S. Pat. No. 6,165,506 teach manufacture of a small tablet having low levels of a base such as sodium bicarbonate, alone or with an organic acid to increase dissolution rate by the resultant effervescence. Furthermore both applications teach comparatively low levels of binders and disintegrants, which are essentially substituted by the base/acid. Neither contain sufficient base to increase pH in vivo.

In contrast to these preceding examples, a relatively large amount of prior art deals with the use of sodium bicarbonate and other pH modulating agents to affect the absorption of acidic drugs, particularly acidic NSAIDs and their salts. These relate to the higher solubility of acidic drugs at elevated pH.

Many acidic drugs have limited solubility in acidic solutions and so are frequently used as the more soluble salt form. This will potentially improve dissolution in vitro and in vivo. However U.S. Pat. No. 4,704,405 (O'Neill et al) describes the lack of improved absorption from formulations containing sodium sulindac relative to the less soluble sulindac. The inclusion of a base such as tromethamine or sodium bicarbonate in swallow formulations containing sodium sulindac was found to achieve improved bioavailability and onset of action compared with conventional tablets. The excess base was found to improve the absorption by neutralizing the gastric contents, solubilising the drug at this higher pH and delivering the solution to the duodenum for absorption. High levels of sodium bicarbonate are used in an amount between 0.8 g and 2.0 g to neutralize the gastric contents.

However, Neuvonen, P. J and Kivisto, K. T. (*Clin. Pharmacokinet.* 27 (2) 120-8, 1994.) reviewed the effects of various antacids, including high doses of sodium bicarbonate and magnesium hydroxide, on the absorption of different weakly acidic drugs. They noted that, although all antacids had a similar neutralising effect on gastric acid and so would increase the pH and hence the drug solubility, the effects on absorption were different depending on the drug and the antacid.

WO 9744023 (Reiner et al) deals with the use of sodium and potassium bicarbonate to enhance absorption of salts of diclofenac. They disclose the use of low levels of bicarbonate, 10-40 mg relative to a 50 mg dose of diclofenac which also masks the bitter taste of the drug since the low amount of bicarbonate used will not significantly increase the pH and the solubility of the drug remains low.

The above examples teach the use of high levels of antacids and bicarbonates to neutralize gastric contents resulting in improved absorption, particularly where the elevated pH improves the solubility of poorly soluble acidic drugs.

Surprisingly it has been found that for swallow formulations, the inclusion of alkali agents in the formulation at levels that will increase the pH of an acidic dissolution medium, is not always associated with fast dissolution or fast absorption. However if a bicarbonate is used in a swallow formulation, with the level optimized for each drug, then enhanced dissolution can always be achieved, particularly for drugs with limited solubility, whether the drug is an acid, a salt of an acid or an unionized compound. Furthermore, in vivo studies using paracetamol as a marker drug for gastric emptying have shown that the use of bicarbonates in swallow formulations results in faster absorption than the use of other alkali agents despite increased gastric pH.

The rate of dissolution is further enhanced as the particle size of the therapeutic agent is reduced and the surface area correspondingly increased.

For acidic drugs, improved dissolution can be demonstrated at lower pH values prior to total neutralization of the acid. This allows the use of levels of bicarbonates lower than those required to completely neutralize the gastric contents, which is of particular importance for patients who need to restrict their sodium intake.

In accordance with the present invention, therapeutic compositions intended for administration intact are defined in which the addition of bases to the therapeutic compounds enable enhanced in vitro dissolution of the therapeutic agent. In particular the present invention defines therapeutic compositions in which the addition of bases such as soluble carbonates or bicarbonates to therapeutic compounds chosen from the group comprising acids, bases, amphoterics, unionized actives, their salts, their proactive forms or combinations thereof will enable enhanced in vitro dissolution of the therapeutic agent.

SUMMARY OF THE INVENTION

The present invention relates generally to therapeutic formulations and more particularly fast dissolving swallow formulations for a therapeutic compound chosen from the group comprising acids, bases, amphoterics, unionized actives, their salts, their proactive forms or combinations thereof with pharmacological, physiological or biochemical activity.

In particular, the present invention provides a swallow formulation comprising, (a) a therapeutic compound that is chosen from the group comprising acids, bases, amphoterics or unionized actives, their salts, their proactive forms or combinations thereof, and (b) an appropriate amount of one or more pH modulating agents that include an appropriate amount of one or more soluble carbonates in an amount that will neutralise 0.01 to 10 millimoles of hydrochloric acid, and is present in an amount from about 1% to 50% by weight of the swallow formulation, and wherein the therapeutic compound exhibits a dissolution profile chosen from the group comprising, at least 20% dissolution from the swallow formulation within 180 seconds, at least 40% dissolution from the swallow formulation within 240 seconds, at least 50% dissolution from the swallow formulation within 300 seconds, when measured at 30 rpm in United States Pharmacopoeia (USP) dissolution apparatus 2 with 900 mL 0.0033 N hydrochloric acid at 37° C., or at least 5% dissolution from the swallow formulation within 30 minutes, at least 5% dissolution from the swallow formulation within 300 seconds when measured at 0 rpm in USP dissolution apparatus 2 with 900 mL 0.0033 N hydrochloric acid at 37° C.

Preferably, the swallow formulation further comprises an agent which facilitates water uptake into the dosage form. The swallow formulation of the present invention exhibits enhanced dissolution of the therapeutic compound from the formulation.

Preferred Embodiment—Acid or Unionized Therapeutic Compound

In one preferred embodiment, the swallow formulation comprises,
(a) a therapeutic compound chosen from the group comprising acids, unionized compounds, their salts, proactive forms or combinations thereof, and
(b) a pH modulating agent that includes one or more soluble bicarbonates in an amount that will neutralise about 0.1 to 10 millimoles of hydrochloric acid,
wherein at least about 50% of the therapeutic compound is dissolved from the swallow formulation within 300 seconds in USP dissolution apparatus 2 with 900 mL 0.0033 N hydrochloric acid at 30 rpm and 37° C. This quantity of dissolution medium contains 3 millimoles of hydrochloric acid.

In another embodiment of the invention, at least about 40% of the therapeutic compound is dissolved from the swallow formulation within 240 seconds in USP dissolution apparatus 2 with 900 mL 0.0033 N hydrochloric acid at 30 rpm and 37° C.

In another embodiment of the invention, at least about 20% of the therapeutic compound is dissolved from the swallow formulation within 180 seconds in USP dissolution apparatus 2 with 900 mL 0.0033 N hydrochloric acid at 30 rpm and 37° C. Preferably, at least about 25% of the therapeutic compound is dissolved from the swallow formulation within 180 seconds.

In a further embodiment of the invention, greater than 5% of the therapeutic compound is dissolved from the swallow formulation within 30 minutes in USP dissolution apparatus 2 with 900 mL 0.0033 N hydrochloric acid at 0 rpm and 37° C.

Preferred Embodiment—Base or Amphoteric Therapeutic Compound

The present invention provides a swallow formulation comprising
(a) a therapeutic compound chosen from the group comprising bases, amphoterics, their salts, their or proactive forms or combinations thereof, and
(b) an appropriate amount of one or more pH modulating agents wherein at least one pH modulating agent is a carbonate in an amount that will neutralise 0.01 to 9.0 millimoles of hydrochloric acid and is present in an amount from about 1% to 50% by weight of the swallow formulation,
wherein at least about 70% of the therapeutic compound is dissolved from the swallow formulation within 180 seconds, at 30 rpm when the dissolution is measured in USP dissolution apparatus 2 with 900 mL 0.0033 N hydrochloric acid at 37° C.

In a particularly preferred embodiment of the invention at least about 90% of the therapeutic compound is dissolved from the swallow formulation within 180 seconds at 30 rpm in USP dissolution apparatus 2 with 900 mL 0.0033 N hydrochloric acid at 30 rpm and 37° C.

The present invention further provides a swallow formulation comprising
(a) a therapeutic compound chosen from the group comprising bases, amphoterics, their salts, their proactive forms or combinations thereof, and
(b) an appropriate amount of one or more pH modulating agents wherein at least one pH modulating agent is a carbonate in an amount that will neutralise 0.01 to 9.0 millimoles of hydrochloric acid and is present in an amount from about 1% to 50% by weight of the swallow formulation,
wherein at least about 5% of the therapeutic compound is dissolved from the swallow formulation within 300 seconds at 0 rpm when the dissolution is measured in USP dissolution apparatus 2 with 900 mL 0.0033 N hydrochloric acid at 37° C.

In one embodiment of the invention at least about 20% or the therapeutic compound is dissolved from the swallow formulation within 300 seconds at 30 rpm in USP dissolution apparatus 2 with 900 mL 0.0033 N hydrochloric acid at 30 rpm and 37° C.

The present invention further provides a swallow formulation comprising
(a) a therapeutic compound that is a base, amphoteric, their salts, their proactive forms or mixtures thereof, and
(b) an appropriate amount of one or more pH modulating agents wherein at least one pH modulating agent is a carbonate in an amount that will neutralise 0.01 to 9.0 millimoles of hydrochloric acid and is present in an amount from about 1% to 50% by weight of the swallow formulation,
wherein
(i) at least about 70% of the therapeutic compound is dissolved from the swallow formulation within 180 seconds at 30 rpm, and
(ii) at least about 5% of the therapeutic compound is dissolved from the swallow formulation within 300 seconds at 0 rpm wherein the dissolution is measured in USP dissolution apparatus 2 with 900 mL 0.0033 N hydrochloric acid at 37° C.

Typically, when the pH modulating agent of the swallow formulation comprises a base (but no acid), the dissolution rate is greater than 5% at 30 minutes at 0 rpm. More typically the dissolution rate is greater than 20% at 30 minutes at 0 rpm.

Typically when the pH modulating agent of the swallow formulation comprises a base and an acid, the dissolution rage is greater than 5% at 300 seconds at 0 rpm. More typically the dissolution rate is greater than 20% at 300 seconds at 0 rpm.

A dissolution medium comprising 900 mL of 0.0033 N hydrochloric acid contains 3 millimoles of hydrochloric acid, approximating the amount of acid estimated to be present in the residual gastric contents in a fasted subject. This amount of acid can be completely neutralized by high amounts of bases used as pH modulating agents, so that the pH of the dissolution medium will change depending on the levels of pH modulating agents used in a formulation. This is particularly important for investigating the dissolution of drugs where their solubilities are pH dependent.

Dissolution results using 900 mL 0.0033 N hydrochloric acid will be of importance in vivo as the acidity of gastric contents varies significantly. Low acid or neutral conditions are associated with the fed and partial prandial states, as well as in patients with suppressed gastric function. Hence dissolution performance of solid dosage forms will also be important in neutral dissolution media such as deionized water and full cream milk which simulates the fed state. An ideal formulation designed for fast absorption such as the subject of this invention, should demonstrate fast dissolution in all such dissolution media.

When the stirring speed is reduced to 0 rpm, the dissolution profiles demonstrate the intrinsic characteristics of the fast dissolving formulations of this invention which are able to enhance the dissolution of the drugs without any external stirring. Dissolution results without stirring may be of in vivo significance in conditions where there is gut stasis or reduced gastric motility.

The preferred amount of pH modulating agent is an amount sufficient to enhance the dissolution of the therapeutic compound from the swallow formulation. This amount will vary depending on the therapeutic compound, and also on the composition of the pH modulating agent which can contain both bases and acids. Preferably the pH modulating agent will be in an amount so as not to increase the pH of a 900 mL 0.0033 N hydrochloric acid dissolution medium that contains 3 millimoles of hydrochloric acid to greater than 6.

Preferably, the swallow formulation further comprises an agent which facilitates water uptake. The swallow formulation of the present invention exhibits enhanced dissolution of the therapeutic compound from the formulation.

In addition, the fast dissolving oral delivery system may contain a combination of pharmaceutically acceptable excipients or other components such as water uptake agents, disintegrants, preservatives, colors, anti-oxidants, emulsifiers, sweeteners, flavoring agents, binders, glidants and lubricants. In an exemplary form, the fast dissolving delivery system may also contain one or more pharmaceutically active agents. The oral solid dosage form may be administered by swallowing with water or any other liquid.

An appropriate amount of pH modulating agent is an amount sufficient to enhance the dissolution of the therapeutic compound from the swallow formulation. This amount will vary depending on the therapeutic compound.

Another aspect of the invention provides a dosage form such as a coated tablet, uncoated tablet, capsule, powder, paste, cachet, colloid, gel or melt.

The present invention contemplates a method for delivering a therapeutic compound that is chosen from the group comprising acids, bases, amphoterics or unionized actives, their salts, their proactive forms or combinations thereof, by oral delivery including administration such as by swallowing, the method comprising orally delivering, including administering, a formulation comprising a therapeutic compound with an appropriate amount of one or more pH modulating agents wherein at least one of the pH modulating agents is a bicarbonate so as to enhance the dissolution of the therapeutic compound from the swallow formulation.

The present invention further contemplates a method for delivering a diagnostic agent that is chosen from the group comprising acids, bases, amphoterics or unionized actives, their salts, their proactive forms or combinations thereof, by oral delivery including administration such as by swallowing, the method comprising orally delivering, including administering, a formulation comprising a diagnostic agent with an appropriate amount of one or more pH modulating agents wherein at least one of the pH modulating agents is a bicarbonate so as to enhance the dissolution of the diagnostic agent from the swallow formulation.

BRIEF DESCRIPTION OF THE DRAWINGS

FIG. 1: dissolution of ibuprofen sodium and ibuprofen mixtures in 900 mL 0.0033N HCl at 30 rpm.

FIG. 2: Dissolution of ibuprofen in 900 mL 0.0033N HCl at 30 rpm.

FIG. 3: Dissolution of diclofenac potassium in 900 mL 0.0033N HCl at 30 rpm.

FIG. 4: Dissolution of paracetamol in 900 mL 0.0033N HCl at 30 rpm.

FIG. 5: Dissolution of naproxen in 900 mL 0.0033N HCl at 30 rpm.

FIG. 6: Dissolution of naproxen sodium in 900 mL 0.0033N HCl at 30 rpm.

FIG. 7: Dissolution of gemfibrozil in 900 mL 0.0033N HCl at 30 rpm.

FIG. 8: Dissolution of furosemide in 900 mL 0.0033N HCl at 30 rpm.

FIG. 9: Dissolution profile for temazepam in 900 mL 0.0033N HCl at 30 rpm.

FIG. 10: Dissolution profile for montelukast sodium in 900 mL 0.0033N HCl at 30 rpm.

FIG. 11: Dissolution profile for a mixture of ibuprofen and sodium ibuprofen in 900 mL 0.0033N HCl at 0 rpm.

FIG. 12: Dissolution profile for ibuprofen in 900 mL 0.0033N HCl at 0 rpm.

FIG. 13: Dissolution profiles for diclofenac potassium in 900 mL 0.0033N HCl at 0 rpm.

FIG. 14: Dissolution profile for paracetamol commercial products in 900 mL 0.0033N HCl at 0 rpm.

FIG. 15: Dissolution profiles for paracetamol in 900 mL 0.0033N HCl at 0 rpm.

FIG. 16: Dissolution profiles for naproxen in 900 mL 0.0033N HCl at 0 rpm.

FIG. 17: Dissolution profiles for naproxen sodium in 900 mL 0.0033N HCl at 0 rpm.

FIG. 18: Dissolution profiles for gemfibrozil in 900 mL 0.0033N HCl at 0 rpm.

FIG. 19: Dissolution profiles for furosemide in 900 mL 0.0033N HCl at 0 rpm.

FIG. 20: Dissolution profiles for temazepam in 900 mL 0.0033N HCl at 0 rpm.

FIG. 21: Dissolution profiles for montelukast sodium in 900 mL 0.0033N HCl at 0 rpm.

FIG. 22: Dissolution profiles for prednisolone 5 mg in 900 mL 0.0033N HCl at 30 rpm.

FIG. 23: Dissolution profiles for prednisolone 25 mg in 900 mL 0.0033N HCl at 30 rpm.

FIG. 24: Dissolution profiles for prednisolone 5 mg in 900 mL 0.0033N HCl at 0 rpm.

FIG. 25: Dissolution profiles for prednisolone 25 mg in 900 mL 0.0033N HCl at 0 rpm.

FIG. 26: Dissolution profiles for dexamethasone in 900 mL 0.0033N HCl at 30 rpm.

FIG. 27: Dissolution profiles for dexamethasone in 900 mL 0.0033N HCl at 0 rpm.

FIG. 28: Dissolution profiles for fexofenadine hydrochloride in 900 mL 0.0033N HCl at 30 rpm.

FIG. 29: Dissolution profiles for fexofenadine hydrochloride in 900 mL 0.0033N HCl at 0 rpm.

FIG. 30: Dissolution profiles for pseudoephedrine hydrochloride in 900 mL 0.0033N HCl at 30 rpm.

FIG. 31: Dissolution profiles for pseudoephedrine hydrochloride in 900 mL 0.0033N HCl at 0 rpm.

FIG. 32: Dissolution profiles for eletriptan hydrobromide in 900 mL 0.0033N HCl at 30 rpm.

FIG. 33: Dissolution profiles for eletriptan hydrobromide in 900 mL 0.0033N HCl at 0 rpm.

FIG. 34: Dissolution profiles for rizatriptan benzoate in 900 mL 0.0033N HCl at 30 rpm.

FIG. 35: Dissolution profiles for rizatriptan benzoate in 900 mL 0.0033N HCl at 0 rpm.

FIG. 36: Dissolution profiles for metoclopramide hydrochloride in 900 mL 0.0033N HCl at 30 rpm.

FIG. 37: Dissolution profiles for metoclopramide hydrochloride in 900 mL 0.0033N HCl at 0 rpm.

FIG. 38: Dissolution profiles for loperamide hydrochloride in 900 mL 0.0033N HCl at 30 rpm.

FIG. 39: Dissolution profiles for loperamide hydrochloride in 900 mL 0.0033N HCl at 0 rpm.

FIG. 40: Dissolution profiles for codeine phosphate in 900 mL 0.0033N HCl at 30 rpm.

FIG. 41: Dissolution profiles for codeine phosphate in 900 mL 0.0033N HCl at 0 rpm.

FIG. 42: Dissolution profiles for tramadol hydrochloride in 900 mL 0.0033N HCl at 30 rpm.

FIG. 43: Dissolution profiles for tramadol hydrochloride in 900 mL 0.0033N HCl at 0 rpm.

FIG. 44: Dissolution profiles for diazepam in 900 mL 0.0033N HCl at 30 rpm.

FIG. 45: Dissolution profiles for diazepam in 900 mL 0.0033N HCl at 0 rpm.

FIG. 46: Dissolution profiles for lorazepam in 900 mL 0.0033N HCl at 30 rpm.

FIG. 47: Dissolution profiles for lorazepam in 900 mL 0.0033N HCl at 0 rpm.

FIG. 48: Dissolution profiles for alprazolam in 900 mL 0.0033N HCl at 30 rpm.

FIG. 49: Dissolution profiles for alprazolam in 900 mL 0.0033N HCl at 0 rpm.

FIG. 50: Dissolution profiles for sildenafil citrate in 900 mL 0.0033N HCl at 30 rpm.

FIG. 51: Dissolution profiles for sildenafil citrate in 900 mL 0.0033N HCl at 0 rpm.

FIG. 52: Dissolution profiles for ondansetron hydrochloride in 900 mL 0.0033N HCl at 30 rpm.

FIG. 53: Dissolution profiles for ondansetron hydrochloride in 900 mL 0.0033N HCl at 0 rpm.

FIG. 54: Dissolution profiles for zolmitriptan in 900 mL 0.0033N HCl at 30 rpm.

FIG. 55: Dissolution profiles for zolmitriptan in 900 mL 0.0033N HCl at 0 rpm.

FIG. 56: Dissolution profiles for zolpidem tartrate in 900 mL 0.0033N HCl at 30 rpm.

FIG. 57: Dissolution profiles for zolpidem tartrate in 900 mL 0.0033N HCl at 0 rpm.

FIG. 58: Dissolution profiles for cetirizine dihydrochloride in 900 mL 0.0033N HCl at 30 rpm.

FIG. 59: Dissolution profiles for cetirizine dihydrochloride in 900 mL 0.0033N HCl at 0 rpm.

FIG. 60: Dissolution profiles for paracetamol in 900 mL 0.0033N HCl at 30 rpm comparing two wet granulated formulations with two fast acting commercial products.

FIG. 61: Dissolution profiles for paracetamol in 900 mL 0.0033N HCl at 0 rpm comparing two wet granulated formulations with two fast acting commercial products.

FIG. 62: Dissolution profiles for paracetamol and tramadol hydrochloride in 900 mL 0.0033N HCl at 30 rpm.

FIG. 63: Dissolution profiles for paracetamol and tramadol hydrochloride in 900 mL 0.0033N HCl at 0 rpm.

FIG. 64: Dissolution of ibuprofen formulations in 200 mL water at 30 rpm as an example of a neutral Dissolution medium.

FIG. 65: Dissolution of paracetamol formulations in 200 mL full cream milk at 30 rpm and 37° C., which approximates the fed state.

FIG. 66: Dissolution of zolpidem tartrate formulations in 200 mL full cream milk at 30 rpm and 37° C., which approximates the fed state.

DETAILED DESCRIPTION OF THE PREFERRED EMBODIMENTS

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The word 'comprising' and forms of the word 'comprising' as used in this description and in the claims does not limit the invention claimed to exclude any variants or additions.

Reference hereinafter to a "therapeutic compound" includes any pharmacologically, physiologically or biochemically active compound or proactive form thereof.

It is to be understood that unless otherwise indicated, the subject invention is not limited to specific formulation components, manufacturing methods, dosage regimens, or the like, as such may vary. In describing and claiming the present invention, the following terminology is used in accordance with the definitions set forth below. It is also to be understood that the terminology used herein is for the purpose of describing particular embodiments only and is not intended to be limiting.

It must also be noted that, as used in the subject specification, the singular forms "a", "an" and "the" include plural aspects unless the context clearly dictates otherwise. Thus, for example, reference to "therapeutic compound" includes a single therapeutic compound, as well as two or more therapeutic compounds; reference to "a pH modulating agent" includes a single pH modulating agent, as well as two or more pH modulating agents; reference to "a water uptake agent" includes a single water uptake agent, as well as two or more water uptake agents; and so forth.

Where used herein "unionized" refers to a drug that is largely unionized between approximately pH 2 and pH 8. Of course the person skilled in the art will understand that there will be some extent of unionization of almost any drug in the right pH. Typically the unionized drug will be >50% ionized below pH 2 and above pH 8.

A "swallow formulation" is any formulation which is administered to a subject by the action of swallowing the dosage form intact. The dosage form comprising the swallow formulation may be a coated tablet or capsule which does not have the same dissolution characteristics of the swallow formulation contained therein.

The terms "therapeutic compound", "compound", "pharmacologically active agent", "medicament", "active", "active ingredient", "drug" and "drug component" are used interchangeably throughout this specification. The terms also encompass pharmaceutically acceptable and pharmacologically active ingredients of those active agents specifically mentioned herein including but not limited to salts, esters, amides, pro-drugs, active metabolites, analogs and the like. When the terms "active agent", "compound", "pharmacologically active agent", "medicament", "active", "drug", and "drug component" are used, then it is to be understood that this includes those compounds per se as well as pharmaceutically acceptable, pharmacologically active salts, esters, amides, pro-drugs, metabolites, analogs, etc. The terms "agent", "compound" etc may be a single molecule or a composite of molecules.

For the purposes of this patent, diagnostic agents are defined as "active ingredients" above, excepting that they are used for diagnostic, not therapeutic purposes.

By the term "effective amount" or "therapeutically effective amount" of a therapeutic compound as used herein means that a sufficient amount of a therapeutic compound is used to provide the desired therapeutic effect or the desired physiological or biochemical event including the amelioration of symptoms being treated or prevented. Of course, undesirable effects, e.g. side effects, are sometimes manifested along with the desired therapeutic effect; hence, a practitioner balances the potential benefits against the potential risks in determining what an appropriate "effective amount" is.

The terms "delivery" and "administration" are used interchangeably throughout the specification to mean the act of providing the oral dosage form to an individual. The term "administering" is considered herein synonymous with "delivering", "providing", "introducing" or "swallowing".

By "pharmaceutically acceptable excipient" is meant a pharmaceutical vehicle comprised of a material that is not biologically or otherwise undesirable, i.e. the oral dosage form may be administered to a subject along with a therapeutic compound without causing any or a substantial adverse reaction. Excipients may include carriers and other additives such as diluents, binders, detergents, colouring agents, flavoring agents, wetting or emulsifying agents, preservatives, glidants, lubricants and the like as well as disintegrants.

The terms "treating" and "treatment" as used herein refer to reduction or amelioration in severity and/or frequency of symptoms, elimination of symptoms and/or underlying cause and/or prevention of the occurrence of symptoms and/or their underlying cause. Thus, for example, "treating" a patient involves prevention of a particular disorder or adverse physiological event in a susceptible individual, as well as treatment of a clinically symptomatic individual by inhibiting or causing regression of a particular condition. Thus, for example, a method of treating a patient in need of pain relief encompasses both preventing pain as well as treating conditions of pain.

"Patient" as used herein refers to an animal, preferably a mammal and more preferably human who can benefit from the pharmaceutical formulations and methods of the present invention. There is no limitation on the type of animal that could benefit from the presently described pharmaceutical formulations and methods. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird, an aviary bird or game bird.

The preferred animals are humans or other primates, livestock animals, laboratory test animals, companion animals or captive wild animals. A human is the most preferred target.

A "pH modulating agent" includes one or more than one pH modulating agents which alter the pH of an aqueous solution. These may include acids, bases or a combination of one or more acids and/or bases.

The carbonate may be any pharmaceutically acceptable soluble carbonate or a mixture thereof and includes bicarbonate. Reference to a "bicarbonate" or a "carbonate" includes a single agent or multiple (i.e. two or more) agents. Preferred carbonates include but are not limited to sodium bicarbonate, sodium carbonate, potassium bicarbonate, potassium carbonate, calcium bicarbonate, calcium carbonate, magnesium bicarbonate, magnesium carbonate, ammonium bicarbonate, ammonium carbonate, sodium glycine carbonate, disodium glycine carbonate, arginine carbonate, lysine carbonate and/or other pharmaceutically acceptable carbonates or homologs or functional equivalents thereof and combinations thereof.

Optionally the swallow formulation may include pharmaceutically acceptable acids or acidic salts including citric acid, tartaric acid, succinic acid, ascorbic acid, malic acid, fumaric acid, metatartaric acid, adipic acid, sodium acid citrate, potassium acid citrate, glycine citrate, potassium acid tartrate, sodium acid tartrate, aspartic acid, glutamic acid, glycine, leucine, tyrosine, tryptophan, glycine fumarate, glycine hydrochloride, monophosphate glycine and combinations thereof. These pharmaceutically acceptable acids or acidic salts may for example, be included in the swallow formulation as further pH modulating agents.

A "water uptake agent" is any agent which will facilitate the uptake of water by absorbing, dissolving in or wicking water, used alone or in combination. These may include wicking agents, disintegrants, binders, carriers and other hydrophilic excipients. Generally, but not exclusively, a "water uptake agent" facilitates uptake of water into the swallow formulation. Suitable water uptake agents include cross-linked polyvinylpyrrolidone (crospovidone), croscarmellose sodium, sodium starch glycolate, starch, starch derivatives, hydroxypropylcellulose, low substituted hydroxypropylcellulose, hydroxypropylmethylcellulose, alginic acid, sodium alginate, calcium sulphate, calcium carboxymethylcellulose, microcrystalline cellulose, powdered cellulose, colloidal silicon dioxide, docusate sodium, guar gum, magnesium aluminium silicate, methylcellulose, polacrilin potassium, silicified microcrystalline cellulose, magnesium oxide, tragacanth, mannitol, sorbitol, xylitol, sucrose, lactose, fructose, maltose, polyethylene glycol, aminoacids, cyclodextrin, urea and/or polyvinylpyrrolidone (povidone, PVP).

Whilst not wishing to be bound by theory, the bicarbonate assists with the dissolution in a number of ways. Of particular importance is the effervescence, ie the release of the gas, carbon dioxide ($CO_2$) when bicarbonate reacts with stomach or exogenous acid. Whilst it is possible to calculate the theoretical amount of gas that will be produced, it is the rate of production that is critical and it is difficult to measure this directly. The advantage provided by the $CO_2$ release can be measured indirectly by measuring the rate of dissolution of the tablet without any stirring (ie at 0 rpm). At 0 rpm, the formulation itself will provide the only source of stirring from the gas produced. Use of dissolution media containing lower levels of acid, such as 0.0033 N hydrochloric acid, allows greater discrimination between formulations with different rates of production of carbon dioxide and may be especially important in mimicking the effects of low gastric acid levels (achlorhydria) seen in a significant proportion of the human population. Formulations which do not effervesce or effervesce only slowly show little if any dissolution even after an extended time.

Solubility Considerations

The effect of tablet formulations on drug dissolution will be dependent on the nature and amount of the drug included in each tablet, and the levels of base and acid used in the formulation. The addition of optimised amounts and ratios of acids and bases can significantly improve the dissolution of a range of different drugs as a result of the effect of the acid-base couple on the micro pH in the tablet and on the pH of the dissolution medium, which in turn can change the solubility of a drug. In addition, appropriate effervescent formulations may compensate for reduced gastric acid content which is either inherent (eg achlorhydria) or induced (eg by antacid or food).

In general,

To increase the dissolution rate of acidic drugs which have a higher solubility under alkaline conditions, an excess of the base component of an acid-base couple is required to produce an alkaline micro pH in the tablet and to increase the pH of the dissolution medium to around pH 6.

For unionized or neutral drugs, where pH does not have a major effect on the solubility of the drug, the increased rate of dissolution will be proportional to the level of acid-base couple used, as a result of the microstirring produced by the effervescence.

For basic drugs where the solubility decreases with an increase in pH, then for maximum dissolution, it is important that there is no significant net increase in the pH such as is achieved with stoichiometric amounts of acid and a base (in the pH modulating agent) since they react with each other. There will only be a net effect on pH if one or the other component is in excess.

Amphoteric drugs behave like basic or acidic drugs depending on the pKa and the pH. Amphoteric drugs behaving as bases will demonstrate reduced solubility at higher pH as the more soluble acid salt is converted to the less soluble, less ionized form. As these drugs also behave as acids it is important to optimise the pH in the formulation for optimum solubility for each specific drug.

Examples of suitable active agents include and are not limited to analgesics, antipyretics, anti-inflammatory agents, antidepressants, anti-asthma agents, antibiotics, antivirals, antifungals, anticonvulsants, antidiabetics, anti-gout agents, antihistamines and anti-allergy agents, antihypertensives, anti-migraine agents, anti-muscarinics, antinauseants, antineoplastics, antpsoriatics, antispasmodics and motility agents, antithrombotics, bone modulating agents, bronchodilators, cardiovascular drugs, diuretics, diagnostic agents, dopaminergics, anxiolytics, sedatives, hypnotics and antipsychotics, immunomodulators, lipid regulating agents, muscle relaxants, nutritional supplements, sedatives, thyroid agents, uricosurics, vasodilators and vitamins.

Preferred therapeutic compounds include those which can exist in the unionized form under acidic conditions including those with one or more acidic groups and pharmaceutically acceptable salts thereof. Examples include but are not limited to NSAIDs such as acetyl salicylic acid, diclofenac, fenoprofen, ibuprofen, indomethacin, ketoprofen, meclofenamic acid, mefenamic acid, naproxen, piroxicam, sulindac, rofecoxib, antibiotics such as penicillins, cephalosporins, quinolones, tetracyclines and sulphonamides, trimethoprim, weakly basic benzodiazepines such as temazepam and flunitrazepam, barbiturates, bisphosphonates such as pamidronic acid, risedronic acid and zoledronic acid, statins such as atorvastin, simvastatin, cerivastin, fluvastin and pravastatin, fibrates such as clofibrate, bezafibrate and gemfibrozil, ascorbic acid, captopril, chlorambucil, cyclophosphamide, fluoxetine and norfluoxetine, folic acid, furosemide, fusidic acid, glibenclamide, gliclazide, glutethimide, isoniazid, levodopa, methotrexate, methyldopa, montelukast, nalidixic acid, phenacetin, phenindione, probenecid, rifampicin, sulphasalazine, sulphinpyrazone, thyroxine, tolazamide, tolbutamide, valproic acid, warfarin, sodium cromoglycate, fenoterol, salbutamol, theophylline and aminophylline, zafirlukast and corticosteroids such as betamethasone, dexamethasone, triamcinolone, prednisolone, prednisone.

Preferred therapeutic compounds include those which have one or more base groups such as but not limited opiates such as hyrocodone, oxycodone, the triptans including eletriptan, rizatriptan, zolmitriptan; the benzodiazepines including diazepam, flurazepam, flunitrazepam, temazepam, alprazolam, lorazepam; fexofenadine; metoclopramide, loperamide, zolpidem, zopiclone, loratadine, ondansetron, granisetron, tadalafil, vardenafil, sildenafil, ranitidine, famotidine, codeine, fentanyl, tramadol, pseudoephedrine, phenylpropanolamine, dextromethorphan, chlorpheniramine, diphenhydramine, cetirizine, and cimetidine and pharmaceutically acceptable salts thereof.

Preferred therapeutic compounds include combinations of drugs such as paracetamol and tramadol. Without wishing to be bound by theory, it is believed that certain combinations of drugs may result in synergistic dissolution effects. For example, combination of a base and acid may achieve improved dissolution at lower levels of pH modulating agent. Again, without wishing to be bound by theory, it is believed that intrinsic microstirring in the tablet may effectively promote the dissolution of the lesser soluble drug compared with the mixing achieved as a result of the reaction between the base and the acid (of the pH modulating agent) in the dissolution medium.

Preferably, the carbonate is present in an amount from about 1% to about 75% by weight of swallow formulation and in an amount that will neutralise between about 0.01 and 10 millimoles of hydrochloric acid. More preferably the carbonate is present in an amount from about 10% to about 70% by weight in the swallow formulation and in an amount that will neutralise between about 0.02 and 8 millimoles of hydrochloric acid.

Conveniently, when the therapeutic compound is a base, amphoteric or salt or proactive form thereof, the carbonate component of the pH modulating agent is present in an amount from about 1 mg to about 450 mg in the swallow formulation, more preferably 2 mg to 400 mg. Conveniently, when the therapeutic compound is an acid, unionized active or salt or proactive form thereof the carbonate component in the pH modulating agent is present in an amount greater than about 8 mg in the swallow formulation. Examples of particular amounts of carbonate include 8 to 850 mg per swallow formulation. More preferably the carbonate is present in an amount from about 15 mg to 700 mg.

In one swallow formulation embodiment, the carbonate is sodium bicarbonate and/or potassium bicarbonate and is present in an amount from about 5% to 75% by weight of the swallow formulation.

The water uptake agent may be present in an amount from 5% to 95%, or 10% to 90% or more preferably from 20% to 60% by weight of the swallow formulation and more preferably between 30% and 50% by weight of the swallow formulation.

Preferably, the ratio of water uptake agent to pH modulating agent is between 0.1:1 and 20:1. More preferably the ratio of water uptake agent to pH modulating agent is between 0.3:1 and 15:1 or even more preferably between 0.5:1 and 8:1 by weight.

Typically, when the therapeutic compound is an acid, unionized species or a salt thereof at least 70% of the therapeutic compound is dissolved from the swallow formulation within 120 seconds in USP dissolution apparatus 2 with 900 mL 0.0033 N hydrochloric acid at 30 rpm and 37° C. Even more preferably, at least 80% is dissolved in 120 seconds and even more preferably, at least 90% is dissolved in 120 seconds.

Typically, when the therapeutic compound is a base, an amphoteric or a salt thereof at least 50% of the therapeutic compound is dissolved from the swallow formulation within 240 seconds in USP dissolution apparatus 2 with 900 mL 0.0033 N hydrochloric acid at 30 rpm and 37° C. In a preferred embodiment at least 60% of the therapeutic compound is dissolved from the swallow formulation within 300 seconds in USP dissolution apparatus 2 with 900 mL 0.0033 N hydrochloric acid at 30 rpm and 37° C. Even more preferably, at least 60% is dissolved in 240 seconds.

In one embodiment of an acidic compound, the therapeutic compound is ibuprofen. Preferably the carbonate is present in an amount between 5% and 75% by weight of the swallow formulation. More preferably the carbonate is present in an amount between 10% and 70%. More preferably the carbonate is present in an amount between 15 mg and 700 mg. Preferably the bicarbonate is sodium bicarbonate.

In one embodiment the salt of an acidic therapeutic compound is ibuprofen sodium. Preferably the carbonate is present in an amount between 5% and 75% by weight of the swallow formulation. More preferably the carbonate is present in an amount between 10% and 70% by weight of the swallow formulation. More preferably the carbonate is present in an amount between 15 mg and 700 mg. Preferably the bicarbonate is sodium bicarbonate or potassium bicarbonate or a mixture thereof.

In a further embodiment the acidic therapeutic compound is diclofenac. Preferably the bicarbonate is present in an amount between 5% and 75% by weight of the swallow formulation. More preferably the carbonate is present in an amount between 10% and 70% by weight of the swallow formulation. More preferably the carbonate is present in an amount between 15 mg and 700 mg. Preferably the bicarbonate is sodium bicarbonate.

In one embodiment of the invention the therapeutic compound is a basic compound chosen from the group comprising zolmitriptan, alprazolam, lorazepam, diazepam or combinations thereof. Preferably the carbonate is present in an amount between 1% and 50% by weight of the swallow formulation. More preferably the carbonate is present in an amount between 1% and 40%. Preferably the carbonate is present in an amount between 1 mg and 450 mg or more preferably in an amount between 1 mg and 350 mg. Preferably the carbonate is sodium bicarbonate. Optionally the swallow formulation further comprises up to 50% by weight of a pharmaceutically acceptable acid.

In another embodiment of the invention the therapeutic compound is a salt of a basic therapeutic compound chosen from the group comprising sildenafil citrate, pseudoephedrine hydrochloride, eletriptan hydrobromide, rizatriptan benzoate, metoclopramide hydrochloride, loperamide hydrochloride, codeine phosphate, tramadol hydrochloride, zolpidem tartrate, ondansetron hydrochloride or combinations thereof. Preferably the carbonate is present in an amount between 1% and 50% by weight of the swallow formulation. More preferably the carbonate is present in an amount between 1% and 40% by weight of the swallow formulation. Preferably the carbonate is present in an amount between 1 mg and 450 mg, more preferably and amount between 1 mg and 350 mg. Preferably the carbonate is a bicarbonate such as sodium bicarbonate or potassium bicarbonate or a mixture thereof. Optionally the swallow formulation further comprises up to 50% by weight of a pharmaceutically acceptable acid.

In another embodiment the therapeutic compound is an amphoteric compound chosen from the group consisting of cetirizine, lorazepam or combinations thereof. Preferably the carbonate is present in an amount between 1% and 50% by weight of the swallow formulation. More preferably the carbonate is present in an amount between 1% and 40% by weight of the swallow formulation. Preferably the carbonate is present in an amount between 1 mg and 450 mg or more preferably in an amount between 1 mg and 300 mg. Preferably the carbonate is sodium bicarbonate. Optionally the swallow formulation may comprise up to 50% by weight of a pharmaceutically acceptable acid such as tartaric acid.

In another embodiment the therapeutic compound is a salt of an amphoteric compound chosen from the group consisting of fexofenadine hydrochloride, cetirizine hydrochloride or combinations thereof. Preferably the carbonate is present in an amount between 1% and 50% by weight of the swallow formulation. Preferably the carbonate is present in an amount between 1% and 40% by weight of the swallow formulation or more preferably in an amount between 1 mg and 300 mg. More preferably the carbonate is present in an amount between 1 mg and 450 mg. Preferably the carbonate is sodium bicarbonate. Optionally the swallow formulation may comprise up to 50% by weight of a pharmaceutically acceptable acid such as tartaric acid.

Optionally the swallow formulation may also comprise one or more pharmaceutically acceptable excipients or other components such as carriers, glidants, emulsifiers, diluents, binders, preservatives, wicking agents and/or disintegrants.

The swallow formulation may further contain flavouring agents, colouring agents and sweeteners.

In one embodiment the swallow formulation is co-administered with an aqueous fluid such as water. The co-administered fluid may be administered, before, after or with the swallow formulation.

Another aspect of the present invention is directed to a swallow formulation comprising a therapeutic compound that is an acid or a salt of an acid with pH modulating agents that include an appropriate amount of one or more soluble carbonates and which permits at least about 50% of the therapeutic compound to dissolve from the swallow formulation within 300 seconds in USP dissolution apparatus 2 with 900 mL 0.0033 N hydrochloric acid at 30 rpm and 37° C. said dosage form further comprising one or more pharmaceutically acceptable carriers, diluents and/or excipients, wherein the swallow formulation is co-administered with fluid.

The swallow formulation may comprise one or more therapeutic agents.

The swallow formulation may comprise one or more diagnostic agents.

Accordingly, in one preferred embodiment, the present invention provides a swallow formulation comprising two or more therapeutic compounds with pH modulating agents that include one or more carbonates in an appropriate amount wherein at least one of the therapeutic compounds is an acid or a salt of an acid and at least 50% dissolves from the swallow formulation within 300 seconds in USP dissolution apparatus 2 with 900 mL 0.0033 N hydrochloric acid at 30 rpm and 37° C.

In another aspect of the present invention there is provided a dosage form comprising a swallow formulation comprising a therapeutic compound that is an acid, a salt of an acid or an unionized compound with pH modulating agents that include one or more soluble carbonates and wherein at least about 50% of the therapeutic compound is dissolved from the swallow formulation within 300 seconds in USP dissolution apparatus 2 with 900 mL 0.0033 N hydrochloric acid at 30 rpm and 37° C.

In another aspect of the present invention there is provided a dosage form comprising a swallow formulation comprising a therapeutic compound with a volume median diameter ($D_{50}$) below 350 μm and surface area greater than 0.07 $m^2 \cdot g^{-1}$ with pH modulating agents that include one or more soluble carbonates and wherein at least about 50% of the therapeutic compound is dissolved from the swallow formulation within 300 seconds in USP dissolution apparatus 2 with 900 mL 0.0033 N hydrochloric acid at 30 rpm and 37° C.

The dosage form may be a tablet, capsule, powder or other unit presentation.

The dosage form of the present invention may be a coated, uncoated and/or layered tablet.

Suitable coatings include water soluble polymer based coatings such as polyvinyl alcohol (PVA), povidone or hypromellose. Suitable coating polymers may also be a derivative of cellulose (cellulose acetophthalate, hypromellose phthalate) or a derivative of an acrylic polymer (methacrylate acid copolymer). The dosage form may contain one or more further pharmaceutically active agents.

In another embodiment, the dosage form is a multi-phase release dosage form containing a further therapeutic compound having a dissolution of less than 70% in 180 seconds in USP dissolution apparatus 2 with 900 mL 0.0033 N hydrochloric acid at 30 rpm and 37° C.

Fasted Versus Fed State

One of the surprising aspects of the formulations of the present invention is their performance in vitro under conditions that represent the fed as well as in the fasted state. For example, compositions of the present invention have been tested to assess the effect of sodium bicarbonate and sodium bicarbonate/acid combinations on the dissolution rate of actives under neutral conditions such as in milk that better approximates the fed state, or in water that better approximates conditions where gastric acid is not present or has been neutralised. These results have been compared with dissolution in 0.015 N hydrochloric acid, which approximates the fasted state.

In a particularly preferred embodiment the formulations of the present invention exhibit effective dissolution in both fed and fasted states in vivo. Furthermore, it is preferred that the microstirring of the formulations exhibit a faster rate of dissolution in the fed state compared with products that do not produce microstirring, such as those currently commercially available.

With respect to the dissolution testing described herein, the paddle speed could be viewed as an analogue to the different degrees of gastric motility that occur during the gastric emptying cycle. For example, the paddle speed of 0 rpm approximates to low gastric motility and the faster paddle speed of 30 rpm could more closely approximate to higher gastric motility.

Other Aspects of the Invention

Swallow formulations of the present invention may be manufactured by admixing the ingredients simultaneously or sequentially and then converting into a dosage unit such as a tablet, capsule or the like.

Tablets of the present invention may be manufactured by direct compression or by granulation of one or more components, dry blending and then compression.

The present invention further contemplates a method for the amelioration or prevention of the symptoms associated with a disease or disorder, including pain, fever, inflammation, discomfort, migraine, infections, musculoskeletal system, respiratory conditions, allergic reactions, nausea, gastrointestinal disorders, alimentary system, endocrine system, insomnia, sleep disorders, neoplasms, bone disease, osteoporosis, blood disorders, cardiovascular system, immune system, genitourinary system, central nervous system, hormonal conditions, metabolic disorders and nutritional deficiencies in a subject, the method comprising administering to said subject a swallow formulation comprising a therapeutic compound that is an acid, a salt of an acid or an unionized compound and one or more soluble bicarbonates, the therapeutic compound having enhanced dissolution from the swallow formulation, the administration being for a time and under conditions to prevent or ameliorate symptoms of the condition.

Conditions contemplated herein include any condition associated with a disease or disorder in need of treatment. Conditions include but are not limited to conditions associated with pain, fever, inflammation, discomfort, migraine, infections, musculoskeletal system, respiratory conditions, allergic reactions, nausea, gastrointestinal disorders, alimentary system, endocrine system, insomnia, sleep disorders, neoplasms, bone disease, osteoporosis, blood disorders, cardiovascular system, immune system, genitourinary system, nervous system, hormonal disorders, skin disorders, metabolic disorders and nutritional deficiencies, and conditions requiring hormonal and steroidal treatment.

Another aspect of the present invention contemplates a method for management of a condition in a subject experiencing the condition or anticipating to experience the condition, said method comprising administering to said subject an oral delivery system comprising a therapeutic compound chosen from the group comprising acids, bases, amphoterics, unionized compounds, their salts, their proactive forms and mixtures thereof to treat the condition with pH modulating agents that include one or more soluble carbonates, the therapeutic compound having enhanced dissolution from the swallow formulation, the administration being for a time and under conditions to prevent or ameliorate symptoms of the condition.

Another aspect of the present invention contemplates a method for diagnosing a condition in a subject experiencing the condition or anticipating to experience the condition, said method comprising administering to said subject an oral delivery system comprising a diagnostic agent chosen from the group comprising acids, bases, amphoterics, unionized compounds, their salts, their proactive forms and mixtures thereof to diagnose the condition with pH modulating agents that include one or more soluble bicarbonates, the diagnostic agent having enhanced dissolution from the swallow formulation, the administration being for a time and under conditions to diagnose the condition.

These methods may also involve the oral dosage form having one or more pharmaceutically acceptable excipients.

EXAMPLES

The present invention is further described by the following non-limiting examples which relate to the following acid, unionized, basic and amphoteric actives and their salts. All examples include a formulation with bicarbonate in accordance with the present invention. Comparative dissolution data are provided for commercial products sourced in Australia or USA.

Examples 1 to 14 relate to the following acid or unionized actives or salts thereof
1. Ibuprofen sodium 226 mg alone and 113 mg ibuprofen sodium with 100 mg ibuprofen (acid salt and acid)
2. Ibuprofen 200 mg (acid)
3. Diclofenac potassium 50 mg (acid salt)
4. Paracetamol 100 mg & 500 mg (unionized)
5. Naproxen 250 mg (acid)
6. Naproxen sodium 275 mg (acid salt)
7. Gemfibrozil 600 mg (acid)
8. Furosemide 40 mg (acid)
9. Temazepam 10 mg (unionized)
10. Montelukast sodium 10.4 mg (acid salt)
11. Prednisolone 5 mg & 25 mg (unionized)
12. Dexamethasone 4 mg (unionized)
13. Comparative dissolution data for actives of Examples 1 to 12
14. Comparative solubility data for actives of Examples 1 to 12

Examples 15 to 31 relate to the following basic or amphoteric actives or salts thereof:
15. Fexofenadine hydrochloride 180 mg (salt of amphoteric drug)
16 Pseudoephedrine hydrochloride 60 mg (salt of basic drug)
17 Eletriptan hydrobromide 40 mg (base) (salt of basic drug)
18 Rizatriptan benzoate 14.53 mg (salt of basic drug)
19 Metoclopramide hydrochloride 10 mg (salt of basic drug)
20 Loperamide hydrochloride 2 mg (salt of basic drug)
21 Codeine phosphate 30 mg (salt of basic drug)
22 Tramadol hydrochloride 37.5 mg (salt of basic drug)
23 Diazepam 5 mg (basic)
24 Lorazepam 2.5 mg (amphoteric)
25 Alprazolam 1 mg (basic)
26 Sildenafil citrate 140 mg (salt of a basic drug)
27 Ondansetron hydrochloride 10 mg (salt of a basic drug)
28 Zolmitriptan 2.5 mg (base)
29 Zolpidem tartrate 10 mg (salt of a basic drug)
30 Cetirizine hydrochloride 10 mg (salt of an amphoteric drug)
31 Comparative solubility data for Examples 15 to 30

Examples 32 and 33 relate to granulated formulations of the unionized drug paracetamol alone and in a combination formulation containing paracetamol 325 mg with the salt of a basic drug, tramadol hydrochloride 37.5 mg.

Examples 34-36 relate to the dissolution of ibuprofen (acid), paracetamol (unionized) and zolpidem tartrate (salt of a basic drug) in neutral dissolution media such as water and milk.

Dissolution Testing

The following USP dissolution apparatus 2 with 1000 mL dissolution vessels and paddle stirrers was used to perform the dissolution testing:
VanKel VK 7010 Dissolution bath
VanKel VK 750 D Heater/Circulator
Gilson Minipuls peristaltic pump for automatic continuous sampling Testing was conducted in a dissolution medium containing 900 mL 0.0033 N hydrochloric acid (HCl) at 37° C. which discriminates better between fast dissolving formulations than more acidic dissolution media where the effect of high acid concentration tends to mask formulation effects on dissolution. 900 mL of this medium contains the absolute amount of acid estimated to be present in the gastric contents in vivo, namely 3 millimoles.

This amount of acid can be completely neutralized by high amounts of bases used as pH modulating agents in examples of this present invention, so that the pH of the dissolution medium will change depending on the levels of pH modulating agents used. This is particularly important for investigating the dissolution of drugs where their solubility is pH dependent. For example, the solubility of a base or its salt such as tramadol hydrochloride is reduced as the pH increases, whereas the solubility of an acid or its salt such as ibuprofen is reduced as the pH increases. In contrast, the solubility of the unionized drug paracetamol is independent of the pH.

When the stirring speed is reduced to 0 rpm, the dissolution profiles demonstrate the intrinsic characteristics of the fast dissolving formulations of this invention which are able to enhance the dissolution of the drugs without any external stirring. Dissolution results without stirring may be of in vivo significance in conditions where there is gut stasis or reduced gastric activity.

Dissolution media were prepared by diluting an appropriate volume of 32% w/w concentrated hydrochloric acid (HCl) (AR quality from Rowe Scientific) with purified water from an in-house Millipore Elix® water system.

Dissolution results were measured as the mean of 2 replicates.

Testing at was conducted at a stirring speed of 30 rpm and also at 0 rpm which provides more discrimination between formulations. To achieve maximum dissolution, the stirring speed was increased to 250 rpm for 10 minutes after 20 minutes for measurements at 30 rpm, and after 60 minutes for measurements at 0 rpm.

Unless otherwise stated, drug concentrations were measured using a Varian Cary 50 UV-Vis Spectrophotometer set at an appropriate wavelength using flow through cells for automatic continuous sampling. For each drug, the optimal wavelength was selected after running UV scans in the dissolution medium.

For drug concentration measurements at 0 rpm, the amount of dissolution medium circulating through the spectrophotometer was so small as to have negligible effect on the main body of dissolution media.

Drug concentrations for the paracetamol/tramadol formulations of Example 33 and paracetamol and zolpidem tartrate formulations tested in milk of Example 35 and 36 were measured by HPLC analysis in samples taken at selected intervals.

HPLC analyses were conducted using Waters equipment comprising a 501 or 510 pump with a 969 photodiode array or 486 absorbance detector, 717 with auto sampler and sample cooler. A suitable C18 column and guard column were used. Results were processed using Waters Empower software.

Solution pH was measured using a TPS WP81 pH, Salinity, Temperature & Conductivity Meter.

In Vitro In Vivo Correlation (IVIVC)

While scintigraphy is the gold standard for measuring gastric emptying, paracetamol is widely recognised and used as a marker for gastric emptying. Based on the correlation between in vivo results obtained with paracetamol and in vitro dissolution results, it is anticipated that the enhanced in vitro dissolution demonstrated by the present invention will be associated with faster dissolution in vivo leading to faster absorption in vivo.

In a series of multiple 5 subject crossover studies, the effect of a range of different formulations containing different alkali agents on in vivo absorption were investigated. Subjects were fasted overnight and dosed with two tablets each containing 500 mg paracetamol. Plasma levels of paracetamol were monitored for 8 hours, with 10 samples taken in the first hour. Table 1 summarises the median partial AUC at 20 minutes (AUC20) for formulations showing improved absorption of paracetamol with formulations containing a wide range of sodium bicarbonate levels compared with magnesium carbonate, even at lower neutralising capacities.

TABLE 1

Effect of Different Alkaline Agents on Paracetamol Absorption In Vivo

| Alkaline agent | None | Sodium bicarbonate | | | | Magnesium carbonate | |
|---|---|---|---|---|---|---|---|
| Dose (mg) | 0 | 200 | 400 | 800 | 1200 | 150 | 300 |
| Neutralising capacity of formulation (millimoles) | 0 | 2.0 | 4.8 | 8.0 | 12.0 | 3.1 | 6.1 |
| Median AUC20 (min · mg · L$^{-1}$) | 95.4 | 228.6 | 285.8 | 264.0 | 160.5 | 68.6 | 120.5 |

In a study on rapidly absorbed paracetamol tablets in 25 healthy fasted human subjects carried out by the applicant, an in vitro in vivo correlation (IVIVC) was established between the AUC10 ($R^2$=0.91) and AUC20 ($R^2$=0.87) for paracetamol and the in vitro % drug dissolved in 300 seconds in USP apparatus 2 with 900 mL 0.0033 N hydrochloric acid at 30 rpm and 37° C. This quantity of dissolution medium contains 3 millimoles of hydrochloric acid.

Given these correlations, preferred in vitro dissolution target rates were set based on measurements using USP apparatus 2 with 900 mL 0.0033 N hydrochloric acid at 30 rpm and 37° C. The preferred target rates were greater than 50% dissolution at 300 seconds, greater than 40% dissolution in 240 seconds, or more preferably greater than 20% dissolution at 180 seconds.

Formulations

Where the drug substance per se was commercially available, test samples were prepared by dry blending the ingredients prior to compression unless otherwise stated in the examples. The powder blend was compressed with suitable size tooling on a rotary press to produce tablets with hardness in the range 3-12 Kp. The volume median diameter ($D_{50}$) of the therapeutic compounds was less than 350 μm and the surface area was greater than 0.07 m$^2$·g$^{-1}$.

Where the drug substance per se was not commercially available, test formulations were prepared by reformulation of commercial product. Purchased tablets were crushed in a mortar and pestle, and passed through a 500 μm or 280 μm screen to remove the majority of any film coating. The resultant powder was dry blended proportionally with other ingredients before compression.

While the complete quantitative formulations of the commercial products are not known, all ingredients contained in the products are listed in the product information available from the manufacturer. The amount of drug and any actives are quantified, but only the presence or absence of other ingredients is known. In the tables for these examples, the symbol "√" indicates that a specific ingredient is present, and will be present at the same level in all formulations provided.

Although these formulations have not been optimised, they do demonstrate the applicability of the present invention to a range of different acidic compounds, salts of acid compounds and unionized compounds.

Examples 1 to 10

Overview of Examples 1 to 10

All examples are either unionized drugs or drugs containing acidic groupings, that demonstrate faster in vitro dissolution when combined with a bicarbonate in accordance with the present invention.

Example 1 is a combination of a salt of an acid and an acid. Examples 2, 5, 7 and 8 are acids. Examples 3, 6 and 10 are salts of acids. Examples 4 and 9 are unionized drugs where Example 4 is paracetamol, an unionized compound for which good in vitro in vivo correlation (IVIVC) has been established.

Tables 2 to 21 set out the formulations and their corresponding dissolution rates. FIGS. 1 to 10 depict graphically the dissolution results in 900 mL 0.0033 N hydrochloric acid at 30 rpm.

Conclusions and Further Comments Based on the Examples

It will be apparent that the use of bicarbonates in accordance with the present invention substantially increases in vitro dissolution of the therapeutic agents exemplified compared with the use of other antacids that cause a similar increase in pH of the dissolution medium. In those examples, improved dissolution is evident at lower pH values than those achieved with other antacids.

Example 1

A Mixture of an Acidic Compound and its Salt

TABLE 2

Ibuprofen Sodium/Ibuprofen Formulations

| | Formulation | |
|---|---|---|
| | 1 | 2 |
| Sodium bicarbonate (mg) | 0 | 400 |
| Microcrystalline cellulose (mg) | 714 | 327 |
| Croscarmellose sodium (mg) | 100 | 50 |
| Ibuprofen sodium (mg) | 226 | 113 |
| Ibuprofen (mg) | 0 | 100 |
| Magnesium stearate (mg) | 10 | 10 |
| Total (mg) | 1050 | 1000 |
| Bicarbonate (%) | 0 | 40 |

TABLE 3

Ibuprofen dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 120 sec | 4 | 26 | 0 |
| 180 sec | 6 | 45 | 0 |
| 240 sec | 6 | 69 | 0 |
| 300 sec | 7 | 84 | 0 |
| Final pH | 2.4 | 6.0 | 2.3 |

Example 2

An Acidic Compound

TABLE 4

Ibuprofen Formulations

| | Formulation | | |
|---|---|---|---|
| | 1 | 2 | 3 |
| Sodium bicarbonate (mg) | 0 | 400 | 600 |
| Microcrystalline cellulose (mg) | 740 | 340 | 540 |
| Croscarmellose sodium (mg) | 50 | 50 | 50 |
| Ibuprofen (mg) | 200 | 200 | 200 |
| Magnesium stearate (mg) | 10 | 10 | 10 |
| Total (mg) | 1000 | 1000 | 1400 |
| Bicarbonate (%) | 0 | 40 | 43 |

TABLE 5

Ibuprofen dissolution data in 900 mL 0.0033 N HCl at 30 rpm

| | % drug dissolved in 900 mL 0.0033 N HCl at 30 rpm Formulation | | | |
|---|---|---|---|---|
| | 1 | 2 | 3 | Commercial product |
| 120 sec | 1 | 41 | 70 | 0 |
| 180 sec | 1 | 66 | 85 | 0 |
| 240 sec | 1 | 72 | 87 | 0 |
| 300 sec | 2 | 74 | 88 | 0 |
| Final pH | 2.6 | 5.9 | 6.4 | 2.3 |

Example 3

A Salt of an Acidic Compound

This example includes two comparative formulations, 3 and 4, where high pH is achieved with sodium carbonate, another antacid, but where significantly improved dissolution is not demonstrated in the absence of bicarbonate.

TABLE 6

Diclofenac Potassium Formulations

| | Formulation | | | |
|---|---|---|---|---|
| | 1 | 2 | 3 | 4 |
| Diclofenac potassium (mg) | 50 | 50 | 50 | 50 |
| Sodium bicarbonate (mg) | 0 | 600 | 0 | 0 |
| Sodium carbonate (mg) | 0 | 0 | 443 | 443 |
| Microcrystalline cellulose (mg) | 702 | 290 | 397 | 397 |
| Sodium starch glycolate (mg) | 40 | 50 | 50 | 50 |
| Crospovidone (mg) | 0 | 0 | 50 | 0 |
| Starch 1500 (mg) | 0 | 0 | 0 | 50 |
| Magnesium stearate (mg) | 8 | 10 | 10 | 10 |
| Total (mg) | 800 | 1000 | 1000 | 1000 |
| Bicarbonate (%) | 0 | 60 | 0 | 0 |

TABLE 7

Diclofenac Potassium dissolution data in 900 mL 0.0033 N HCl at 30 rpm

| | % drug dissolved in 900 mL 0.0033 N HCl | | | | |
|---|---|---|---|---|---|
| Formulation | 1 | 2 | 3 | 4 | Commercial product |
| 120 sec | 11 | 20 | 8 | 1 | 0 |
| 180 sec | 12 | 57 | 11 | 4 | 0 |
| 240 sec | 12 | 71 | 13 | 6 | 0 |
| 300 sec | 11 | 75 | 15 | 8 | 0 |
| Final pH | 2.4 | 6.6 | 6.8 | 6.4 | 2.5 |

Example 4

An Unionized Compound

This example compares two formulations of the present invention, one using a bicarbonate alone (Formulation 2) and the other using a bicarbonate in combination with an organic acid (Formulation 3) with a standard tablet containing neither (Formulation 1).

TABLE 8

Paracetamol Formulations

| | Formulation | | |
|---|---|---|---|
| | 1 | 2 | 3 |
| Paracetamol, micronised (mg) | 100 | 500 | 500 |
| Sodium bicarbonate (mg) | 0 | 200 | 200 |
| Citric acid (mg) | 0 | 0 | 75 |
| Microcrystalline cellulose (mg) | 270 | 0 | 0 |
| Povidone K30 (mg) | 0 | 40 | 34 |
| Crospovidone (mg) | 25 | 100 | 100 |
| Starch 1500 (mg) | 0 | 50 | 50 |
| Magnesium stearate (mg) | 5 | 0 | 0 |
| Stearic acid (mg) | 0 | 9 | 9 |
| Total (mg) | 400 | 899 | 968 |
| Bicarbonate (%) | 0 | 22 | 21 |

Methods

Formulation 2 was prepared by granulating the paracetamol, Starch 1500, Povidone K30 and 40% of the Crospovidone with the equivalent of 170 mg deionized water per tablet. The wet mass was screened through a 1.7 mm mesh and dried to less than 2% w/w moisture content. The dry granules were screened through a 355 µm mesh and blended with the sodium bicarbonate and magnesium stearate prior to compression.

Two granules were prepared for Formulation 3. One contained 250 mg Paracetamol, 75 mg citric acid, 25 mg Starch 1500, 20 mg Povidone K30 and 20 mg Crospovidone granulated with the equivalent of 50 mg deionized water per tablet. The second granule contained 250 mg Paracetamol, 25 mg Starch 1500, 14 mg Povidone K30 and 20 mg Crospovidone granulated with the equivalent of 125 mg deionized water per tablet. Both granules were wet screened through a 1.7 mm mesh and dried to less than 2% w/w moisture content. The dry granules were screened through a 1 mm mesh and blended proportionally with the equivalent of 60 mg Crospovidone and 9 mg stearic acid per tablet prior to compression.

TABLE 9

Paracetamol dissolution data in 900 mL 0.0033 N HCl at 30 rpm

| | % drug dissolved in 900 mL 0.0033 N HCl at 30 rpm Formulation | | |
|---|---|---|---|
| | 1 | 2 | 3 |
| 120 sec | 18 | 54 | 69 |
| 180 sec | 27 | 71 | 82 |
| 240 sec | 34 | 78 | 86 |
| 300 sec | 40 | 81 | 88 |
| Final pH | 2.3 | 2.9 | 2.8 |

Example 5

An Acidic Compound

Formulation 1 was prepared by reformulation of commercial product.

TABLE 10

Naproxen Formulation

| | Formulation | |
|---|---|---|
| | 1 | Commercial Product |
| Naproxen (mg) | 250 | 250 |
| Sodium bicarbonate (mg) | 400 | 0 |
| Microcrystalline cellulose (mg) | 242 | 0 |
| Croscarmellose sodium, povidone K30, magnesium stearate, iron oxide yellow | ✓ | ✓ |
| Total (mg) | 950 | 268 |
| Bicarbonate (%) | 42 | 0 |

TABLE 11

Naproxen dissolution data in 900 mL 0.0033 N HCl at 30 rpm

| | % drug dissolved in 900 mL 0.0033 N HCl at 30 rpm Formulation | |
|---|---|---|
| | 1 | Commercial product |
| 120 sec | 58 | 0 |
| 180 sec | 78 | 1 |
| 240 sec | 87 | 2 |
| 300 sec | 90 | 3 |
| Final pH | 6.3 | 2.3 |

Example 6

A Salt of an Acidic Compound

This example contains two formulations prepared by reformulation of commercial product. to demonstrate the improved dissolution by adding an organic acid to the bicarbonate. Formulation 1 contains bicarbonate with an organic acid. Formulation 2 contains bicarbonate only.

TABLE 12

Naproxen Sodium Formulations

| | Formulation | | |
|---|---|---|---|
| | 1 | 2 | Commercial product |
| Naproxen sodium (mg) | 275 | 275 | 275 |
| Sodium bicarbonate (mg) | 500 | 500 | 0 |
| Crospovidone (mg) | 50 | 50 | 0 |
| Citric acid anhydrous (mg) | 76 | 0 | 0 |
| Microcrystalline cellulose, talc, povidone K30, magnesium stearate | ✓ | ✓ | ✓ |
| Total (mg) | 1126 | 1050 | 400 |
| Bicarbonate (%) | 44 | 48 | 0 |

TABLE 13

Naproxen Sodium dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 120 sec | 21 | 15 | 1 |
| 180 sec | 37 | 27 | 6 |
| 240 sec | 69 | 40 | 10 |
| 300 sec | 86 | 52 | 13 |
| Final pH | 6.2 | 6.4 | 2.5 |

Example 7

An Acidic Compound

This example was prepared by reformulation of commercial product.

TABLE 14

Gemfibrozil Formulation

| | Formulation | |
|---|---|---|
| | 1 | Commercial product |
| Gemfibrozil (mg) | 600 | 600 |
| Sodium bicarbonate (mg) | 500 | 0 |
| Microcrystalline cellulose, silica, calcium stearate, pregelatinised maize starch, hydroxy propyl cellulose, macrogol 3350, polysorbate 80, methyl hydroxybenzoate, hypromellose, candelilla wax, opaspray white | ✓ | ✓ |
| Crospovidone (mg) | 50 | 0 |
| Total (mg) | 1420 | 870 |
| Bicarbonate (%) | 35 | 0 |

TABLE 15

Gemfibrozil dissolution data in 900 mL 0.0033 N HCl at 30 rpm

| | % drug dissolved in 900 mL 0.0033 N HCl at 30 rpm Formulation | |
|---|---|---|
| | 1 | Commercial product |
| 120 sec | 35 | 0 |
| 180 sec | 45 | 0 |
| 240 sec | 51 | 0 |
| 300 sec | 56 | 0 |
| Final pH | 6.3 | 2.3 |

Example 8

An Acidic Compound

This example was prepared by reformulation of commercial product.

TABLE 16

Furosemide Formulation

| | Formulation | |
|---|---|---|
| | 1 | Commercial product |
| Furosemide (mg) | 40 | 40 |
| Sodium bicarbonate (mg) | 400 | 0 |
| Microcrystalline cellulose (mg) | 300 | 0 |
| Crospovidone (mg) | 50 | 0 |
| Lactose, maize starch, pregelatinised maize starch, magnesium stearate | ✓ | ✓ |
| Total (mg) | 910 | 160 |
| Bicarbonate (%) | 44 | 0 |

TABLE 17

Furosemide dissolution data in 900 mL 0.0033 N HCl at 30 rpm

| | % drug dissolved in 900 mL 0.0033 N HCl at 30 rpm Formulation | |
|---|---|---|
| | 1 | Commercial product |
| 120 sec | 85 | 0 |
| 180 sec | 86 | 0 |
| 240 sec | 87 | 1 |
| 300 sec | 87 | 1 |
| Final pH | 6.2 | 2.3 |

Example 9

An Unionized Compound

This example was prepared by reformulation of commercial product.

TABLE 18

Temazepam Formulation

| | Formulation | |
|---|---|---|
| | 1 | Commercial product |
| Temazepam (mg) | 10 | 10 |
| Sodium bicarbonate (mg) | 20 | 0 |
| Citric acid (mg) | 10 | 0 |

TABLE 18-continued

Temazepam Formulation

| | Formulation | |
|---|---|---|
| | 1 | Commercial product |
| Crospovidone (mg) | 10 | 0 |
| Microcrystalline cellulose, lactose, maize starch, sunset yellow lake, magnesium stearate | ✓ | ✓ |
| Total (mg) | 218 | 178 |
| Bicarbonate (%) | 9 | 0 |

TABLE 19

Temazepam dissolution data in 900 mL 0.0033 N HCl at 30 rpm

| | % drug dissolved in 900 mL 0.0033 N HCl at 30 rpm Formulation | |
|---|---|---|
| | 1 | Commercial product |
| 120 sec | 50 | 0 |
| 180 sec | 62 | 1 |
| 240 sec | 69 | 1 |
| 300 sec | 74 | 1 |
| Final pH | 2.3 | 2.3 |

Example 10

A Salt of an Acidic Compound

Both formulations were prepared by reformulating commercial product and show increased pH and enhanced dissolution compared with the commercial product. Formulation 2 demonstrates the use of citric acid with a higher level of bicarbonate to achieve faster dissolution than using sodium bicarbonate alone, Formulation, 1.

TABLE 20

Montelukast Sodium Formulations

| | Formulation | | |
|---|---|---|---|
| | 1 | 2 | Commercial product |
| Montelukast sodium (mg) | 10.4 | 10.4 | 10.4 |
| Sodium bicarbonate (mg) | 400 | 600 | 0 |
| Citric acid anhydrous (mg) | 0 | 76 | 0 |
| Microcrystalline cellulose, croscarmellose sodium, lactose, magnesium stearate, film coating agents | ✓ | ✓ | ✓ |
| Total (mg) | 700 | 1016 | 204 |
| Bicarbonate (%) | 57 | 59 | 0 |

TABLE 21

Montelukast Sodium dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 120 sec | 0 | 84 | 3 |
| 180 sec | 5 | 81 | 3 |
| 240 sec | 10 | 80 | 2 |
| 300 sec | 14 | 80 | 2 |
| Final pH | 6.5 | 6.6 | 2.3 |

Examples 11 & 12

The present invention is further described by the following additional non-limiting examples which relate to the following unionized actives—prednisolone and dexamethasone.

Examples 11 and 12 contain dissolution profiles determined at 30 rpm and 0 rpm for:
- a formulation designated 1 or 3 containing bicarbonate alone in accordance with the present invention
- a formulation designated 2 or 4 containing bicarbonate & acid in accordance with the present invention
- a commercial product without bicarbonate sourced in Australia as a comparative example Overview of Results Table 22 and Table 23 summarise the dissolution results for prednisolone and dexamethasone at 30 rpm and 0 rpm respectively.

Tables 24 to 29 set out the formulations and corresponding dissolution data at both 30 rpm and 0 rpm.

The corresponding dissolution data at 30 rpm and 0 rpm for prednisolone and dexamethasone are shown in FIGS. 22-27.

Conclusions and Further Comments Based on the Examples

It will be apparent that the use of bicarbonates in accordance with the present invention substantially increases in vitro dissolution of the therapeutic agents exemplified.

Table 22 summarises the dissolution data for formulations that demonstrate the present invention in 900 mL 0.0033 N hydrochloric acid in USP apparatus 2 at 30 rpm and 37° C.:

TABLE 22

Dissolution data for Prednisolone and Dexamethasone in formulations according to the invention at 30 rpm stirring speed in 900 mL 0.0033 N HCl

| Product and Drug | % drug dissolved in 900 mL 0.0033 N HCl at 30 rpm | | | |
|---|---|---|---|---|
| | 120 sec | 180 sec | 240 sec | 300 sec |
| Commercial Prednisolone 5 mg | 34 | 42 | 46 | 50 |
| Prednisolone 5 mg 11-1 | 9 | 14 | 19 | 23 |
| Prednisolone 5 mg 11-2 | 69 | 78 | 81 | 83 |
| Commercial Prednisolone 25 mg | 5 | 10 | 14 | 20 |
| Prednisolone 25 mg 11-3 | 14 | 21 | 24 | 26 |
| Prednisolone 25 mg 11-4 | 77 | 82 | 85 | 86 |
| Commercial Dexamethasone 4 mg | 4 | 13 | 17 | 23 |
| Dexamethasone 4 mg 12-1 | 24 | 40 | 47 | 54 |
| Dexamethasone 4 mg 12-2 | 61 | 71 | 76 | 79 |

With the exception of prednisolone formulated with sodium bicarbonate alone (11-1 and 11-3), all formulations according to the invention had a dissolution rate greater than 50% at 300 seconds at 30 rpm.

While the commercial 5 mg prednisolone tablet which contains no pH modulating agents also reached 50% dissolution and performed better than 11-1, it should be noted that no formulation optimisation has been conducted. It is expected that better performing examples could be formulated according to the present invention.

Reducing the dissolution limit to more than 60% at 300 seconds, all formulations containing bicarbonate with an acid meet this specification, whereas those containing bicarbonate alone do not.

Similarly for the limits of 50% dissolution at 240 seconds and 60% at 240 seconds.

Table 23 summarises the dissolution data for formulations that demonstrate the present invention in 900 mL 0.0033 N hydrochloric acid using USP apparatus 2 at 0 rpm and 37° C.:

TABLE 23

Dissolution data for Prednisolone and Dexamethasone in formulations according to the invention at 0 rpm stirring speed in 900 mL 0.0033 N HCl

| Drug | % drug dissolved in 900 mL 0.0033 N HCl at 0 rpm | | |
|---|---|---|---|
| | 300 sec | 15 min | 30 min |
| Prednisolone 5 mg 11-1 | 1 | 5 | 11 |
| Prednisolone 5 mg 11-2 | 75 | 89 | 97 |
| Prednisolone 25 mg 11-3 | 3 | 7 | 9 |
| Prednisolone 25 mg 11-4 | 69 | 86 | 95 |
| Dexamethasone 4 mg 12-1 | 4 | 7 | 10 |
| Dexamethasone 4 mg 12-2 | 57 | 90 | 99 |

It will be apparent that the use of bicarbonates in accordance with the present invention substantially increases in vitro dissolution of the therapeutic agents exemplified under no stir conditions highlighting the role of microstirring in enhancing dissolution.

It is clear from these results that
- all formulations containing bicarbonate alone had a dissolution rate greater than 5% at 30 minutes at 0 rpm.
- all formulations containing bicarbonate with a pharmaceutically acceptable acid had a dissolution rate greater than 5% at 300 seconds at 0 rpm.

Example 11

An Unionized Compound

TABLE 24

Prednisolone 5 mg and 25 mg Formulations

| | Formulation | | | | | |
|---|---|---|---|---|---|---|
| | 11-1 | 11-2 | Commercial Product | 11-3 | 11-4 | Commercial Product |
| Prednisolone (mg) | 5 | 5 | 5 | 25 | 25 | 25 |
| Sodium bicarbonate (mg) | 20 | 20 | 0 | 40 | 40 | 0 |
| Fumaric acid (mg) | 0 | 14 | 0 | 0 | 28 | 0 |
| Microcrystalline cellulose (mg) | 80 | 70 | 0 | 80 | 80 | 0 |
| Crospovidone (mg) | 10 | 10 | ✓ | 13 | 14 | ✓ |
| Povidone, maize starch, lactose | 0 | 0 | ✓ | 0 | 0 | ✓ |
| Magnesium stearate (mg) | 1.2 | 1.2 | ✓ | 1.5 | 1.6 | ✓ |
| Total (mg) | 116.2 | 120.2 | 141 | 159.5 | 188.6 | 182 |
| Bicarbonate (%) | 17.2 | 16.6 | 0 | 25.1 | 21.2 | 0 |

TABLE 24-continued

Prednisolone 5 mg and 25 mg Formulations

| | Formulation | | | | | |
|---|---|---|---|---|---|---|
| | 11-1 | 11-2 | Commercial Product | 11-3 | 11-4 | Commercial Product |
| Hardness (Kp) | 10 | 8 | — | 8 | 10 | — |
| Disintegration time in 0.0033 N HCl (Sec) | 35 | 57 | 143 | 10 | 49 | 330 |

Formulations were compressed using 8 mm round shallow concave punches.

The commercial products were uncoated round tablets with a break-bar. The 5 mg tablet was flat bevelled edge with a diameter of 6.5 mm, and the 25 mg tablet was shallow convex with a diameter of 10 mm.

TABLE 25

Prednisolone dissolution data in 900 mL 0.0033 N HCl at 30 rpm

| | % drug dissolved in 900 mL 0.0033 N HCl at 30 rpm Formulation | | | | | |
|---|---|---|---|---|---|---|
| | 11-1 | 11-2 | Commercial product | 11-3 | 11-4 | Commercial product |
| | Dose | | | | | |
| | 5 mg | | | 25 mg | | |
| 120 sec | 9 | 69 | 34 | 14 | 77 | 5 |
| 180 sec | 14 | 78 | 42 | 21 | 82 | 10 |
| 240 sec | 19 | 81 | 46 | 24 | 85 | 14 |
| 300 sec | 23 | 83 | 50 | 26 | 86 | 20 |
| Final pH | 2.3 | 2.3 | 2.3 | 2.3 | 2.3 | 2.3 |

TABLE 26

Prednisolone dissolution data in 900 mL 0.0033 N HCl at 0 rpm

| | % drug dissolved in 900 mL 0.0033 N HCl at 0 rpm Dose | | | |
|---|---|---|---|---|
| | 5 mg | | 25 mg | |
| | Formulation | | | |
| | 11-1 | 11-2 | 11-3 | 11-4 |
| 300 sec | 1 | 75 | 3 | 69 |
| 15 min | 5 | 89 | 7 | 86 |
| 30 min | 11 | 97 | 9 | 95 |
| Final pH | 2.3 | 2.3 | 2.4 | 2.3 |

Example 12

An Unionized Compound

These formulations were prepared by reformulation of commercial product.

TABLE 27

Dexamethasone Formulations

| | Formulation | | |
|---|---|---|---|
| | 12-1 | 12-2 | Commercial Product |
| Dexamethasone (mg) | 4 | 4 | 4 |
| Sodium bicarbonate (mg) | 40 | 40 | 0 |

TABLE 27-continued

Dexamethasone Formulations

| | Formulation | | |
|---|---|---|---|
| | 12-1 | 12-2 | Commercial Product |
| Fumaric acid (mg) | 0 | 28 | 0 |
| Microcrystalline cellulose (mg) | 100 | 100 | 0 |
| Crospovidone (mg) | 25 | 25 | 0 |
| Lactose, povidone, maize starch | ✓ | ✓ | ✓ |
| Magnesium stearate (mg) | ✓ + 2 | ✓ + 2 | ✓ |
| Total (mg) | 356 | 384 | 189 |
| Bicarbonate (%) | 11.2 | 10.4 | 0 |
| Hardness (Kp) | 9 | 10 | — |
| Disintegration time in 0.0033 N HCl (Sec) | 76 | 38 | 360 |

Formulations were compressed using 15 mm×5 mm oval shaped shallow concave punches.

The commercial product was a 8 mm uncoated round flat tablet with a break-bar.

TABLE 28

Dexamethasone dissolution data in 900 mL 0.0033 N HCl at 30 rpm

| | % drug dissolved in 900 mL 0.0033 N HCl at 30 rpm Formulation | | |
|---|---|---|---|
| | 12-1 | 12-2 | Commercial Product |
| 120 sec | 24 | 61 | 4 |
| 180 sec | 40 | 71 | 13 |
| 240 sec | 47 | 76 | 17 |
| 300 sec | 54 | 79 | 23 |
| Final pH | 2.4 | 2.4 | 2.3 |

TABLE 29

Dexamethasone dissolution data in 900 mL 0.0033 N HCl at 0 rpm

| | % drug dissolved in 900 mL 0.0033 N HCl at 0 rpm Formulation | |
|---|---|---|
| | 12-1 | 12-2 |
| 300 sec | 4 | 57 |
| 15 min | 7 | 90 |
| 30 min | 10 | 99 |
| Final pH | 2.4 | 2.4 |

Examples 13 & 14

The present invention is further described by the following non-limiting examples which compare the dissolution profiles for all the acids and unionized drugs exemplified, and their solubilities.

Example 13

This example demonstrates the dissolution rates of the formulations from the examples of acid and unionized drugs in 900 ml 0.0033 N HCl. without stirring (0 rpm) and with string (30 rpm). Table 30 summarises dissolution data for formulations of this present invention and two examples of commercial paracetamol tablets which are formulated for fast action. FIGS. 1 to 27 depict graphically the dissolution results.

It is clear from these results that all formulations according to the invention had a dissolution rate greater than 5% at 30 minutes. Further, the formulations according to the invention which contained a pharmaceutically acceptable acid in addition to the bicarbonate had a dissolution rate greater than 5% at 300 seconds.

TABLE 30

Dissolution profiles for all exemplified acidic and unionized* drugs in formulations according to the invention compared with two commercial paracetamol products formulated for fast action at 0 and 30 rpm stirring speed in 900 mL 0.0033 N HCl

| Drug | pH modulating agents Base | pH modulating agents Acid | % dissolved in 900 mL 0.0033 N HCl Time 300 sec Stirring speed rpm 0 | % dissolved in 900 mL 0.0033 N HCl Time 300 sec Stirring speed rpm 30 | % dissolved in 900 mL 0.0033 N HCl Time 15 minutes Stirring speed rpm 0 | % dissolved in 900 mL 0.0033 N HCl Time 15 minutes Stirring speed rpm 30 | % dissolved in 900 mL 0.0033 N HCl Time 30 minutes Stirring speed rpm 0 | % dissolved in 900 mL 0.0033 N HCl Time 30 minutes Stirring speed rpm 30 |
|---|---|---|---|---|---|---|---|---|
| | mg/tab | | 0 | 30 | 0 | 30 | 0 | 30 |
| Ibuprofen sodium/Ibuprofen (Ex 1-2) | 400 | 0 | 5 | 84 | 18 | 89 | 28 | 91 |
| Ibuprofen (Ex 2-2) | 400 | 0 | 32 | 74 | 48 | 82 | 65 | 87 |
| Diclofenac potassium (Ex 3-2) | 600 | 0 | 2 | 75 | 6 | 85 | 9 | 92 |
| Paracetamol * (Ex 4-3) | 200 | 75 | 68 | 88 | 79 | 95 | 83 | 104 |
| Paracetamol * (Ex 4-2) | 200 | 0 | 7 | 81 | 13 | 93 | 15 | 100 |
| Fast acting paracetamol* product (Aus) | 630 | 0 | 1 | 75 | 3 | 94 | 4 | 96 |
| Fast acting paracetamol* product (USA) | 0 | 0 | 1 | 20 | 3 | 46 | 10 | 61 |
| Naproxen (Ex 5-1) | 400 | 0 | 34 | 90 | 60 | 100 | 66 | 102 |
| Naproxen sodium (Ex 6-1) | 500 | 76 | 89 | 86 | 94 | 93 | 96 | 102 |
| Naproxen sodium (Ex 6-2) | 500 | 0 | 2 | 52 | 4 | 76 | 6 | 100 |
| Gemfibrozil (Ex 7-1) | 600 | 0 | 8 | 56 | 18 | 78 | 32 | 100 |
| Furosemide (Ex 8-1) | 400 | 0 | 39 | 87 | 51 | 88 | 60 | 100 |
| Temazepam * (Ex 9-1) | 20 | 0 | 51 | 74 | 70 | 88 | 80 | 101 |
| Montelukast sodium (Ex 10-2) | 600 | 76 | 65 | 80 | 84 | 82 | 87 | 94 |
| Prednisolone* (Ex 11-2) 5 mg | 20 | 14 | 75 | 83 | 89 | 90 | 97 | 100 |
| Prednisolone* (Ex 11-4) 25 mg | 40 | 28 | 69 | 86 | 86 | 90 | 95 | 100 |
| Dexamethasone* (Ex 12-2) | 40 | 28 | 57 | 79 | 90 | 86 | 99 | 100 |

Example 14

Table 31 summarises the solubility of a range of acid and unionized drugs formulated according to the invention as compared with celecoxib, a low solubility drug that does not meet the dissolution performance of the invention. This Example demonstrates that if the solubility of the drug can be increased by a change in pH, then complete dissolution can be achieved in 900 mL of the dissolution medium when formulated in accordance with the present invention.

The solubilities of the acidic compounds ibuprofen and gemfibrozil are increased at higher pH and so complete dissolution can be achieved. However the solubility of celecoxib remains low when formulated according to the present invention, and only around 1.6% of the dose will dissolve in 900 mL. Hence, based on solubility and dose considerations, celecoxib cannot meet the dissolution specification of this invention which requires more than 50% of the drug to dissolve in 300 seconds in 900 mL 0.0033 N hydrochloric acid in USP dissolution apparatus 2 at 30 rpm.

TABLE 31

Solubility Data for acid and unionized drugs which demonstrate enhanced dissolution when formulated according to the invention compared with celecoxib, a low solubility drug that does not meet the dissolution performance of the invention

| Drug and dose per tablet | >50% dissolution in 3 min at 30 rpm | Solubility in water (mg/mL) | Volume of water (mL) to dissolve dose | Type of compound | Effect of ↑ pH on solubility |
|---|---|---|---|---|---|
| Naproxen sodium 275 mg | ✓ | 222 | 1.2 | acid salt | ↑ |
| Diclofenac potassium 70 mg | ✓ | 10 | 7 | acid salt | ↑ |
| Prednisolone 5 mg | ✓ | 0.22 | 23 | unionized | ⇆ |
| Paracetamol 500 mg | ✓ | 14 | 36 | unionized | ⇆ |
| Dexamethasone 4 mg | ✓ | 0.09 | 44 | unionized | ⇆ |
| Temazepam 10 mg | ✓ | 0.12 | 83 | unionized | ⇆ |
| Prednisolone 25 mg | ✓ | 0.22 | 114 | unionized | ⇆ |

TABLE 31-continued

Solubility Data for acid and unionized drugs which demonstrate enhanced dissolution when formulated according to the invention compared with celecoxib, a low solubility drug that does not meet the dissolution performance of the invention

| Drug and dose per tablet | >50% dissolution in 3 min at 30 rpm | Solubility in water (mg/mL) | Volume of water (mL) to dissolve dose | Type of compound | Effect of ↑ pH on solubility |
|---|---|---|---|---|---|
| Furosemide 40 mg | ✓ | 0.095 | 421 | acid | ↑ |
| Ibuprofen 200 mg | ✓ | 0.04 | 5000 | acid | ↑ |
| Gemfibrozil 600 mg | ✓ | 0.029 | 20,690 | acid | ↑ |
| Celecoxib 200 mg | x | 0.00346 | 58,803 | unionized | ⇆ |

Examples 15 to 31

Overview of Examples

Examples 15 and 30 are salts of amphoteric drugs. Examples 16 to 22, 26, 27 and 29 are salts of basic drugs. Examples 23, 25 and 27 are bases. Example 24 is an amphoteric drug.

In Examples 26 to 30, the formulations designated '1' are always the comparative examples containing no carbonate. All other formulations of Examples 15 to 30 contain carbonate in accordance with the present invention.

Example 31 summarises the solubility data for the basic and amphoteric drugs exemplified.

Overview of Results

Table 32 summarises the dissolution results for Examples 15 to 30 at 30 rpm and 0 rpm.

Table 33 summarises the effect of using sodium bicarbonate alone or with an organic acid on the dissolution of selected drugs at 0 rpm.

Tables 34 to 77 set out the formulations of the examples and their corresponding dissolution rates.

Table 78 provides a summary of aqueous solubility data for all drugs exemplified in Examples 15 to 30 of the patent application.

FIGS. 28 to 59 depict graphically the dissolution results for Examples 15 to 30.

Conclusions and Further Comments Based on the Examples

It will be apparent that the use of pH modulating agents in accordance with the present invention substantially increases in vitro dissolution of the therapeutic agents exemplified.

Table 32 summarises the dissolution data for formulation examples that demonstrate the present invention in 900 mL 0.0033 N hydrochloric acid using USP apparatus 2 at 30 rpm and 0 rpm at 37° C.:

TABLE 32

Summary dissolution data for basic and amphoteric drugs in formulations according to the present invention, measured at 0 rpm and 30 rpm stirring speed in 900 mL 0.0033 N HCl

| Ex No | Drug | pH modulating agent (mg/tab) Base | pH modulating agent (mg/tab) Acid | 180 sec 0 | 180 sec 30 | 300 sec 0 | 300 sec 30 | 15 minutes 0 | 15 minutes 30 | 30 minutes 0 | 30 minutes 30 |
|---|---|---|---|---|---|---|---|---|---|---|---|
| 15 | Fexofenadine hydrochloride | 50 | 35 | 53 | 63 | 60 | 69 | 73 | 82 | 81 | 97 |
| 16 | Pseudoephedrine hydrochloride | 30 | 23 | 61 | 101 | 80 | 101 | 100 | 101 | 100 | 101 |
| 17 | Eletriptan hydrochloride | 40 | 28 | 88 | 94 | 95 | 96 | 98 | 97 | 100 | 99 |
| 18 | Rizatriptan benzoate | 50 | 38.4 | 94 | 96 | 102 | 96 | 100 | 96 | 100 | 97 |
| 19 | Metoclopramide hydrochloride | 20 | 15 | 26 | 94 | 69 | 95 | 86 | 97 | 91 | 100 |
| 20 | Loperamide hydrochloride | 20 | 16 | 70 | 82 | 72 | 84 | 87 | 89 | 95 | 100 |
| 21 | Codeine phosphate | 20 | 42 | 45 | 78 | 75 | 97 | 99 | 101 | 100 | 101 |
| 22 | Tramadol hydrochloride | 40 | 31 | 87 | 100 | 95 | 100 | 99 | 100 | 100 | 100 |
| 23 | Diazepam | 20 | 14 | 40 | 81 | 59 | 91 | 76 | 98 | 89 | 103 |
| 24 | Lorazepam | 40 | 28 | 77 | 77 | 85 | 88 | 95 | 96 | 99 | 100 |
| 25 | Alprazolam | 20 | 14 | 13 | 61 | 20 | 67 | 45 | 77 | 63 | 100 |
| 26 | Sildenafil citrate | 50 | — | 92 | 97 | 96 | 100 | 95 | 100 | 97 | 100 |
| 27 | Ondansetron hydrochloride | 20 | 18 | 50 | 88 | 65 | 96 | 79 | 100 | 85 | 100 |
| 28 | Zolmitriptan | 50 | 38.4 | 66 | 73 | 77 | 76 | 88 | 86 | 96 | 98 |
| 29 | Zolpidem tartrate | 50 | 38 | 77 | 96 | 91 | 96 | 94 | 97 | 96 | 98 |
| 30 | Cetirizine dihydrochloride | 6 | — | 67 | 84 | 78 | 87 | 90 | 92 | 96 | 96 |

It will be apparent from Table 32 that formulations according to the invention which contain a pharmaceutically acceptable acid in addition to a bicarbonate, demonstrate substantially increased in vitro dissolution of the therapeutic agents exemplified in the absence of external stirring. This highlights the role of intrinsic microstirring in enhancing dissolution, where the reaction between the pH modulating agents has a greater effect on dissolution than the reaction between the base and acid in the dissolution medium.

At 30 rpm, with the exception of fexofenadine hydrochloride and alprazolam, it is clear from these results that the formulations of these drugs containing pH modulating agents according to the invention, had a dissolution rate greater than 70% at 180 seconds. Fexofenadine hydrochloride and alprazolam did not meet this specification, achieving 63% and 61% dissolution respectively at 180 seconds at 30 rpm. However, it should be noted that no formulation optimisation was conducted, and it is expected that better performing examples could be formulated according to the present invention.

For some drugs such as sildenafil citrate and cetirizine hydrochloride, enhanced dissolution was achieved with formulations containing a bicarbonate alone. For others, the addition of an organic acid to the bicarbonate further enhanced the dissolution. In some cases the addition of an acid was necessary to achieve the dissolution performance described in this specification.

The impact of the composition of the pH modulating agent on dissolution is highlighted in the absence of external stirring, at 0 rpm. Results for a number of basic and amphoteric drugs are summarised in Table 33 where formulations contain bicarbonate alone or bicarbonate with an organic acid.

TABLE 33

Summary dissolution data for basic and amphoteric drugs in formulations according to the invention showing the effect of the composition of the pH modulating agent, measured at 0 rpm stirring speed in 900 mL 0.0033 N HCl

| Ex no | Drug and dose | pH modulating agent | % drug dissolved in 900 mL 0.0033 N HCl at 0 rpm | | |
|---|---|---|---|---|---|
| | | | 300 sec | 15 min | 30 min |
| 15 | Fexofenadine hydrochloride 180 mg | Bicarbonate | 49 | 54 | 60 |
| | | Bicarb + acid | 60 | 73 | 81 |
| 16 | Pseudoephedrine hydrochloride 60 mg | Bicarbonate | 45 | 69 | 102 |
| | | Bicarb + acid | 80 | 100 | 100 |
| 19 | Metoclopramide hydrochloride 10 mg | Bicarbonate | 5 | 28 | 46 |
| | | Bicarb + acid | 69 | 86 | 91 |
| 20 | Loperamide hydrochloride 2 mg | Bicarbonate | 27 | 43 | 101 |
| | | Bicarb + acid | 72 | 87 | 95 |
| 21 | Codeine phosphate 30 mg | Bicarbonate | 90 | 92 | 96 |
| | | Bicarb + acid | 75 | 99 | 100 |
| 23 | Diazepam 5 mg | Bicarbonate | 2 | 3 | 4 |
| | | Bicarb + acid | 59 | 76 | 89 |
| 24 | Lorazepam 2.5 mg | Bicarbonate | 6 | 6 | 11 |
| | | Bicarb + acid | 85 | 95 | 99 |
| 25 | Alprazolam 1 mg | Bicarbonate | 1 | 4 | 4 |
| | | Bicarb + acid | 20 | 45 | 63 |
| 26 | Sildenafil citrate 140 mg | Bicarbonate | 96 | 95 | 97 |
| 30 | Cetirizine hydrochloride 10 mg | Bicarbonate | 78 | 90 | 96 |

As seen in Table 33, in the absence of external stirring, at 0 rpm, the results achieved for formulations containing a base alone are significantly reduced compared to those for formulations containing an acid and a base. This results from the greater intrinsic microstirring resulting from the reaction between the base and organic acid relative to the reaction between the base and the acidic dissolution medium.

In the formulations that contained sodium bicarbonate alone without any additional acid, most drugs achieved more than 5% dissolution in 30 minutes at 0 rpm. While diazepam and alprazolam did not meet this specification at 4%, the addition of an organic acid significantly improves their dissolution. This results from the greater intrinsic microstirring resulting from the reaction between the base and organic acid relative to the reaction between the base and the acidic dissolution medium.

It should be noted that no formulation optimisation was conducted, and it is expected that better performing examples could be formulated according to the present invention.

Example 15

A Salt of an Amphoteric Compound

The formulations in this example were prepared by reformulation of commercial product.

TABLE 34

Fexofenadine Hydrochloride Formulations

| | Formulation | | |
|---|---|---|---|
| | 1 | 2 | Commercial product |
| Fexofenadine hydrochloride (mg) | 180 | 180 | 180 |
| Sodium bicarbonate (mg) | 50 | 50 | 0 |
| Fumaric acid (mg) | 0 | 35 | 0 |
| Microcrystalline cellulose (mg) | ✓ + 150 | ✓ + 150 | ✓ |
| Croscarmellose sodium (mg) | ✓ + 30 | ✓ + 30 | ✓ |
| Pregelatinised maize starch, magnesium stearate | ✓ | ✓ | ✓ |
| Total (mg) | 850 | 885 | 620 |
| pH modulating agent (%) | 5.9 | 9.6 | 0 |
| Hardness (Kp) | 14 | 14 | >33 |
| Disintegration time in 0.0033 N HCl (sec) | 60 | <40 | 180 |

Formulations 1 and 2 were compressed using 19 mm×9 mm oval shaped punches.

The commercial product was a 18 mm×8 mm coated oval shaped convex tablet.

TABLE 35

Fexofenadine Hydrochloride dissolution data in 900 mL 0.0033 N HCl at 30 rpm

| | % drug dissolved in 900 mL 0.0033 N HCl at 30 rpm | | |
|---|---|---|---|
| | Formulation | | |
| | 1 | 2 | Commercial product |
| 90 sec | 46 | 49 | 3 |
| 120 sec | 56 | 55 | 6 |
| 180 sec | 63 | 63 | 13 |
| 5 min | 69 | 69 | 26 |
| 15 min | 76 | 82 | 45 |
| Final pH | 2.4 | 2.4 | 2.3 |

TABLE 36

Fexofenadine Hydrochloride dissolution data in 900 mL 0.0033 N HCl at 0 rpm

% drug dissolved in 900 mL 0.0033 N HCl at 0 rpm Formulation

|         | 1   | 2   | Commercial product |
|---------|-----|-----|--------------------|
| 90 sec  | 30  | 41  | 0                  |
| 120 sec | 34  | 46  | 0                  |
| 180 sec | 40  | 53  | 0                  |
| 5 min   | 49  | 60  | 0                  |
| 15 min  | 54  | 73  | 1                  |
| 30 min  | 60  | 81  | 4                  |
| Final pH| 2.4 | 2.4 | 2.3                |

Example 16

A Salt of a Basic Compound

The formulations in this example were prepared by reformulation of commercial product.

TABLE 37

Pseudoephedrine Hydrochloride Formulations

|                                | Formulation |     |                    |
|--------------------------------|-------------|-----|--------------------|
|                                | 1           | 2   | Commercial product |
| Pseudoephedrine hydrochloride (mg) | 60      | 60  | 60                 |
| Sodium bicarbonate (mg)        | 30          | 30  | 0                  |
| Citric acid anhydrous (mg)     | 0           | 23  | 0                  |
| Microcrystalline cellulose (mg)| 80          | 120 | 0                  |
| Crospovidone (mg)              | 15          | 20  | 0                  |
| Lactose                        | ✓           | ✓   | ✓                  |
| Magnesium stearate (mg)        | 3           | 3   | 0                  |
| Total (mg)                     | 365         | 433 | 237                |
| pH modulating agent (%)        | 8.2         | 12.2| 0                  |
| Hardness (Kp)                  | 6           | 3   | 1.5                |
| Disintegration time in 0.0033 N HCl (Sec) | 120 | 40 | 22             |

Tablets 1 and 2 were compressed using 15 mm×5 mm oval shallow concave punches with a break bar.

The commercial tablets were uncoated 8.5 mm diameter round flat bevelled edge with a break-bar.

TABLE 38

Pseudoephedrine Hydrochloride dissolution data in 900 mL 0.0033 N HCl at 30 rpm

% drug dissolved in 900 mL 0.0033 N HCl at 30 rpm Formulation

|         | 1   | 2   | Commercial product |
|---------|-----|-----|--------------------|
| 90 sec  | 14  | 87  | 11                 |
| 120 sec | 21  | 100 | 16                 |
| 180 sec | 31  | 101 | 23                 |
| 5 min   | 45  | 101 | 35                 |
| 15 min  | 69  | 102 | 62                 |
| Final pH| 2.3 | 2.3 | 2.3                |

TABLE 39

Pseudoephedrine Hydrochloride dissolution data in 900 mL 0.0033 N HCl at 0 rpm

% drug dissolved in 900 mL 0.0033 N HCl at 0 rpm Formulation

|         | 1   | 2   |
|---------|-----|-----|
| 90 sec  | 0   | 32  |
| 120 sec | 0   | 34  |
| 180 sec | 2   | 61  |
| 5 min   | 4   | 80  |
| 15 min  | 17  | 100 |
| 30 min  | 33  | 101 |
| Final pH| 2.3 | 2.3 |

Example 17

A Salt of a Basic Compound

The formulations in this example were prepared by reformulation of commercial product.

TABLE 40

Eletriptan Hydrobromide Formulations

|                                | Formulation |        |                    |
|--------------------------------|-------------|--------|--------------------|
|                                | 1           | 2      | Commercial product |
| Eletriptan Hydrobromide (mg)   | 48.5        | 48.5   | 48.5               |
| Sodium bicarbonate (mg)        | 20          | 40     | 0                  |
| Fumaric acid (mg)              | 0           | 28     | 0                  |
| Microcrystalline cellulose (mg)| ✓ + 70     | ✓ + 70 | ✓                  |
| Croscarmellose sodium (mg)     | ✓ + 10     | ✓ + 10 | ✓                  |
| Lactose, magnesium stearate, coating and colorings | ✓ | ✓ | ✓ |
| Total (mg)                     | 300         | 348    | 204                |
| pH modulating agent (%)        | 6.7         | 19.5   | 0                  |
| Hardness (Kp)                  | 6           | 4      | —                  |
| Disintegration time in 0.0033 N HCl (Sec) | 28 | 50 | —              |

Formulations 1 and 2 were compressed using 10 mm round shallow concave punches.

The commercial product was coated 8.5 mm diameter round biconvex tablets.

TABLE 41

Eletriptan Hydrobromide dissolution data in 900 mL 0.0033 N HCl at 30 rpm

% drug dissolved in 900 mL 0.0033 N HCl at 30 rpm Formulation

|         | 1   | 2   | Commercial product |
|---------|-----|-----|--------------------|
| 90 sec  | 27  | 88  | 2                  |
| 120 sec | 30  | 92  | 4                  |
| 180 sec | 34  | 94  | 9                  |
| 5 min   | 37  | 96  | 23                 |
| 15 min  | 48  | 97  | 42                 |
| Final pH| 1.7 | 1.7 | 1.8                |

TABLE 42

Eletriptan Hydrobromide dissolution data in 900 mL 0.0033 N HCl at 0 rpm

| | % drug dissolved in 900 mL 0.0033 N HCl at 0 rpm Formulation | |
|---|---|---|
| | 2 | Commercial product |
| 90 sec | 63 | 0 |
| 120 sec | 75 | 0 |
| 180 sec | 88 | 0 |
| 5 min | 95 | 0 |
| 15 min | 98 | 2 |
| 30 min | 100 | 8 |
| Final pH | 2.3 | 2.3 |

Example 18

A Salt of a Basic Compound

TABLE 43

Rizatriptan Benzoate Formulations

| | Formulation | |
|---|---|---|
| | 1 | 2 |
| Rizatriptan Benzoate (mg) | 14.53 | 14.53 |
| Sodium bicarbonate (mg) | 10 | 40 |
| Citric acid anhydrous (mg) | 0 | 30.7 |
| Microcrystalline cellulose (mg) | 111.97 | 51.27 |
| Crospovidone (mg) | 12 | 12 |
| Magnesium stearate (mg) | 1.5 | 1.5 |
| Total (mg) | 150 | 150 |
| pH modulating agent (%) | 6.7 | 6.7 |
| Hardness (Kp) | 5 | 4 |
| Disintegration time in 0.0033 N HCl (Sec) | 6 | 32 |

Formulations 1 and 2 were compressed using 8 mm round shallow concave punches.

The commercial product from the USA was an uncoated 12×5 mm oval capsule shaped tablet.

TABLE 44

Rizatriptan Benzoate dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 90 sec | 41 | 81 | 28 |
| 120 sec | 45 | 93 | 37 |
| 180 sec | 51 | 96 | 48 |
| 5 min | 58 | 96 | 61 |
| 15 min | 76 | 96 | 77 |
| Final pH | 2.3 | 2.3 | 2.4 |

TABLE 45

Rizatriptan Benzoate dissolution data in 900 mL 0.0033 N HCl at 0 rpm

| | % drug dissolved in 900 mL 0.0033 N HCl at 0 rpm Formulation 2 |
|---|---|
| 90 sec | 80 |
| 120 sec | 91 |
| 180 sec | 94 |
| 5 min | 102 |
| 15 min | 100 |
| 30 min | 100 |
| Final pH | 2.3 |

Example 19

A Salt of a Basic Compound

The formulations in this example were prepared by reformulation of commercial product.

TABLE 46

Metoclopramide Hydrochloride Formulations

| | Formulation | | |
|---|---|---|---|
| | 1 | 2 | Commercial product |
| Metoclopramide Hydrochloride (mg) | 10 | 10 | 10 |
| Sodium bicarbonate (mg) | 20 | 20 | 0 |
| Fumaric acid (mg) | 0 | 15 | 0 |
| Microcrystalline cellulose (mg) | √ + 80 | √ + 80 | √ |
| Crospovidone (mg) | 15 | 15 | 0 |
| Lactose anhydrous, colloidal anhydrous silica | √ | √ | √ |
| Pregelatinised maize starch | √ + 3 | √ + 3 | √ |
| Magnesium stearate (mg) | √ + 3 | √ + 3 | √ |
| Total (mg) | 244 | 259 | 126 |
| pH modulating agent (%) | 8.2 | 13.5 | 0 |
| Hardness (Kp) | 8 | 8 | — |
| Disintegration time in 0.0033 N HCl (Sec) | 146 | 146 | — |

Formulations 1 and 2 were compressed using 8 mm round shallow concave punches.

The commercial tablets from the USA were uncoated 7 mm diameter round convex.

TABLE 47

Metoclopramide Hydrochloride dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 90 sec | 6 | 49 | 6 |
| 120 sec | 12 | 79 | 8 |
| 180 sec | 22 | 94 | 13 |
| 5 min | 41 | 95 | 24 |
| 15 min | 72 | 97 | 66 |
| Final pH | 2.0 | 2.0 | 2.1 |

TABLE 48

Metoclopramide Hydrochloride dissolution
data in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 1 | 5 |
| 120 sec | 1 | 9 |
| 180 sec | 2 | 26 |
| 5 min | 5 | 69 |
| 15 min | 28 | 86 |
| 30 min | 46 | 91 |
| Final pH | 2.1 | 2.1 |

Example 20

A Salt of a Basic Compound

The formulations in this example were prepared by reformulation of commercial product.

TABLE 49

Loperamide Hydrochloride Formulations

| | Formulation | | |
|---|---|---|---|
| | 1 | 2 | Commercial product |
| Loperamide Hydrochloride (mg) | 2 | 2 | 2 |
| Sodium bicarbonate (mg) | 20 | 20 | 0 |
| Malic acid (mg) | 0 | 16 | 0 |
| Microcrystalline cellulose (mg) | √ + 80 | √ + 80 | √ |
| Crospovidone (mg) | 15 | 15 | 0 |
| Calcium phosphate, colloidal silica anhydrous, colour | √ | √ | √ |
| Magnesium stearate (mg) | √ + 3 | √ + 3 | √ |
| Total (mg) | 268 | 284 | 150 |
| pH modulating agent (%) | 7.5 | 7.5 | 0 |
| Hardness (Kp) | 5.5 | 5 | 5.5 |
| Disintegration time in 0.0033 N HCl (Sec) | 7 | 11 | 57 |

Formulations 1 and 2 were compressed using 8 mm round shallow concave punches.

The commercial product was an uncoated 9 mm×4.5 mm capsule shaped tablet.

TABLE 50

Loperamide Hydrochloride dissolution
data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 90 sec | 9 | 76 | 10 |
| 120 sec | 12 | 80 | 15 |
| 180 sec | 18 | 82 | 31 |
| 5 min | 27 | 84 | 48 |
| 15 min | 43 | 89 | 79 |
| Final pH | 2.5 | 2.5 | 2.3 |

TABLE 51

Loperamide Hydrochloride Dissolution
in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 3 | 28 |
| 120 sec | 3 | 50 |
| 180 sec | 7 | 70 |
| 5 min | 12 | 72 |
| 15 min | 20 | 87 |
| 30 min | 26 | 95 |
| Final pH | 2.5 | 2.5 |

Example 21

A Salt of a Basic Compound

The formulations in this example were prepared by reformulation of commercial product.

TABLE 52

Codeine Phosphate Formulations

| | Formulation | | |
|---|---|---|---|
| | 1 | 2 | Commercial product |
| Codeine Phosphate (mg) | 30 | 30 | 30 |
| Sodium bicarbonate (mg) | 20 | 20 | 0 |
| Ascorbic acid (mg) | 0 | 42 | 0 |
| Microcrystalline cellulose (mg) | 80 | 80 | 0 |
| Crospovidone (mg) | 10 | 10 | 0 |
| Gelatin, maize starch, propyl hydroxybenzoate, lactose, wheat starch | √ | √ | √ |
| Magnesium stearate (mg) | √ + 2 | √ + 2 | √ |
| Total (mg) | 192 | 234 | 80 |
| pH modulating agent (%) | 10.4 | 26.5 | 0 |
| Hardness (Kp) | 4 | 5 | 4.2 |
| Disintegration time in 0.0033 N HCl (Sec) | 76 | 48 | 310 |

Formulations 1 and 2 were compressed using 8 mm round shallow concave punches.

The commercial tablets were uncoated 5.6 mm round shallow convex.

TABLE 53

Codeine Phosphate dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 90 sec | 30 | 35 | 12 |
| 120 sec | 46 | 51 | 21 |
| 180 sec | 72 | 78 | 34 |
| 5 min | 90 | 97 | 55 |
| 15 min | 92 | 101 | 99 |
| Final pH | 2.4 | 2.4 | 2.3 |

TABLE 54

Codeine Phosphate dissolution data in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 22 | 54 |
| 120 sec | 25 | 52 |
| 180 sec | 28 | 45 |
| 5 min | 42 | 75 |
| 15 min | 78 | 99 |
| 30 min | 92 | 100 |
| Final pH | 2.4 | 2.4 |

Example 22

A Salt of a Basic Compound

TABLE 55

Tramadol Hydrochloride Formulations

| | Formulation 2 |
|---|---|
| Tramadol Hydrochloride (mg) | 37.5 |
| Sodium bicarbonate (mg) | 40 |
| Citric acid anhydrous (mg) | 31 |
| Microcrystalline cellulose (mg) | 79.5 |
| Crospovidone (mg) | 10 |
| Magnesium stearate (mg) | 2 |
| Total (mg) | 200 |
| pH modulating agent (%) | 35.5 |
| Hardness (Kp) | 3.5 |
| Disintegration time in 0.0033 N HCl (Sec) | 10 |

Formulations were compressed using 7 mm round shallow concave punches.

The commercial tablets were coated 13×5 mm capsule shaped.

TABLE 56

Tramadol Hydrochloride dissolution data in 900 mL 0.0033 N HCl at 30 rpm

| | % drug dissolved in 900 mL 0.0033 N HCl at 30 rpm Formulation | |
|---|---|---|
| | 2 | Commercial product |
| 90 sec | 100 | 2 |
| 120 sec | 100 | 3 |
| 180 sec | 100 | 6 |
| 5 min | 100 | 15 |
| 15 min | 100 | 56 |
| Final pH | 2.2 | 2.3 |

TABLE 57

Tramadol Hydrochloride dissolution data in 900 mL 0.0033 N HCl at 0 rpm

| | % drug dissolved in 900 mL 0.0033 N HCl at 0 rpm Formulation | |
|---|---|---|
| | 2 | Commercial product |
| 90 sec | 98 | 0 |
| 120 sec | 91 | 0 |

TABLE 57-continued

Tramadol Hydrochloride dissolution data in 900 mL 0.0033 N HCl at 0 rpm

| | % drug dissolved in 900 mL 0.0033 N HCl at 0 rpm Formulation | |
|---|---|---|
| | 2 | Commercial product |
| 180 sec | 87 | 0 |
| 5 min | 95 | 0 |
| 15 min | 99 | 2 |
| 30 min | 100 | 6 |
| Final pH | 2.3 | 2.3 |

Example 23

A Basic Compound

The formulations in this example were prepared by reformulation of commercial product.

TABLE 58

Diazepam Formulations

| | Formulation | | |
|---|---|---|---|
| | 1 | 2 | Commercial Product |
| Diazepam (mg) | 5 | 5 | 5 |
| Sodium bicarbonate (mg) | 20 | 20 | 0 |
| Fumaric acid (mg) | 0 | 14 | 0 |
| Microcrystalline cellulose (mg) | 80 | 80 | 0 |
| Crospovidone (mg) | 15 | 15 | 0 |
| Maize starch, lactose, colour QY CI147005 (E104) | ✓ | ✓ | ✓ |
| Magnesium stearate (mg) | ✓ + 3 | ✓ + 3 | ✓ |
| Total (mg) | 288 | 302 | 170 |
| pH modulating agent (%) | 6.94 | 11.2 | 0 |
| Hardness (Kp) | 10 | 8 | — |
| Disintegration time in 0.0033 N HCl (Sec) | 79 | 37 | — |

Formulations 1 and 2 were compressed using 8 mm round shallow concave punches.

The commercial tablets were uncoated 8 mm round flat bevelled edge with break 10 bar.

TABLE 59

Diazepam dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial Product |
| 90 sec | 10 | 60 | 7 |
| 120 sec | 18 | 70 | 11 |
| 180 sec | 25 | 81 | 18 |
| 240 sec | 28 | 87 | 24 |
| 5 min | 30 | 91 | 29 |
| 15 min | 44 | 98 | 53 |
| Final pH | 2.3 | 2.3 | 2.3 |

TABLE 60

Diazepam dissolution data in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 1 | 19 |
| 120 sec | 0 | 31 |
| 180 sec | 1 | 40 |
| 5 min | 2 | 59 |
| 15 min | 3 | 76 |
| 30 min | 4 | 89 |
| Final pH | 2.3 | 2.3 |

Example 24

An Amphoteric Compound

The formulations in this example were prepared by reformulation of commercial product.

TABLE 61

Lorazepam Formulations

| | Formulation | | Commercial Product |
|---|---|---|---|
| | 1 | 2 | |
| Lorazepam (mg) | 2.5 | 2.5 | 2.5 |
| Sodium bicarbonate (mg) | 40 | 40 | 0 |
| Fumaric acid (mg) | 0 | 28 | 0 |
| Microcrystalline cellulose (mg) | 100 | 100 | 0 |
| Crospovidone (mg) | 25 | 25 | 0 |
| Lactose & other excipients | ✓ | ✓ | ✓ |
| Magnesium stearate (mg) | 2 | 2 | 0 |
| Total (mg) | 365 | 393 | 198 |
| pH modulating agent (%) | 11 | 17.3 | 0 |
| Hardness (Kp) | 10 | 9 | — |
| Disintegration time in 0.0033 N HCl (Sec) | 10 | 10 | 6 |

Formulations 1 and 2 were compressed using 15 mm×5 mm oval shallow concave punches with break bar.

The commercial tablets were uncoated 7 mm round convex with an enlarged break bar.

TABLE 62

Lorazepam dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial Product |
| 90 sec | 19 | 54 | 7 |
| 120 sec | 28 | 63 | 13 |
| 180 sec | 36 | 77 | 18 |
| 240 sec | 42 | 84 | 24 |
| 5 min | 46 | 88 | 26 |
| 30 min | 100 | 100 | 99 |
| Final pH | 2.2 | 2.2 | 2.2 |

TABLE 63

Lorazepam dissolution data in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 0 | 50 |
| 120 sec | 1 | 70 |
| 180 sec | 2 | 77 |
| 5 min | 6 | 85 |
| 15 min | 6 | 95 |
| 30 min | 11 | 99 |
| Final pH | 2.2 | 2.2 |

Example 25

A Basic Compound

The formulations in this example were prepared by reformulation of commercial product.

TABLE 64

Alprazolam Formulations

| | Formulation | | Commercial Product |
|---|---|---|---|
| | 1 | 2 | |
| Alprazolam (mg) | 1 | 1 | 1 |
| Sodium bicarbonate (mg) | 20 | 20 | 0 |
| Fumaric acid (mg) | 0 | 14 | 0 |
| Microcrystalline cellulose (mg) | ✓ + 80 | ✓ + 80 | ✓ |
| Crospovidone (mg) | 15 | 15 | 0 |
| Lactose, maize starch, sodium benzoate, docusate sodium, povidone, colloidal anhydrous silica, sodium starch glycolate, indigo carmine CI 73015 | ✓ | ✓ | ✓ |
| Magnesium stearate (mg) | ✓ + 3 | ✓ + 3 | ✓ |
| Total (mg) | 248 | 262 | 130 |
| pH modulating agent (%) | 8.1 | 13.0 | 0 |
| Hardness (Kp) | 9 | 8 | — |
| Disintegration time in 0.0033 N HCl (Sec) | 74 | 67 | 180 |

Formulations 1 and 2 were compressed using 8 mm round shallow concave punches.

The commercial product was a flat 9 mm×5 mm oval uncoated tablet with a break-bar.

TABLE 65

Alprazolam dissolution data in 900 mL 0.0033 N HCl at 30 rpm

| | % drug dissolved in 900 mL 0.0033 N HCl at 30 rpm Formulation | | |
|---|---|---|---|
| | 1 | 2 | Commercial product |
| 90 sec | 22 | 48 | 4 |
| 120 sec | 30 | 56 | 15 |
| 180 sec | 39 | 61 | 29 |
| 5 min | 50 | 67 | 46 |
| Final pH | 2.2 | 2.3 | 2.2 |

TABLE 66

Alprazolam dissolution data in 900 mL 0.0033 N HCl at 0 rpm

| | % drug dissolved in 900 mL 0.0033 N HCl at 0 rpm Formulation | |
|---|---|---|
| | 1 | 2 |
| 90 sec | 0 | 7 |
| 120 sec | 0 | 10 |
| 180 sec | 1 | 13 |
| 5 min | 1 | 20 |
| 15 min | 4 | 45 |
| 30 min | 4 | 63 |
| Final pH | 2.2 | 2.2 |

Example 26

A Salt of a Basic Compound

TABLE 67

Sildenafil Citrate Formulations

| | Formulation | | | |
|---|---|---|---|---|
| | 1 | 2 | 3 | 4 |
| Sodium bicarbonate (mg) | 0 | 50 | 0 | 50 |
| Potassium bicarbonate (mg) | 0 | 0 | 50 | 0 |
| Microcrystalline cellulose (mg) | 370 | 320 | 280 | 255 |
| Croscarmellose sodium (mg) | 25 | 25 | 25 | 35 |
| Sildenafil citrate(mg) | 100 | 100 | 140 | 140 |
| Magnesium stearate (mg) | 5 | 5 | 5 | 5 |
| Povidone K-30 (mg) | 0 | 0 | 0 | 4.4 |
| Carbonate (%) | 0 | 10 | 10 | 10.2 |
| Total (mg) | 500 | 500 | 500 | 489.4 |

Formulation 4 was prepared by the following wet granulation method using the ingredients as itemised in Table 68:

Method

Blend Items 1, 2 and 3. Prepare a 1.3% w/w solution of 4 in deionised water and spray onto the blended powders in a granulator or mixer to produce a granule suitable for compression. Dry the granules at 50° C. to a moisture content ~3% and screen through a 850 micron sieve. Screen Items 5-7 through a 250 micron sieve and blend with the dried granules. Screen Item 8 through a 250 micron sieve and blend with the granule mix. Compress to the maximum hardness such that the disintegration time is less than 30 seconds and friability is less than 0.1%.

TABLE 68

Formulation 4 for a Sildenafil Citrate Granulation

| Item No | Ingredient | mg/tablet |
|---|---|---|
| 1 | Sildenafil citrate | 140 |
| 2 | Microcrystalline cellulose | 205 |
| 3 | Croscarmellose sodium | 20 |
| 4 | Povidone K-30 (PVP) | 4.4 |
| 5 | Sodium bicarbonate | 50 |
| 6 | Croscarmellose sodium | 15 |
| 7 | Microcrystalline cellulose | 50 |
| 8 | Magnesium stearate | 5 |

TABLE 69

Sildenafil Citrate dissolution data in 900 mL 0.0033 N HCl at 30 rpm

| | % drug dissolved in 900 mL 0.0033 N HCl at 30 rpm | | |
|---|---|---|---|
| Formulation | 90 sec | 120 sec | 180 sec |
| 1 | 13.2 | 15.2 | 18.2 |
| 2 | >99 | >99 | >99 |
| 3 | 89.5 | 93.5 | 97.3 |
| 4 | 94.4 | 97.5 | >99 |

Example 27

A Salt of a Basic Compound

TABLE 70

Ondansetron Hydrochloride Formulations

| | Formulation | |
|---|---|---|
| | 1 | 2 |
| Sodium bicarbonate (mg) | 0 | 20 |
| Microcrystalline cellulose (mg) | 180 | 140 |
| Crospovidone (mg) | 10 | 10 |
| Glycine (mg) | 0 | 18 |
| Ondansetron hydrochloride (mg) | 8 | 10 |
| Magnesium stearate (mg) | 2 | 2 |
| Carbonate (%) | 0 | 10 |
| Total (mg) | 200 | 200 |

TABLE 71

Ondansetron Hydrochloride dissolution data in 900 mL 0.0033 N HCl at 30 rpm

| | % drug dissolved in 900 mL 0.0033 N HCl at 30 rpm | | |
|---|---|---|---|
| Formulation | 90 sec | 120 sec | 180 sec |
| 1 | 36.5 | 44.7 | 55.3 |
| 2 | 73.0 | 80.6 | 87.9 |

Example 28

A Basic Compound

TABLE 72

Zolmitriptan Formulations

| | Formulation | |
|---|---|---|
| | 1 | 2 |
| Sodium bicarbonate (mg) | 0 | 50 |
| Microcrystal cellulose (mg) | 110.3 | 97.1 |
| Sodium starch glycolate (mg) | 6 | 10 |
| Citric acid anhydrous (mg) | 0 | 38.4 |
| Zolmitriptan (mg) | 2.5 | 2.5 |
| Magnesium stearate (mg) | 1.2 | 2 |
| Carbonate (%) | 0 | 25 |
| Total (mg) | 120 | 200 |

TABLE 73

Zolmitriptan dissolution data in 900 mL 0.0033 N HCl at 30 rpm

| | % drug dissolved in 900 mL 0.0033 N HCl at 30 rpm | | |
|---|---|---|---|
| Formulation | 90 sec | 120 sec | 180 sec |
| 1 | 35.5 | 42.3 | 51.7 |
| 2 | 95.1 | 97.3 | 98.9 |

Example 29

A Salt of a Basic Compound

TABLE 74

Zolpidem Tartrate Formulations

| | Formulation 1 | Formulation 2 | Formulation 3 |
|---|---|---|---|
| Zolpidem tartrate (mg) | 10 | 10 | 10 |
| Sodium bicarbonate (mg) | 0 | 50 | 50 |
| Microcrystalline cellulose (mg) | 178 | 83 | 89.6 |
| Sodium starch glycolate (mg) | 10 | 10 | 10 |
| Tartaric acid 99% (mg) | 0 | 45 | 0 |
| Citric acid anhydrous (mg) | 0 | 0 | 38.4 |
| Magnesium stearate (mg) | 2 | 2 | 2 |
| Carbonate (%) | 0 | 25 | 25 |
| Total (mg) | 200 | 200 | 200 |

TABLE 75

Zolpidem Tartrate dissolution data in 900 mL 0.0033 N HCl at 30 rpm

| | % drug dissolved in 900 mL 0.0033 N HCl at 30 rpm | | |
|---|---|---|---|
| Formulation | 90 sec | 120 sec | 108 sec |
| 1 | 49.4 | 55.8 | 62.3 |
| 2 | 89.4 | 91.8 | 92.6 |
| 3 | 94.4 | 35.9 | 96.1 |

Example 30

A Salt of an Amphoteric Compound

TABLE 76

Cetirizine Dihydrochloride Formulations

| | Formulations 1 | 2 | 3 |
|---|---|---|---|
| Cetirizine dihydrochloride (mg) | 10 | 10 | 10 |
| Sodium bicarbonate (mg) | 0 | 20 | 6 |
| Microcrystalline cellulose (mg) | 178 | 158 | 172 |
| Crospovidone (mg) | 10 | 10 | 10 |
| Magnesium stearate (mg) | 2 | 2 | 2 |
| Carbonate (%) | 0 | 10 | 3 |
| Total (mg) | 200 | 200 | 200 |

TABLE 77

Cetirizine Dihydrochloride dissolution data in 900 mL 0.0033 N HCl at 30 rpm

| | % drug dissolved in 900 mL 0.0033 N HCl at 30 rpm | | |
|---|---|---|---|
| Formulation | 90 sec | 120 sec | 180 sec |
| 1 | 27.7 | 36.8 | 47.8 |
| 2 | 73.9 | 79 | 84.1 |
| 3 | 75.5 | 79.6 | 82.9 |

Example 31

TABLE 78

Solubility Data for basic and amphoteric drugs and salts thereof which demonstrate enhanced dissolution when formulated according to the invention

| Ex. no. | Drug | Dose (mg) | Solubility in water (mg/mL) | Volume (mL) of water to dissolve dose | Type of active |
|---|---|---|---|---|---|
| 15 | Fexofenadine hydrochloride | 60 | 0.8 | 75 | Base salt |
| 16 | Pseudoephedrine hydrochloride | 60 | 2000 | 0.03 | Base salt |
| 17 | Eletriptan hydrobromide | 48 | 4 | 4 | Base salt |
| 18 | Rizatriptan benzoate | 14 | 42* | 0.3 | Base salt |
| 19 | Metoclopramide hydrochloride | 10 | 0.2* | 50 | Base salt |
| 20 | Loperamide hydrochloride | 2 | 0.08 | 2 | Base salt |
| 21 | Codeine phosphate | 30 | 435 | 0.07 | Base salt |
| 22 | Tramadol hydrochloride | 37.5 | 30 | 1.3 | Base salt |
| 23 | Diazepam | 5 | 0.04 | 125 | Base |
| 24 | Lorazepam | 2.5 | 0.08 | 31 | Amphoteric |
| 25 | Alprazolam | 1 | 0.07 | 14 | Base |
| 26 | Sildenafil citrate | 140 | 3.5 | 40 | Base salt |
| 27 | Ondansetron hydrochloride | 10 | 2.42 | 4 | Base salt |
| 28 | Zolmitriptan | 2.5 | 1.3 | 2 | Base |
| 29 | Zolpidem tartrate | 10 | 23 | 0.4 | Base salt |
| 30 | Cetirizine dihydrochloride | 10 | 0.1* | 100 | Amphoteric salt |

*solubility of the base not salt

Examples 32 and 33

The present invention is further described by the following additional non-limiting examples which relate to the unionized drug paracetamol, and a combination product that contains this unionized drug with the salt of a basic drug.

Overview of Examples

Example 32 covers paracetamol tablet formulations manufactured by a granulation process containing either sodium bicarbonate alone as the only pH modulating agent, or a combination of sodium bicarbonate and fumaric acid. These are compared with two commercial fast dissolving paracetamol products, Product X from the USA, and Product Y from Australia which contains 630 mg sodium bicarbonate as a pH modulating agent.

Example 33 covers tablet formulations manufactured by a granulation process containing paracetamol with the hydrochloride salt of a base analgesic drug, tramadol hydrochloride. One formulation contains sodium bicarbonate alone as the pH modulating agent, and the other a combination of sodium bicarbonate and fumaric acid. These are compared with a commercial product sourced from the USA containing the same doses of paracetamol and tramadol hydrochloride.

All formulations are prepared by wet granulation and demonstrate fast in vitro dissolution of both active ingredients under the test conditions described.

All examples contain dissolution profiles for:
- one formulation according to the invention with bicarbonate alone designated 1
- a second formulation according to the invention containing sodium bicarbonate with fumaric acid as an example of an organic acid designated 2
- a commercial product which contains no pH modulating agents as well as any fast dissolving commercial products containing pH modulating agents For Example 32, drug concentrations were measured continuously by UV absorbents.

For Example 33, concentrations of both drugs were measured by HLPC on samples drawn or taken at 1, 2, 3, 5, 10, 15, 20 and 30 minutes where the stirring speed was increased after 20 minutes from 30 rpm to 250 rpm.

Tables 79-86 set out the formulations and their corresponding dissolution data. FIGS. 60-63 depict graphically the dissolution results.

Overview of Results

Tables 79 and 80 summarise the percentages of the total dose of the drug dissolved for the two examples under different dissolution conditions, namely 900 mL 0.0033 N hydrochloric acid at 30 rpm and at 0 rpm respectively. These include dissolution data for commercially available products.

Table 81 details the formulations for the two paracetamol formulations, 1 and 2 from Example 32.

Tables 82 and 83 summarise the paracetamol dissolution data for the two formulations compared with the two commercial products, X and Y under the different dissolution conditions, namely 900 mL 0.0033 N hydrochloric acid at 30 rpm and at 0 rpm respectively.

Table 84 details the formulations for the two combination paracetamol with tramadol hydrochloride formulations from Example 33.

Table 85 and 86 summarises the dissolution data for paracetamol and tramadol hydrochloride from the combination formulations of Example 33 compared with the commercial product in 900 mL 0.0033 N hydrochloric acid at 30 rpm and at 0 rpm respectively.

FIGS. 60 and 61 illustrate the paracetamol dissolution profiles for the two paracetamol formulations of Example 32 compared with Products X and Y under different dissolution conditions, namely 900 mL 0.0033 N hydrochloric acid at 30 rpm and at 0 rpm respectively.

FIGS. 62 and 63 illustrate the dissolution profiles for paracetamol and tramadol hydrochloride from the combination formulations of Example 33 compared with the commercial product in 900 mL 0.0033 N hydrochloric acid at 30 rpm and at 0 rpm respectively.

Conclusions and Further Comments Based on the Examples

It will be apparent that the use of pH modulating agents in accordance with the present invention substantially increases the in vitro dissolution of the active ingredients from formulations containing paracetamol alone and in combination with other drugs such tramadol hydrochloride.

However, the results highlight the need to optimise formulations, particularly for combinations of drugs with respect to the levels and composition of the pH modulating agent to meet the specified dissolution performance. The addition of an organic acid is effective in enhancing dissolution allowing the use of lower levels of bicarbonate.

When paracetamol is used in combination with a base such as tramadol hydrochloride, it is found that the fastest in vitro dissolution of both drugs is achieved by using a bicarbonate with an organic acid compared with a bicarbonate alone. This combination of pH modulating agents provides intrinsic microstirring that will enhance the rate of dissolution of both drugs to a greater extent than the use of a base alone. Formulation 33-2 which contains an a pH modulating comprising an acid and a base at 19% w/w has a greater effect enhancing dissolution compared with 33-1 which contains 28% w/w of bicarbonate alone.

Table 79 summarises the dissolution data for formulation examples containing paracetamol alone (Example 32), and paracetamol with tramadol hydrochloride (Example 33) that demonstrate the present invention in 900 mL 0.0033 N hydrochloric acid using USP apparatus 2 at 30 rpm and 37° C.

TABLE 79

Dissolution data for paracetamol and tramadol hydrochloride in formulations according to the invention at 30 rpm in 900 mL 0.0033 N HCl

| Drug | Example | % dissolved in 900 mL 0.0033 N HCl at 30 rpm | | |
|---|---|---|---|---|
| | | 120 sec | 180 sec | 300 sec |
| Paracetamol | 32-1 (bicarbonate alone) | 49 | 60 | 69 |
| | 32-2 (bicarbonate + acid) | 71 | 73 | 78 |
| | Product X | 7 | 16 | 30 |
| | Product Y (bicarbonate) | 3 | 10 | 25 |
| Paracetamol from combination product | 33-1 (bicarbonate alone) | 9 | 15 | 25 |
| | 33-2 (bicarbonate + acid) | 89 | 90 | 91 |
| | Commercial Product | 1 | 4 | 12 |
| Tramadol hydrochloride from combination | 33-1 (bicarbonate alone) | 17 | 32 | 55 |
| | 33-2 | 101 | 102 | 102 |

TABLE 79-continued

Dissolution data for paracetamol and tramadol hydrochloride in formulations according to the invention at 30 rpm in 900 mL 0.0033 N HCl

| Drug | Example | % dissolved in 900 mL 0.0033 N HCl at 30 rpm | | |
|---|---|---|---|---|
| | | 120 sec | 180 sec | 300 sec |
| product | (bicarbonate + acid) Commercial Product | 3 | 6 | 10 |

These results show the enhanced dissolution of both paracetamol and tramadol hydrochloride from combination products when the pH modulating agent comprises a bicarbonate and an acid. Only when the pH modulating agent comprises an acid and a bicarbonate does the dissolution achieve greater than 70% in 180 seconds in this dissolution medium.

Table 80 summarises the dissolution data for formulation examples containing paracetamol alone (Example 32), and paracetamol with tramadol hydrochloride (Example 33) that demonstrate the present invention in 900 mL 0.0033 N hydrochloric acid using USP apparatus 2 at 0 rpm and 37° C.:

TABLE 80

Dissolution data for paracetamol and tramadol hydrochloride in formulations according to the invention at 0 rpm stirring speed in 900 mL 0.0033 N HCl

| Drug | Example | % dissolved in 900 mL 0.0033 N HCl at 0 rpm | | | |
|---|---|---|---|---|---|
| | | 180 sec | 300 sec | 15 min | 30 min |
| Paracetamol | 32-1 (bicarbonate alone) | 3 | 6 | 8 | 12 |
| | 32-2 (bicarbonate + acid) | 37 | 42 | 50 | 55 |
| | Product X | 1 | 1 | 3 | 10 |
| | Product Y (bicarbonate) | 0 | 1 | 3 | 4 |
| Paracetamol from combination product | 33-1 (bicarbonate alone) | 1 | 2 | 7 | 13 |
| | 33-2 (bicarbonate + acid) | 83 | 90 | 94 | 101 |
| Tramadol hydrochloride from combination product | 33-1 (bicarbonate alone) | 1 | 2 | 10 | 25 |
| | 33-2 (bicarbonate + acid) | 93 | 99 | 101 | 103 |

It will be apparent that the use of pH modulating agents in accordance with the present invention substantially increases in vitro dissolution of the therapeutic agents exemplified under conditions without stirring (0 rpm) that highlight the role of microstirring in enhancing dissolution.

It is clear from these results that all formulations containing an acid and a bicarbonate according to the invention had:
a dissolution rate greater than 70% at 180 seconds at 30 rpm in 900 mL 0.0033 N hydrochloric acid where
a dissolution rate greater than 5% at 30 minutes at 0 rpm in 900 mL 0.0033 N hydrochloric acid.

Formulations that contain a base alone and do not demonstrate these rates of dissolution are considered sub-optimal and would be reformulated to optimise the pH modulating agents for maximum dissolution.

The effect of the formulations per se in enhancing dissolution are apparent and the pH change seen with the high level of sodium bicarbonate in Product Y is evident, increasing the pH to 6.6. The dissolution of formulations containing both base and acid are faster than for formulations with base alone which are dependent on external acid in the dissolution medium for the microstirring to enhance dissolution.

Example 32

TABLE 81

Paracetamol Formulations

| Item | | Formulation | |
|---|---|---|---|
| | | 32-1 | 32-2 |
| 1 | Paracetamol (mg) | 500 | 500 |
| 2 | Crospovidone (mg) | 40 | 40 |
| 3 | Sodium bicarbonate (mg) | 200 | 200 |
| 4 | Fumaric acid (mg) | 0 | 34 |
| 5 | Starch 1500 (mg) | 50 | 50 |
| 6 | Povidone (mg) | 34.4 | 40 |
| 7 | Water (mg) | 200 | 0 |
| 8 | Ethanol (mg) | 0 | 125 |
| 9 | Crospovidone (mg) | 60 | 60 |
| 10 | Stearic acid (mg) | 9 | 9 |
| | Total (mg) | 893.4 | 933 |
| | pH modulating agent (% w/w) | 22.4 | 25.1 |
| | Hardness (Kp) | 10 | 17 |
| | Disintegration Time in 0.0033 N HCl (Sec) | 24 | 28 |

Method for Formulation 32-1

Prepare the granulating solution by dissolving Item 6 in Item 7. Blend Items 1, 2 and 5. Spray the granulating solution onto the powder blend in a granulator or mixer to form a granule suitable for compression. Dry the granules at 70° C. inlet temperature in a fluid bed dryer to a loss on drying of ~1% after heating at 100° C. for 5 minutes. Screen through a 1,000 μm sieve. Screen Items 3 and 9 through a 280 μm sieve and blend with the dried granules. Screen Item 10 through a 280 μm sieve and blend with the granule mix. Compress using 19 mm×9 mm oval shallow concave tooling with a break bar on one face to suitable hardness and disintegration time.

Method for Formulation 32-2

Blend Items 1 to 6. Spray Item 8 onto the powder mix in a granulator or mixer to form a granule suitable for compression. Dry the granules at 40° C. to a loss on drying of <1% after heating at 50° C. for 20 min. Screen the granules through a 500 μm sieve. Screen Item 9 through a 280 μm sieve and blend with the dry granules. Screen Item 10 through a 280 μm sieve and blend with the granule mix. Compress using 19 mm×9 mm oval shallow concave tooling with a break bar on one face to suitable hardness and disintegration time.

Dissolution Results

For 900 mL 0.0033 N hydrochloric acid at 30 rpm, dissolution data are summarised in Table 82 and the dissolution profiles are presented in FIG. 60.

TABLE 82

Paracetamol dissolution data in 900 mL 0.0033 N HCl at 30 rpm

% drug dissolved in 900 mL 0.0033 N HCl at 30 rpm Formulation

|  | 32-1 (bicarbonate alone) | 32-2 (bicarbonate + acid) | Product X | Product Y (bicarbonate) |
|---|---|---|---|---|
| 180 sec | 60 | 73 | 16 | 10 |
| 300 sec | 69 | 78 | 30 | 25 |
| 15 min | 85 | 91 | 61 | 57 |
| 30 min | 98 | 102 | 77 | 76 |
| Final pH | 3.0 | 2.9 | 2.3 | 6.6 |

The faster dissolution of the formulation with bicarbonate and acid becomes apparent compared with the use of bicarbonate alone. Both formulations are faster than the two commercial products. The dissolution profile for the commercial product containing sodium bicarbonate is similar to that for the commercial product without any pH modulating agents.

For 900 mL 0.0033 N hydrochloric acid at 0 rpm, dissolution data are summarised in Table 83 and the dissolution profiles are presented in FIG. 61.

TABLE 83

Paracetamol dissolution data in 900 mL 0.0033 N HCl at 0 rpm

% drug dissolved in 900 mL 0.0033 N HCl at 0 rpm Formulation

|  | 32-1 (bicarbonate alone) | 32-2 (bicarbonate + acid) | Product X | Product Y (bicarbonate) |
|---|---|---|---|---|
| 180 sec | 3 | 37 | 1 | 0 |
| 300 sec | 6 | 42 | 1 | 1 |
| 15 min | 8 | 50 | 3 | 3 |
| 30 min | 12 | 55 | 10 | 4 |
| Final pH | 3.0 | 2.9 | 2.3 | 6.6 |

The intrinsic effect of the formulations in enhancing dissolution becomes apparent as the effect of the external acidity is reduced and external stirring is eliminated. Under these conditions, only formulation 32-2 containing the base and acid continues to demonstrate fast and significant levels of dissolution. However the dissolution from formulation 32-1 is still faster over the first 20 minutes than the two commercial products, particularly product Y containing sodium bicarbonate.

Example 33

Paracetamol and Tramadol Hydrochloride

TABLE 84

Paracetamol and Tramadol Hydrochloride Formulations

| Item | | Formulation (mg) 33-1 | 33-2 |
|---|---|---|---|
| 1 | Paracetamol | 325 | 162.5 |
| 2 | Sodium bicarbonate | 200 | 100 |
| 3 | Crospovidone | 10 | 12.5 |
| 4 | Povidone | 0 | 8.4 |
| 5 | Water | 0 | 50 |

TABLE 84-continued

Paracetamol and Tramadol Hydrochloride Formulations

| Item | | Formulation (mg) 33-1 | 33-2 |
|---|---|---|---|
| 6 | Paracetamol | 0 | 162.5 |
| 7 | Tramadol Hydrochloride | 37.5 | 37.5 |
| 8 | Fumaric acid | 0 | 34 |
| 9 | Microcrystalline cellulose | 0 | 50 |
| 10 | Crospovidone | 0 | 12.5 |
| 11 | Povidone | 13.67 | 5 |
| 12 | Water | 55 | 33 |
| 13 | Silicified microcrystalline cellulose | 50 | 0 |
| 14 | Microcrystalline cellulose | 0 | 50 |
| 15 | Crospovidone | 60 | 60 |
| 16 | Magnesium stearate | 0 | 7 |
| 17 | Steric acid | 8 | 0 |
|  | Total (mg) | 704.17 | 701.9 |
|  | pH modulating agent (%) | 28.4 | 19.1 |
|  | Hardness (Kp) | 14 | 10 |
| Disintegration Time in 0.0033 N HCl (Sec) | | 16 | 20 |

Method for Formulation 33-1

Prepare a granulating solution of Item 11 in Item 12. Blend Items 1, 3, and 7. Spray the granulating solution onto the powder mix in a granulator or mixer to form a granule suitable for compression. Dry the granules at 50° C. to achieve moisture content<1%. Screen the granules through a 1,000 μm sieve. Screen Items 2, 13 and 15 through a 280 μm sieve, and blend with the granules. Screen Item 17 through a 280 μm sieve and blend with the granule mix. Compress using 19 mm×7 mm oval shallow concave tooling with a break bar on one face to suitable hardness and disintegration time.

Method for Formulation 33-2

This method of manufacture involves a double granulation.

Prepare a granulating solution of Item 11 in Item 12. Blend Items 6, 7, 8, 9 and 10. Spray the granulating solution onto the powder mix in a granulator or mixer to form a granule suitable for compression. Dry the granules at 70° C. inlet temperature in a fluid bed dryer to a loss on drying of ~1% after heating at 50° C. for 20 minutes.

Prepare a second granulating solution of Item 4 in Item 5. Blend Items 1, 2 and 3. Spray the granulating solution onto the powder blend in a granulator or mixer to form a granule suitable for compression. Dry the granules at 70° C. inlet temperature in a fluid bed dryer to a loss on drying of <1% after heating at 50° C. for 20 minutes.

Screen both granules through a 500 μm sieve and mix. Screen Items 14 and 15 through a 280 μm sieve and blend with the granule mix. Screen Item 16 through a 280 μm sieve and blend with the granule mix. Compress using 19 mm×7 mm oval shallow concave tooling with a break bar on one face to suitable hardness and disintegration time.

Dissolution Results

In 900 mL 0.0033 N hydrochloric acid at 30 rpm, only formulation 33-2 with bicarbonate and acid demonstrates very fast dissolution reaching 100% within 5 minutes.

Formulation 33-1 with the higher level of bicarbonate alone (28%) shows slower dissolution for both drugs although the dissolution of the more soluble tramadol hydrochloride (around 30 mg/ml) is faster than that of the paracetamol with a solubility around 14 mg/ml. Dissolution of this formulation does not show significantly improved dissolution compared with the commercial product.

Tables 85 and 86 show the dissolution data for the two drugs from the combination formulations 33-1 and 33-2 at 30 rpm and 0 rpm respectively.

TABLE 85

Paracetamol and Tramadol Hydrochloride dissolution data in 900 mL 0.0033 N HCl at 30 rpm % drug dissolved in 900 mL 0.0033 N hydrochloric acid at 30 rpm

| Formulation | 33-1 (bicarbonate alone) | | 33-2 (bicarbonate + acid) | | Commercial Product | |
|---|---|---|---|---|---|---|
| | Paracetamol | Tramadol | Paracetamol | Tramadol | Paracetamol | Tramadol |
| 120 sec | 6 | 13 | 89 | 101 | 1 | 3 |
| 180 sec | 11 | 23 | 90 | 102 | 4 | 6 |
| 300 sec | 19 | 40 | 91 | 102 | 12 | 10 |
| 15 min | 39 | 69 | 92 | 103 | 60 | 51 |
| 30 min | 56 | 83 | 94 | 103 | 89 | 95 |
| Final pH | 2.5 | | 2.4 | | 2.2 | |

TABLE 86

Paracetamol and Tramadol Hydrochloride dissolution data in 900 mL 0.0033 N HCl at 0 rpm % drug dissolved in 900 mL 0.0033 N HCl at 0 rpm Formulation

| | 33-1 (bicarbonate alone) | | 33-2 (bicarbonate + acid) | |
|---|---|---|---|---|
| | Paracetamol | Tramadol | Paracetamol | Tramadol |
| 120 sec | 1 | 1 | 78 | 86 |
| 180 sec | 1 | 1 | 83 | 93 |
| 300 sec | 2 | 3 | 85 | 96 |
| 15 min | 7 | 10 | 94 | 101 |
| 30 min | 13 | 25 | 101 | 103 |
| Final pH | 2.8 | | 2.5 | |

At 0 rpm, the intrinsic dissolution enhancing features of the formulations become apparent as the effect of the external acidity of the dissolution medium is reduced and external stirring is eliminated. Under these conditions, formulation 33-2 containing the bicarbonate and acid demonstrates fast and significant levels of dissolution compared with the formulation with bicarbonate alone.

The basic salt tramadol hydrochloride is more soluble than the unionized drug, paracetamol having a solubility in water around 30 mg/mL compared with 14 mg/mL for paracetamol. On a weight for weight basis, the dose of tramadol hydrochloride needs around 1 mL of water for total dissolution compared to around 27 mL for the dose of paracetamol.

In 900 mL 0.0033 N hydrochloric acid at 30 rpm, only the formulation with base and acid (33-2) demonstrates very fast dissolution reaching 100% within 5 minutes.

Formulation 33-1 with the higher level of bicarbonate alone (28%) shows slower dissolution for both drugs although the dissolution of the more soluble tramadol hydrochloride is faster than that of the paracetamol. Dissolution of this formulation does not show significantly improved dissolution compared with the commercial product.

In 900 mL 0.0033 N hydrochloric acid at 0 rpm, the intrinsic dissolution enhancing features of the formulations become apparent as the effect of the external acidity is reduced and external stirring is eliminated. Under these conditions, formulation 33-2 containing the base and acid demonstrates fast and significant levels of dissolution compared with the formulation with base alone.

Conclusion

Based on these results, it is apparent that:
formulations containing bicarbonate alone according to the present invention have a dissolution rate greater than 5% at 30 minutes at 0 rpm, and
formulations containing bicarbonate with a pharmaceutically acceptable acid according to the present invention have a dissolution rate greater than 5% at 300 seconds at 0 rpm.

Examples 34-36

These examples illustrate the effect of formulations of the present invention on the dissolution rates of the three classes of drug exemplified by ibuprofen (acid), paracetamol (unionized) and zolpidem tartrate (salt of a base) under neutral conditions. These approximate the fed state and in vivo conditions where gastric acid has been neutralised or gastric function is suppressed or impaired.

Overview of Examples

Example 34-36 show the effect of sodium bicarbonate alone and in combination with an organic acid on the dissolution of ibuprofen, paracetamol and zolpidem tartrate under neutral conditions.

Table 87 details the formulations for ibuprofen. Tables 88-90 summarise the dissolution data for ibuprofen, paracetamol and zolpidem tartrate respectively.

FIG. 64 shows the dissolution profiles of ibuprofen formulations in 200 mL water at 30 rpm as an example of a neutral dissolution medium. FIGS. 65 and 66 show the dissolution profiles for formulations of paracetamol and zolpidem tartrate in 200 mL full cream milk at 30 rpm which approximates the fed state.

Dissolution Methods

Dissolution was run in 200 mL of the dissolution medium in USP dissolution apparatus 2, stirring at 30 rpm at 37° C. as this lower volume better approximates the likely volumes encountered in vivo. 200 mL 0.015 N hydrochloric acid was used as the acidic dissolution medium for comparison as this is more representative of in vivo levels of acid and volumes in the fasted state when a tablet is ingested with around 150 mL of water.

Full cream milk (Pauls, Parmalat Australia Ltd) containing 3.3% protein, 3.6% fat and 4.8% carbohydrate as sugars was used as a neutral dissolution medium to represent the fed state. The fats and proteins act as a buffer and also increase the viscosity. However, when using milk as a dissolution medium, continuous flow direct measurement of the drug by UV absorbance cannot be used and samples were taken periodically for extraction and assay by HPLC.

For dissolution in full cream milk, the sampling procedure involved the withdrawal of 3 using an autopipette, replacing the sample with the same volume of full cream milk equilibrated at 37° C. Samples were taken at 1, 2, 3, 5, 10, 15, 20 and 30 minutes after adding the tablet into the dissolution vessel. After 30 minutes the stirring speed was increased from 30 rpm to 250 rpm to achieve maximum dissolution and a sample was taken at 45 minutes. The sample was mixed 1:1 with acetonitrile and centrifuged at 13,000 rpm for 20 minutes. The supernatant was passed through a 0.45 micron filter and then the drug content analysed by HPLC.

Although HPLC methods were used for the measurement of paracetamol and zolpidem tartrate, no suitable HPLC method was available for ibuprofen. Therefore for ibuprofen, testing was undertaken in 200 ml purified water to approximate fed conditions where the gastric pH would be neutral rather than acidic. This does not have any buffering capacity and has a low viscosity but has a similar pH to full cream milk, ~pH 6.5. Test formulations were each dissolved in 200 mL full cream milk to determine their effect on the pH of the milk at 37° C. The concentration of ibuprofen in water was measured in a flow through cuvette by UV spectroscopy at a wavelength of 232 nm Example 34

Dissolution results were compared for three ibuprofen formulations according to this present invention, with four commercial products sourced from Australia. These were two standard tablet formulations (AST, NST) and two liquid capsules of the same brands (ALC, NLC) containing solubilised drug that are marketed with "fast relief" claims.

The three formulations detailed in Table 87 were prepared according to the present invention. Formulation 3 contained 400 mg sodium bicarbonate alone, Formulation 1 contained 200 mg bicarbonate with 136 mg fumaric acid and Formulation 2 contained a lower amount of bicarbonate 100 mg with 68 mg fumaric acid.

TABLE 87

Ibuprofen formulations with different pH modifying agents prepared for comparison with commercial products

| Raw material (mg/tablet) | 1 | 2 | 3 |
|---|---|---|---|
| Ibuprofen, 15 grade | 200 | 200 | 200 |
| Croscarmellose sodium | 0 | 0 | 0 |
| Crospovidone | 55 | 40 | 50 |
| Sodium bicarbonate, fine | 200 | 100 | 400 |
| Fumaric acid | 136 | 68 | 0 |
| Microcrystalline cellulose | 300 | 206 | 340 |
| Magnesium stearate | 9 | 6 | 10 |
| Total | 900 | 620 | 1000 |
| Hardness Kp | 5.5 | 7 | 5.6 |
| Disintegration time in 0.0033 N HCl (sec) | 10 | 15 | 70 |

Method
1. Pass ibuprofen, microcrystalline cellulose, bicarbonate and organic acid (if used) through a 280 micron screen to remove any aggregates
2. Add superdisintegrant, either croscarmellose sodium or crospovidone to the powder blend from 1 and mix well.
3. Pass magnesium stearate through a 280 micron screen and mix with 2.
4. Compress using a 19×9 mm oval shaped tooling on Cadmach CMD3 B-16 tablet press, at a suitable hardness to achieve a short disintegration time.

Results and Discussion

Dissolution results in 200 mL water at 30 rpm are summarised for the commercial products and fast dissolving formulations of the present invention in Table 88. Dissolution profiles are shown in FIG. 64.

TABLE 88

Summary dissolution data for a ibuprofen formulation according to the present invention compared with two standard tablets and two liquid gel commercial products in 200 mL water at 30 rpm

| Formulation | % drug dissolved in 200 mL water at 30 rpm | | | | | | |
|---|---|---|---|---|---|---|---|
| Product/Time | AST | ALC | NST | NLC | 1 | 2 | 3 |
| 180 seconds | 0 | 0 | 0 | 0 | 47 | 46 | 86 |
| 300 seconds | 0.6 | 0 | 0 | 0.3 | 51 | 50 | 86 |
| 15 minutes | 0.5 | 2 | 0.3 | 1 | 60 | 55 | 86 |
| Final pH | 4.7 | 5.2 | 4.5 | 4.7 | 5.0 | 4.8 | — |

The results with the formulations of the present invention are in stark contrast to the dissolution performance of the commercial products whether the standard tablet formulation or a solubilised liquid capsule formulation. None of the commercial products demonstrated significant dissolution in water.

All products made according to the present invention showed rapid dissolution in water, although the formulation containing 400 mg sodium bicarbonate alone reached a higher plateau than the two formulations containing additional fumaric acid. These showed a similar fast rate of dissolution reaching around 50% dissolution in 3 minutes followed by a slowly rising plateau. While this initial fast dissolution was similar to that achieved with 400 mg sodium bicarbonate, the extent of dissolution was less demonstrating the effect of pH on the solubility of the ibuprofen. The higher level of acid:base couple achieved a slightly higher pH which resulted in a higher maximum dissolution after the stirring is increased, again highlighting the importance of pH on the solubility of the ibuprofen.

Although the final pH values with the products made according to the present invention were similar to those achieved for the commercial products, they achieved a higher level of dissolution. This demonstrates the effect of the effervescence and the increased pH of the micro-environment around the dissolving drug particles which together enhance the dissolution of this acidic drug.

From these results it appears that a combination of 100 mg sodium bicarbonate and 68 mg of fumaric acid is sufficient to provide rapid but incomplete dissolution under these conditions. The plateau occurs below 100% because the pH of 4.8-5 is insufficient to allow complete dissolution of the ibuprofen in 200 mL water even when the stirring rate increased. In contrast, the tablets with 400 mg sodium bicarbonate produce a sufficient increase in pH such that 100% dissolution is achieved when the stirring is increased.

When added to full cream milk, all products achieved a similar pH in the range 6.3-6.8 indicating effective buffering to around the pH of intestinal fluids from which absorption occurs in vivo. In milk, the drop in pH seen in water does not occur so at this higher pH, the ibuprofen will have a higher solubility and the extent of dissolution is expected to increase for all products. At this pH, 200 mL. water would dissolve 826 mg of ibuprofen which exceeds the 200 mg dose being tested.

Based on these results, it is expected that for the inventions according to the present invention which contain sodium bicarbonate and fumaric acid:
  the rate of dissolution will be significantly faster than the four commercial products as a result of the microstirring and the local pH effect
  the extent of dissolution will be higher in milk than observed in water as a result of the higher pH The formulations of the present invention showed fast dissolution in 200 mL water used to approximate fed state or neutral pH conditions, with the extent of dissolution being related to the final pH achieved. Lower levels of sodium bicarbonate combined with a 1:1 stoichiometric amount of fumaric acid also achieve fast dissolution but the pH is limited by the final pH which is lower than with 400 mg sodium bicarbonate alone. In neutral or alkaline media, and in more viscous media such as milk, it is expected that formulations containing sodium bicarbonate with an organic acid will perform better.

Example 35

This example describes the dissolution of three paracetamol formulations according to the present invention when tested in 200 mL full cream milk and compared with the two commercial products described in Example 32. Product X contains no bicarbonate. Product Y contains 630 mg sodium bicarbonate per tablet.

One example contains only 200 mg bicarbonate and is formulation 2 described in Example 4, designated Ex 4-2. A second example contains 200 mg bicarbonate with 34 mg fumaric acid and is formulation 2 described in Example 32, designated Ex 32-2. The third example contains 200 mg bicarbonate with an equimolar quantity of fumaric acid, 134 mg. These tablets were made using the same method as described in Example 32, but containing the increased amount of fumaric acid and compressed at 1035 mg instead of 933 mg. This example is designated Ex 35-1.

Table 89 summarises the dissolution data and FIG. 65 shows the dissolution profiles for these five tablets when tested in 200 mL full cream milk.

Results and Discussion

TABLE 89

Summary dissolution data for paracetamol formulations according to the present invention compared with two commercial products in 200 mL different dissolution media at 30 rpm

| Formulation | % drug dissolved in 200 mL full cream milk at 30 rpm | | | | |
|---|---|---|---|---|---|
| Product/Time | X | Y | Ex 4-2 | Ex 32-2 | Ex 35-1 |
| Bicarbonate (mg) | 0 | 630 | 200 | 200 | 200 |
| Acid (mg) | 0 | 0 | 0 | 34 | 136 |
| 180 seconds | 1 | 2 | 17 | 49 | 95 |
| 300 seconds | 2 | 2 | 28 | 55 | 87 |
| 15 minutes | 2 | 21 | 74 | 62 | 89 |
| Final pH | 6.6 | 7.0 | 6.8 | 7.9 | 6.5 |

The results clearly show the benefit of the present invention compared with both commercial products. Product X with no bicarbonate shows negligible dissolution in milk until the stirring speed is increased to 250 rpm at 30 minutes, and even then is not completely dissolved after fast stirring for 15 minutes.

Although product Y containing 630 mg sodium bicarbonate does show enhanced dissolution once the coat has dissolved, it is not as fast as Ex 4.2 according to the present invention which contains only 200 mg bicarbonate.

Addition of an organic acid increases the initial rate of dissolution as seen with Ex 32-2 and Ex 35-1 which appears proportional to the level of acid added as demonstrated by the slowing of the dissolution after initial reaction between the acid and bicarbonate in the tablet.

Based on these results it appears that when formulated according to the present invention, paracetamol dissolution of greater than 50% can be achieved in 15 minutes when stirred at 30 rpm. When bicarbonate is used with an organic acid, then faster dissolution is achieved in 200 mL full cream milk exceeding 50% in 300 seconds.

Example 36

This example describes the dissolution profiles of a zolpidem tartrate formulation according to the present invention and a commercial tablet in different dissolution media. The tablets tested were made according to formulation 3 described in Example 29 (Ex 29-3).

Table 90 summarises the dissolution data and FIG. 66 shows the dissolution profiles for these tablets when tested in 200 mL full cream milk, 200 mL 0.0033 N hydrochloric acid and 200 mL 0.015 N hydrochloric acid.

Results and Discussion

TABLE 90

Summary dissolution data for a zolpidem tartrate formulation according to the present invention (Ex 29-3) compared with a commercial product (S) in 200 mL different dissolution media at 30 rpm

| | % drug dissolved in 200 mL dissolution medium at 30 rpm Dissolution medium | | | | | |
|---|---|---|---|---|---|---|
| Formulation | Full cream milk | | 0.0033 N HCl | | 0.015 N HCl | |
| Product/Time | Ex 29-3 | S | Ex 29-3 | S | Ex 29-3 | S |
| 180 seconds | 96 | 0.1 | 86 | 0.8 | 91 | 0.9 |
| 300 seconds | 96 | 0.6 | 87 | 9 | 91 | 4 |
| 15 minutes | 94 | 7 | 90 | 34 | 91 | 40 |
| Final pH | 6.6 | 6.5 | 2.7 | 2.4 | 1.8 | 1.7 |

As seen from Table 90, the formulation according to the present invention demonstrates fast dissolution exceeding 80% dissolution in 300 seconds, in all three dissolution media, regardless of the pH. In contrast, the commercial product showed much slower dissolution in milk compared with the two acidic dissolution media, reaching only 7% dissolved after 15 minutes.

Conclusions

Based on these results, it is apparent that for ibuprofen, an acid drug, paracetamol an unionized drug and zolpidem tartarte, the salt of a basic drug, formulations containing bicarbonate with a pharmaceutically acceptable acid according to the present invention:
  have a dissolution rate greater than 50% at 300 seconds at 30 rpm in 200 mL neutral dissolution media such as full cream milk
  have a dissolution rate greater than 70% at 300 seconds at 30 rpm in 200 mL low acid dissolution media such as 0.0033 N hydrochloric acid As such, fast in vivo dissolution would be expected from formulations containing bicarbonate with a pharmaceutically acceptable acid according to the present invention under a wide range of in vivo conditions from fed to fasted, and from normal to abnormal gastric function. In turn this would be expected to facilitate in vivo absorption to the extent allowed by the intestinal permeability of the drug.

BIBLIOGRAPHY

Amidon G L et al, *A theoretical basis for a biopharmaceutic drug classification: the correlation of in vitro drug product dissolution and in vivo bioavailability*, Pharm Res, 1995, 12 (3) 813-20

Balan G, et al., *In vitro-in vivo correlation (IVIVC) models for metformin after administration of modified-release (MR) oral dosage forms to healthy human volunteers*, J Pharm Sci 2001, 90 (8) 1176-1185

FDA, 1997, Centre for Drug Evaluation and Research (CDER), *Guidance for Industry: Dissolution Testing of Immediate Release Oral Dosage Forms*, August 1997

FDA, 2000, Centre for Drug Evaluation and Research (CDER), *Guidance for Industry: Waiver of In Vivo Bioavailability and Bioequivalence Studies for Immediate-Release Solid Oral Dosage Forms Based on a Biopharmaceutics Classification System*, August 2000

Grattan T. et al, *A five way crossover human volunteer study to compare the pharmacokinetics of paracetamol following oral administration of two commercially available paracetamol tablets and three development tablets containing paracetamol in combination with sodium bicarbonate or calcium carbonate*, Eur J Pharm Biopharm, 2000, 49(3) 225-229.

Kelly K et al, *Comparison of the rates of disintegration, gastric emptying, and drug absorption following administration of a new and a conventional paracetamol formulation, using γ scintigraphy*, Pharm Res, 2003, 20 (10) 1668-1673

Neuvonen P J and Kivisto K T, *Enhancement of Drug Absorption by Antacids*, Clin Pharmacokinet 1994, 27 (2) 120-128

Rostami-Hodjegan A et al, *A new rapidly absorbed paracetamol tablet containing sodium bicarbonate. II. Dissolution studies and in vitro/in vivo correlation*, Drug Dev Ind Pharm, 2002, 28 (5) 733-43

The invention claimed is:

1. A swallow formulation comprising:
   (a) a therapeutic compound that is selected from the group consisting of naproxen, salts thereof, and combinations thereof, and
   (b) an appropriate amount of one or more pH modulating agents that include an appropriate amount of one or more soluble carbonates in an amount that will neutralise 0.01 to 10 millimoles of hydrochloric acid, and is present in an amount from about 5% to 75% by weight of the swallow formulation, wherein the therapeutic compound exhibits a dissolution profile of:
   at least 50% dissolution from the swallow formulation within 300 seconds, when the above is measured at 30 rpm in United States Pharmacopoeia dissolution apparatus 2 with 900 mL 0.0033 N hydrochloric acid at 37° C.;
   wherein said formulation further comprises a water uptake agent;
   wherein the weight ratio of the water uptake agent to soluble carbonate is in the range of about 0.1:1-20:1, and
   wherein the one or more pH modulating agents includes between about 8 mg and 700 mg of soluble carbonates per swallow formulation.

2. The swallow formulation according to claim 1, wherein at least 40% of the therapeutic compound is dissolved from the swallow formulation within 240 seconds in United States Pharmacopoeia dissolution apparatus 2 with 900 mL 0.0033N hydrochloric acid at 30 rpm and 37° C.

3. The swallow formulation according to claim 1, wherein at least 20% of the therapeutic compound is dissolved from the swallow formulation within 180 seconds in United States Pharmacopoeia (USP) dissolution apparatus 2 with 900 mL 0.0033 N hydrochloric acid at 30 rpm and 37° C.

4. The swallow formulation according to claim 1 wherein the therapeutic compound is naproxen sodium.

5. The swallow formulation according to claim 1 wherein the pH modulating agent of the swallow formulation comprises an appropriate amount of one or more pharmaceutically acceptable acids and one or more soluble carbonates.

6. The swallow formulation according to claim 1 wherein the soluble carbonate is selected from the group consisting of sodium carbonate, sodium bicarbonate, calcium carbonate, magnesium carbonate, ammonium carbonate, ammonium bicarbonate, potassium bicarbonate, sodium glycine carbonate, disodium glycine carbonate, arginine carbonate and lysine carbonate.

7. The swallow formulation according to claim 1 wherein the carbonate is sodium bicarbonate.

8. The swallow formulation according to claim 1 further comprising a pharmaceutically acceptable acid selected from the group consisting of citric acid, tartaric acid, succinic acid, ascorbic acid, malic acid, fumaric acid, metatartaric acid, adipic acid, sodium acid citrate, potassium acid citrate, glycine citrate, potassium acid tartrate, sodium acid tartrate, aspartic acid, glutamic acid, glycine, leucine, tyrosine, tryptophan, glycine fumarate, glycine hydrochloride, monophosphate glycine and combinations thereof.

9. The swallow formulation according to claim 8 wherein the pharmaceutically acceptable acid is citric acid.

10. The swallow formulation according to claim 8 wherein the pharmaceutically acceptable acid is citric acid, the soluble carbonate is sodium bicarbonate and the therapeutic compound is naproxen sodium.

11. The swallow formulation according to claim 1 wherein the water uptake agent is selected from the group consisting of cross-linked polyvinylpyrrolidone, croscarmellose sodium, sodium starch glycolate, starch, starch derivatives, hydroxypropylcellulose, low substituted hydroxypropylcellulose, hydroxypropylmethylcellulose, alginic acid, sodium alginate, calcium sulfate, sodium carboxymethylcellulose, calcium carboxymethylcellulose, microcrystalline cellulose, powdered cellulose, colloidal silicon dioxide, docusate sodium, guar gum, magnesium aluminium silicate, methylcellulose, polacrilin potassium, silicified microcrystalline cellulose, magnesium oxide, tragacanth, mannitol, sorbitol, xylitol, sucrose, lactose, fructose, maltose, polyethylene glycol, amino acids, cyclodextrin, urea and/or polyvinylpyrrolidone and combinations thereof.

12. The swallow formulation according to claim 1 further comprising one or more additional therapeutic compounds selected from the group consisting of basic drugs, amphoteric drugs, acidic drugs, unionized drugs and their salts.

13. The swallow formulation according to claim 1 wherein the therapeutic compound exhibits a dissolution profile of at least 20% dissolution from the swallow formulation within 300 seconds when measured at 30 rpm in USP dissolution apparatus 2 with 200 mL full cream milk at 37° C.

14. The swallow formulation according to claim 1 wherein the therapeutic compound exhibits a dissolution profile of at least 40% dissolution from the swallow formulation within 180 seconds when measured at 30 rpm in USP dissolution apparatus 2 with 200 mL full cream milk at 37° C.

15. The swallow formulation according to claim 1 wherein the therapeutic compound exhibits a dissolution profile of at least 75% dissolution from the swallow formulation within 120 seconds when measured at 30 rpm in USP dissolution apparatus 2 with 200 mL full cream milk at 37° C.

\* \* \* \* \*